United States Patent [19]

Takahashi et al.

[11] Patent Number: 6,130,243
[45] Date of Patent: Oct. 10, 2000

[54] 1,4-BENZODIOXIN DERIVATIVES

[75] Inventors: Toshihiro Takahashi; Kohei Inomata; Norio Oshida; Nobutoshi Kubota; Tamiko Hamada; Naohito Iwata, all of Saitama, Japan

[73] Assignee: Nisshin Flour Milling Co., Ltd., Tokyo, Japan

[21] Appl. No.: 08/945,879

[22] PCT Filed: May 13, 1996

[86] PCT No.: PCT/JP96/01252

§ 371 Date: Nov. 12, 1997

§ 102(e) Date: Nov. 12, 1997

[87] PCT Pub. No.: WO96/35685

PCT Pub. Date: Nov. 14, 1996

[30] Foreign Application Priority Data

May 12, 1995 [JP] Japan ................................. 7-137440

[51] Int. Cl.[7] ..................... A61K 31/335; C07D 319/20
[52] U.S. Cl. ............................. 514/452; 549/362
[58] Field of Search ................. 549/362; 514/452

[56] References Cited

U.S. PATENT DOCUMENTS 4,205,079  5/1980  Durham et al. ........................ 549/366
5,482,971  1/1996  Epstein et al. ........................ 514/465

FOREIGN PATENT DOCUMENTS 56-5444   1/1981  Japan .
5-320153  11/1993 Japan .
6-293664  10/1994 Japan .
7-2831    1/1995  Japan .
7-228543  8/1995  Japan .

OTHER PUBLICATIONS

Letters To Nature, vol. 309 May 10, 1984, Atypical B–adrenoceptor on brown adipocytes as target for anti–obesity drugs, J.R.S. Arch, A.T. Ainsworth, M.A. Cawthorne, V. Piercy, M.V. Sennitt, V.E. Thody, C. Wilson & S. Wilson.
Molecular Pharmacology, vol. 42, pp. 753–759 (1992). Coexisting $B_1$–And Atypical B–Adrenergic Receptors Cause Redundant Increases in Cyclic AMP in Human Neuroblastoma Cells.
American Chemical Society J. Org. Chem 1988, 53, 2861–2863.
American Chemical Society J. Med. Chem. 35, 1992, 35, 3081–3084.
Proc. Natl. Sci. USA, vol. 90, pp. 3669, Apr. 1993, Biochemistry Structural basis for receptor subtype–specific regulation revealed by a chimeric $B_3/B_2$–adrenergic receptor.

Primary Examiner—Bernard Dentz
Attorney, Agent, or Firm—Oblon, Spivak, McClelland, Maier & Neustadt, P.C.

[57] ABSTRACT

A 1,4-benzodioxin derivative represented by formula (I)

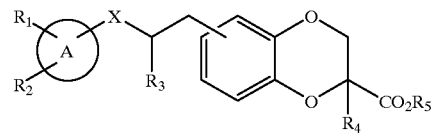

(I)

wherein A is an aryl group or a $(C_3-C_8)$cycloalkyl group, $R_1$ and $R_2$ individually are a hydrogen atom, a halogen atom, an alkyl group, a trifluoromethyl group, an alkoxy group, an aryl group, an aryloxy group, or $R_1$ and $R_2$ together form a methylenedioxy group, $R_3$ is a hydrogen atom or an alkyl group, $R_4$ is a hydrogen atom or $CO_2R_5$, $R_5$ is a hydrogen atom or an alkyl group, X is a radical of formula (II) or (III)

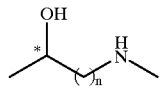

(II)

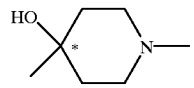

(III)

wherein n is 1 or 2.

The compounds are useful for a prophylactic or therapeutic agent for diabetes, hyperglycemia and obesity.

14 Claims, No Drawings

1,4-BENZODIOXIN DERIVATIVES

This is a 371 of PCT/JP96/01252 filed May 13, 1996.

TECHNICAL FIELD

The present invention relates to novel 1,4-benzodioxin derivatives, pharmaceutically acceptable salts thereof and processes for their preparation.

Further, the invention relates to a prophylactic or therapeutic agent for diabetes, hyperglycemia and obesity in mammals comprising as an active ingredient a compound of this invention.

BACKGROUND ART

Diabetes mellitus is the disease which fails to utilize glucose in the body sufficiently. It follows that increases of blood glucose level or chronic hyperglycemia are caused and various complications are induced. It is absolutely important to normalize blood glucose levels in the treatment of diabetes. For the purpose, parenteral administration of insulin (the hormone which regulates blood glucose), oral administration of drugs and dietary therapies have now been carried out. Diabetes mellitus is classified into two major forms of type I diabetes and type II diabetes.

Type I diabetes is the result of a deficiency of insulin; which is basically improved by administration of insulin. On the other hand, type II diabetes, which is insulin-independent diabetes, occurs in the face of normal or even elevated levels of insulin. This means that the tissue response to insulin is impaired. In the treatment of type II diabetes, oral administration of drugs which promote insulin secretion or repress absorption of sugar containing in the diet, parenteral administration of insulin and dietary therapies have been carried out. However, these are not fundamental methods for the treatment of diabetes, and patients frequently suffer from side effects and pains. Therefore, it has been desired to develop drugs improving pathosis of diabetes. In addition, most of the type II diabetes are also associated with obesity which is closely related to occurrence of diabetes. It is known that in a patient suffering from diabetes and obesity, diabetes is improved by healing obesity.

Obesity is thought to be caused by accumulation of fat in the body, and in order to improve obesity, it is necessary to consume fat. Recently, obesity or diabetes has become a problem in pets as well as humans due to excess nutrition and lack of exercise. Additionally, it has been desired to decrease fat and increase lean meat of edible animals.

It is known that β-adrenergic receptors are divided into β1, β2, and β3-subtypes. Stimulation of β1 receptors mainly causes increase in heart rate. Stimulation of β2 receptors mainly causes bronchodilation and smooth muscle relaxation. Stimulation of β3 receptors mainly promotes lipolysis (the breakdown of adipose tissue trigylcerides to glycerol and free fatty acids) and energy consumption, by which the decrease in fat mass is invoked. Accordingly, it is thought that compounds having β3 agonistic activity possess anti-obesity activity. It is reported that these compounds have anti-hyperglycemic activity in animal models of type II diabetes. These indicate that β3 agonists are useful in improving obesity in mammals and hyperglycemia in diabetes of mammals.

Compounds below are known as main β3 agonists.

Ainsworth et al., in Japanese Patent Kokai 56-5444, disclose a compound (BRL 37344) of the following formula (XVI)

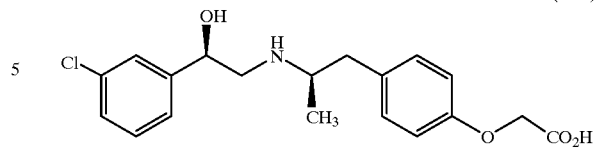

and its carboxylic acid methyl ester (BRL 35135) or a pharmaceutically acceptable salt thereof. These compounds have anti-obesity activity and anti-hyperglycemic activity. BRL 35135 has also lipolytic activity (β3) in rats (Nature, Vol. 309, 163, 1984). Effects on β3 adrenergic receptors show that these compounds are useful as anti-obesity drugs. Further, it is reported that these compounds have anti-hyperglycemic activity in animal models of type II diabetes. The treatment for diabetes or obesity using β3 agonists has disadvantages of possibility of stimulating other β receptors and side-effects resulting therefrom. They are, for example, muscle tremor caused by stimulating β2 receptors and increase in heart rate caused by stimulating β1 receptors. BRL 35135 has β3 agonistic activity, but, at the same time, it has β1 or β2 agonistic activity, which is thought to cause such side-effects.

Bloom et al., in Japanese Patent Kokai 5-320153, disclose a compound (CL 316243) of the following formula (XVII)

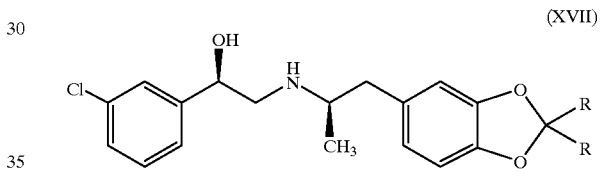

wherein R is a carboxy group, an alkoxycarbonyl group or a salt thereof.

Epstein et al., in Japanese Patent Kokai 7-2831, disclose a compound of the following formula (XVIII)

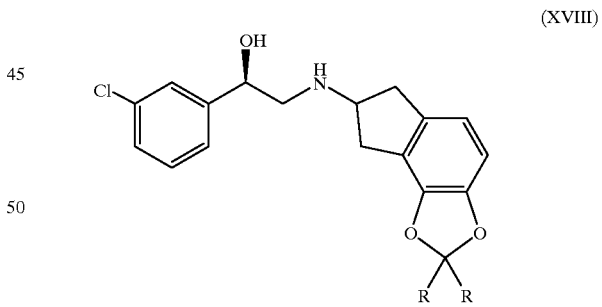

wherein R is a carboxy group, an alkoxycarbonyl group or a salt thereof. The above-mentioned compounds have greater agonistic activity to β3 than to β1 and β2, with the selectivity. The compounds of the above-mentioned formulae (XVII) and (XVIII) have β3 agonistic activity in the experiment using rodents, in particular rats, but β3 agonistic activity in human is still unknown.

Recently, the methods for estimating the activity in human more exactly have been developed. Human β3 agonistic activity can be determined by using the cloned human β3 receptors which are expressed in the neuroblastoma cells and measuring the increase of cAMP production according to these analysis. The agonistic activity of various compounds to this cultured cells offers the index of human β3 agonistic activity (Molecular Pharmac., Vol. 42, 753, 1992).

β3 agonists are useful as anti-obesity drugs or anti-diabetes drugs, while the number of patients with obesity or diabetes tends to increase every year. Therefore, it has been desired to develop compounds having a chemical structure different from known β3 agonists and having distinct human β3 agonistic activity.

DISCLOSURE OF THE INVENTION

We have studied in an effort to find out a compound having human β3 agonistic activity and anti-hyperglycemic activity in animal models of type II diabetes. As a result, we have found that 1,4-benzodioxin derivatives having specific structures satisfy these requirements. The present compounds induce lipolysis in adipocyte of rats (rat β3 agonistic activity) and increase cAMP production in the neuroblast cells having human β3 receptors (human β3 agonistic activity). Additionally, they have anti-hyperglycemic activity in animal models of type II diabetes.

The present invention is concerned with a 1,4-benzodioxin derivative represented by formula (I)

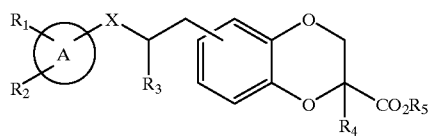

(I)

wherein
A is an aryl group or a $(C_3-C_8)$cycloalkyl group,
$R_1$ and $R_2$ may be the same or different, and each is a hydrogen atom, a halogen atom, a $(C_1-C_6)$alkyl group, a trifluoromethyl group, a $(C_1-C_6)$alkoxy group, an aryl group, an aryloxy group or an aryl$(C_1-C_6)$alkyloxy group, the aryl, aryloxy or aryl$(C_1-C_6)$alkyloxy group being optionally substituted by one or two halogen atoms, or $R_1$ and $R_2$ together form $-OCH_2O-$,
$R_3$ is a hydrogen atom or a $(C_1-C_6)$alkyl group,
$R_4$ is a hydrogen atom or $CO_2R_5$,
$R_5$ is a hydrogen atom or a $(C_1-C_6)$alkyl group and
x is a divalent radical of formula (II) or (III)

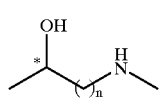

(II)

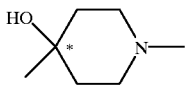

(III)

wherein n is 1 or 2,
and a pharmaceutically acceptable salt thereof.

This invention is further concerned with a prophylactic or therapeutic agent for diabetes, hyperglycemia and obesity in mammals comprising as an active ingredient a compound represented by formula (I) above or a pharmaceutically acceptable salt thereof.

In the formulae of this specification, the asterisked (*) carbon atoms are asymmetric ones.

In formula (I) of this invention, examples of the aryl group represented by A include phenyl, naphthyl and the like. Examples of the $(C_3-C_8)$cycloalkyl group include cyclopropyl, cyclobutyl, cyclopentyl, cyclohexyl, cycloheptyl, cyclooctyl and the like.

Examples of the halogen atom represented by $R_1$ and $R_2$ include fluorine, chlorine, bromine and iodine. The $(C_1-C_6)$ alkyl group can be straight or branched-chain alkyl groups, examples of which include methyl, ethyl, propyl, isopropyl, butyl, sec-butyl, t-butyl, pentyl, isopentyl, hexyl, isohexyl and the like. The $(C_1-C_6)$alkoxy group can be straight or branched-chain alkoxy groups, examples of which include methoxy, ethoxy, propoxy, isopropoxy, butoxy, isobutoxy, t-butoxy, pentoxy, isopentoxy, hexoxy, isohexoxy and the like. Examples of the aryl group include phenyl, naphthyl and the like. Examples of the aryloxy group include phenoxy, naphthoxy and the like. Examples of the aryl $(C_1-C_6)$alkyloxy group include benzyloxy, phenethyloxy, phenylpropyloxy, naphthylmethyloxy and the like.

The $(C_1-C_6)$alkyl group represented by $R_3$ can be straight or branched-chain alkyl groups, examples of which include methyl, ethyl, propyl, isopropyl, butyl, sec-butyl, t-butyl, pentyl, isopentyl, hexyl, isohexyl and the like.

The $(C_1-C_6)$alkyl group represented by $R_5$ can be straight or branched-chain alkyl groups, examples of which include methyl, ethyl, propyl, isopropyl, butyl, sec-butyl, t-butyl, pentyl, isopentyl, hexyl, isohexyl and the like.

In the present invention, a 1,4-benzodioxin derivative represented by formula (I')

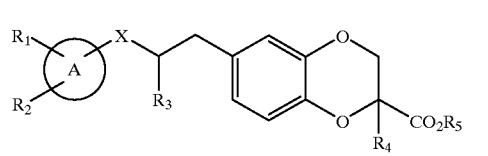

(I')

wherein A, $R_1$, $R_2$, $R_3$, $R_4$, $R_5$ and X have the same meanings as given above, is particularly useful.

A preferable compound according to the present invention is the compound of the above formula (I) or (I'), wherein A is a phenyl group or a $(C_4-C_7)$cycloalkyl group, $R_1$ and $R_2$ may be the same or different, and each is a hydrogen atom, a halogen atom, a $(C_1-C_4)$alkyl group, a trifluoromethyl group, a $(C_1-C_4)$alkoxy group, a phenyl group, a phenoxy group or a benzyloxy group which may be optionally substituted by a halogen atom, or $R_1$ and $R_2$ together form $-OCH_2O-$, $R_3$ is a $(C_1-C_4)$alkyl group, $R_4$ is a hydrogen atom or $CO_2R_5$ $R_5$ is a hydrogen atom or a $(C_1-C_4)$alkyl group and X is a divalent radical of formula (II) or (III), or a pharmaceutically acceptable salt thereof.

More preferable is the compound of formula (I) or (I') wherein A is a phenyl group or a cyclohexyl group, both $R_1$ and $R_2$ are a hydrogen atom, or one of $R_1$ and $R_2$ is a hydrogen atom and the other is a halogen atom, a $(C_1-C_4)$ alkyl group, a trifluoromethyl group, a $(C_1-C_4)$alkoxy group, a phenyl group, a phenoxy group or a benzyloxy group which may be optionally substituted by a halogen atom, or $R_1$ and $R_2$ together form $-OCH_2O-$, $R_3$ is a $(C_1-C_4)$alkyl group, $R_4$ is a hydrogen atom, $R_5$ is a hydrogen atom or a $(C_1-C_4)$alkyl group and X is a divalent radical of formula (II) or (III), or a pharmaceutically acceptable salt thereof.

Still more preferable is the compound of formula (I) or (I') wherein A is a phenyl group, both $R_1$ and $R_2$ are a hydrogen atom, or one of $R_1$ and $R_2$ is a hydrogen atom and the other is a fluorine atom, a chlorine atom, a methyl group, a trifluoromethyl group, a methoxy group, a phenyl group, a phenoxy group or a benzyloxy group which may be optionally substituted by a chlorine atom, or $R_1$ and $R_2$ together form —$OCH_2O$—, $R_3$ is a methyl group, $R_4$ is a hydrogen atom, $R_5$ is a hydrogen atom, a methyl group or an ethyl group and X is a divalent radical of formula (II) wherein n is 1, or a pharmaceutically acceptable salt thereof.

Especially preferable compounds of the present invention are the following 1,4-benzodioxin derivatives, 6-{2-[2-hydroxy-2-(3-methoxyphenyl)ethyl]amino}propyl-2,3-dihydro-1,4-benzodioxin-2-carboxylic acid methyl ester, 6-{2-[2-hydroxy-2-(3-tolyl)ethyl]amino}propyl-2,3-dihydro-1,4-benzodioxin-2-carboxylic acid methyl ester, 6-[2-(2-hydroxy-2-phenylethyl)amino]propyl-2,3-dihydro-1,4-benzodioxin-2-carboxylic acid methyl ester, 7-[2-(2-hydroxy-2-phenylethyl)amino]propyl-2,3-dihydro-1,4-benzodioxin-2-carboxylic acid methyl ester, 6-[2-(2-hydroxy-2-piperonylethyl)amino]propyl-2,3-dihydro-1,4-benzodioxin-2-carboxylic acid methyl ester, 6-{2-[2-(3-chlorophenyl)-2-hydroxyethyl]amino}propyl-2,3-dihydro-1,4-benzodioxin-2-carboxylic acid methyl ester, 6-{2-[2-hydroxy-2-(3-trifluoromethylphenyl)ethyl]amino}propyl-2,3-dihydro-1,4-benzodioxin-2-carboxylic acid methyl ester, 6-{2-[2-hydroxy-2-(4-fluorophenyl)ethyl]amino}propyl-2,3-dihydro-1,4-benzodioxin-2-carboxylic acid methyl ester, (2'R,2"R)-6-{2-[2-(3-chlorophenyl)-2-hydroxyethyl]amino}propyl-2,3-dihydro-1,4-benzodioxin-2-carboxylic acid ethyl ester, (2'S,2"R)-6-{2-[2-(3-chlorophenyl)-2-hydroxyethyl]amino}propyl-2,3-dihydro-1,4-benzodioxin-2-carboxylic acid ethyl ester, (2R,2'R,2"R)-6-{2-[2-(3-chlorophenyl)-2-hydroxyethyl]amino}propyl-2,3-dihydro-1,4-benzodioxin-2-carboxylic acid ethyl ester hydrochloride, (2R,2'S,2"R)-6-{2-[2-(3-chlorophenyl)-2-hydroxyethyl]amino}propyl-2,3-dihydro-1,4-benzodioxin-2-carboxylic acid ethyl ester, (2S,2'R,2"R)-6-{2-[2-(3-chlorophenyl)-2-hydroxyethyl]amino}propyl-2,3-dihydro-1,4-benzodioxin-2-carboxylic acid ethyl ester, (2S,2'S,2"R)-6-{2-[2-(3-chlorophenyl)-2-hydroxyethyl]amino}propyl-2,3-dihydro-1,4-benzodioxin-2-carboxylic acid ethyl ester.

The present compounds represented by formula (I) can include the possible optical isomers and metabolic products and their metabolic precursors.

The compounds of formula (I) may be prepared by various conventional processes, for example, the processes shown below.

(a) 1,4-Benzodioxin derivative represented by formula (VII)

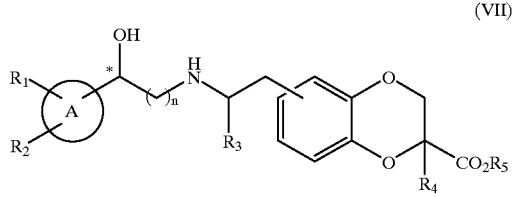

(VII)

wherein A, $R_1$, $R_2$, $R_3$, $R_4$, $R_5$ and n are as defined for formula (I) may be prepared by reacting a compound of formula (IV)

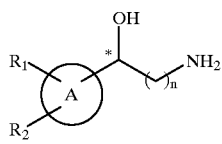

(IV)

wherein A, $R_1$, $R_2$ and n are as defined for formula (I) with a compound of formula (V)

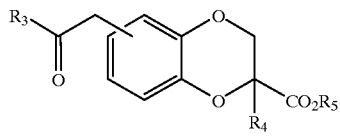

(V)

wherein $R_3$, $R_4$ and $R_5$ are as defined for formula (I) to prepare a compound of formula (VI)

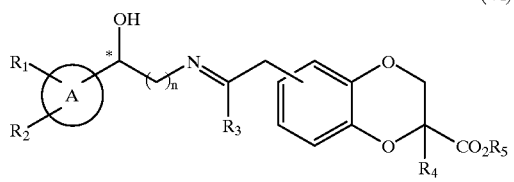

(VI)

wherein A, $R_1$, $R_2$, $R_3$, $R_4$, $R_5$ and n are as defined for formula (I) (Step A), followed by reducing the compound of formula (VI) (Step B).

Step A is the step of preparing the compound of formula (VI), and is usually carried out in the presence of a solvent. The reaction may be carried out while removing a resulting water with Dean-Stark apparatus etc., or in the presence of a dehydrating agent such as anhydrous sodium carbonate, anhydrous potassium carbonate, anhydrous sodium sulfate, anhydrous calcium chloride, anhydrous magnesium sulfate, molecular sieves and the like.

Solvents employed are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; and the mixtures thereof.

The reaction may be carried out at a temperature ranging from ice-cooling to reflux-heating. The reaction time can be varied, depending on a reagent and a reaction temperature, etc., and is usually 0.5 to 12 hours. The reaction is preferably carried out under reflux-heating in the solvent such as hydrocarbons or alcohols for 1 to 5 hours. More preferably, the reaction is carried out by dehydration under reflux-heating in benzene for 1 to 3 hours.

Step B is the step of reducing the compound of formula (VI) to prepare the compound of formula (VII). The reaction is usually carried out in the presence of a reducing agent or by hydrogenation in the presence of a catalyst. Reducing agents which can be used are metal hydrides such as lithium borohydride, sodium borohydride, sodium cyanoborohydride, lithium aluminum hydride, diisobutyl aluminum hydride and the like.

The reaction is usually carried out in the presence of a solvent. Solvents used are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; water; and the mixtures thereof.

The reaction may be carried out at a temperature ranging from ice-cooling to reflux-heating. The reaction time can be varied, depending on a reagent and a reaction temperature, etc., and is usually 0.5 to 24 hours. Preferably, the reaction is carried out at a temperature ranging from ice-cooling to 50° C. in the presence of sodium borohydride or sodium cyanoborohydride in the solvent such as alcohols for 1 to 5 hours.

In the hydrogenation, the reaction is usually carried out in the presence of a catalyst. Catalysts which can be used include the hydrogenation catalysts such as palladium-carbon, platinum oxide, palladium hydroxide and the like. Solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; organic acid esters such as methyl acetate, ethyl acetate and the like; organic acids such as acetic acid and the like; and the mixtures thereof.

This reaction is carried out by using hydrogen gas at atmospheric pressure or at medium to high pressure, preferably using hydrogen gas at 1–5 $kg/cm^2$. The reaction time can be varied, depending on a reagent and a reaction temperature etc., and is usually 0.5 to 24 hours. Preferably, this reaction is carried out using platinum oxide as a catalyst under hydrogen gas of atmospheric pressure at a temperature of 0 to 50° C. in an alcohol solvent such as methanol or ethanol for 0.5 to 12 hours.

The above Step A and Step B may be optionally carried out in the same vessel. More specifically, the compound of formula (IV) and the compound of formula (V) are reacted by catalytic hydrogenation in a solvent to give the compound of formula (VII). Catalysts which can be used include the hydrogenation catalysts such as palladium-carbon, platinum oxide, palladium hydroxide and the like.

Solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; organic acid esters such as methyl acetate, ethyl acetate and the like; organic acids such as acetic acid and the like; and the mixtures thereof.

The reaction is carried out by using hydrogen gas at atmospheric pressure or at medium to high pressure, preferably using hydrogen gas at 1–5 $kg/cm^2$. Preferably, this reaction is carried out by using platinum oxide as a catalyst under hydrogen gas of atmospheric pressure at 0 to 50° C. in the presence of acetic acid in alcohols, in particular methanol or ethanol for 3 to 12 hours.

(b) 1,4-Benzodioxin derivative represented by formula (X)

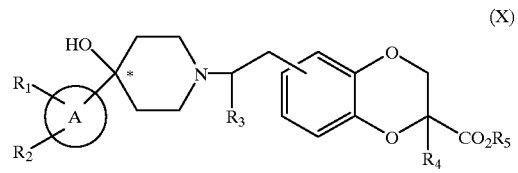

may be prepared by reacting a compound of formula (X)

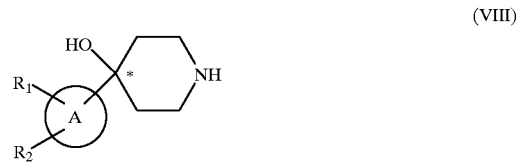

wherein A, R1 and R2 are as defined for formula (I) with the compound of formula (V)

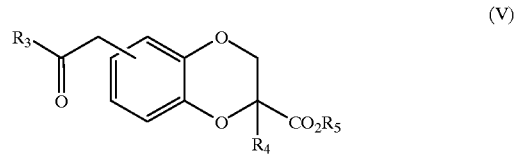

wherein $R_3$, $R_4$ and $R_5$ are as defined for formula (I) to prepare a compound of formula (I)

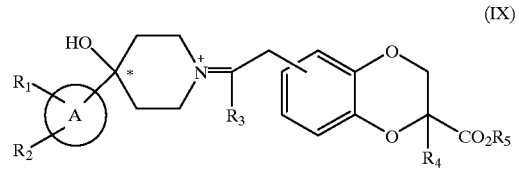

(Step C), followed by reducing the compound of formula (IX) (Step D).

Step C is the step of preparing the compound of formula (IX), and is usually carried out in the presence of a solvent. The reaction may be carried out while removing a resulting water with Dean-Stark apparatus, etc., or in the presence of a dehydrating agent such as anhydrous sodium carbonate, anhydrous potassium carbonate, anhydrous sodium sulfate, anhydrous calcium chloride, anhydrous magnesium sulfate, molecular sieves and the like.

This reaction is usually carried out in the presence of a solvent. The solvents employed are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; and the mixtures thereof.

The reaction may be carried out at a temperature ranging from ice-cooling to reflux-heating. The reaction time can be varied, depending on a reagent and a reaction temperature, etc., and is usually 0.5 to 12 hours. The reaction is preferably carried out under reflux-heating in the solvent such as hydrocarbons or alcohols for 1 to 5 hours. More preferably, the reaction is carried out by dehydration under reflux-heating in benzene for 1 to 3 hours.

Step D is the step of reducing the compound of formula (IX) to prepare the compound of formula (X). The reaction is usually carried out in the presence of a reducing agent or by hydrogenation in the presence of a catalyst. The reducing agents which can be used are metal hydrides such as lithium borohydride, sodium borohydride, sodium cyanoborohydride, lithium aluminum hydride, diisobutyl aluminum hydride and the like.

This reaction is usually carried out in the presence of a solvent. The solvents used are not specifically limited, unless giving any influence on the reaction, which can include ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; water; and the mixtures thereof.

The reaction may be carried out at a temperature ranging from ice-cooling to reflux-heating. The reaction time can be varied, depending on a reagent and a reaction temperature, etc., and is usually 0.5 to 12 hours. Preferably, the reaction is carried out at a temperature ranging from ice-cooling to 50° C. in the presence of sodium borohydride or sodium cyanoborohydride in alcohols for 1 to 5 hours.

In the hydrogenation, the reaction is usually carried out in the presence of a catalyst. The catalysts which can be used include the hydrogenation catalysts such as palladium-carbon, platinum oxide, palladium hydroxide and the like. The solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; organic acid esters such as methyl acetate, ethyl acetate and the like; organic acids such as acetic acid and the like; and the mixtures thereof.

This reaction is carried out by using hydrogen gas at atmospheric pressure or at medium to high pressure, preferably using hydrogen gas at 1–5 kg/cm$^2$. The reaction time can be varied, depending on a reagent and a reaction temperature, etc., and is usually 0.5 to 12 hours. Preferably, the reaction is carried out by using platinum oxide as a catalyst under hydrogen gas of atmospheric pressure at 0 to 50° C. in alcohols, in particular methanol or ethanol for 0.5 to 6 hours.

The reactions in the above Step C and Step D may be optionally carried out in the same vessel. More specifically, the compound of formula (V) and the compound of formula (VIII) are reacted by the catalytic hydrogenation in a solvent to give the compound of formula (X). The catalysts which can be used include the hydrogenation catalysts such as palladium-carbon, platinum oxide, palladium hydroxide and the like. The solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; organic acid esters such as methyl acetate, ethyl acetate and the like; organic acids such as acetic acid and the like; and the mixtures thereof.

This reaction is carried out by using hydrogen gas at atmospheric pressure or at medium to high pressure, preferably using hydrogen gas at 1–5 kg/cm$^2$. Preferably, the reaction is carried out by using platinum oxide as a catalyst under hydrogen gas of atmospheric pressure in the presence of acetic acid at 0 to 50° C. in alcohols, in particular methanol or ethanol for 3 to 12 hours.

(c) 1,4-Benzodioxin derivative represented by formula (XIII)

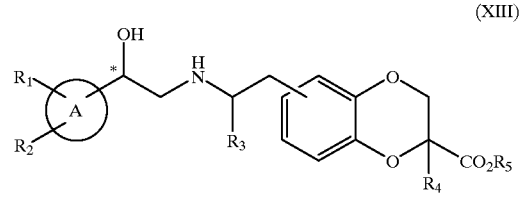

may be prepared by reacting a compound of formula (XI)

wherein A, R1, and R2 are as defined for formula (I) with a compound of formula (XII)

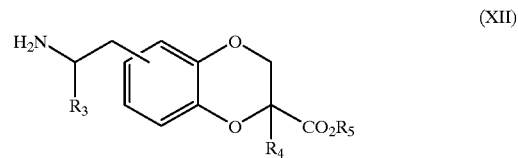

wherein $R_3$, $R_4$ and $R_5$ are as defined for formula (I).

This reaction is usually carried out in a solvent in the presence or absence of inorganic bases such as sodium carbonate, potassium carbonate, sodium hydrogencarbonate and the like; tertiary amines such as triethylamine, diisopropylethylamine and the like; and pyridines such as pyridine, 4-dimethylaminopyridine and the like. The reaction is preferably carried out in the presence of a silylating agent such as trimethylsilylacetamide, chlorotrimethylsilane and the like.

The solvents employed are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; pyridine; and the mixtures thereof.

The reaction may be carried out at a temperature ranging from ice-cooling to reflux-heating. The reaction time can be varied, depending on a reagent and a reaction temperature, etc., and is usually 0.5 to 24 hours. Preferably, the reaction is carried out at 20 to 100° C. in the presence of trimethylsilylacetamide in dimethyl sulfoxide for 6 to 24 hours.

(d) 1,4-Benzodioxin derivative represented by formula (XIII)

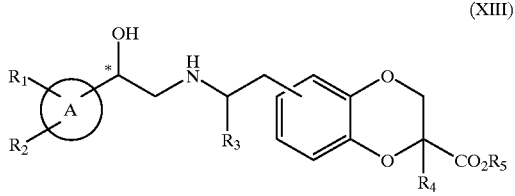

(XIII)

may be prepared by reacting a compound of formula (XIV)

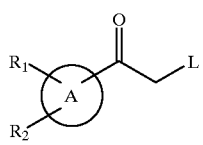

(XIV)

wherein A, $R_1$, and $R_2$ are as defined for formula (I), L is a leaving group such as chlorine, bromine, iodine, sulfonic acid ester and the like with a compound of formula (XII)

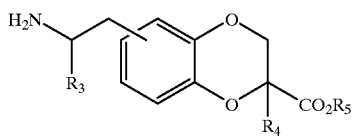

(XII)

wherein $R_3$, $R_4$ and $R_5$ are as defined for formula (I) to prepare a compound of formula (XV)

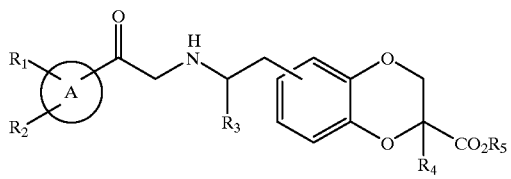

(XV)

(Step E), followed by reducing the compound of formula (XV) (Step F).

Step E is the step of preparing the compound of formula (XV), and is usually carried out in the presence or absence of inorganic bases such as sodium carbonate, potassium carbonate, sodium hydrogencarbonate and the like; tertiary amines such as triethylamine, diisopropylethylamine and the like; and pyridines such as pyridine, 4-dimethylaminopyridine and the like. The reaction is preferably carried out in the presence of a silylating agent such as trimethylsilylacetamide, chlorotrimethylsilane and the like.

The solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; and the mixtures thereof.

The reaction may be carried out et a temperature broadly ranging from ice-cooling to reflux-heating. The reaction time can be varied, depending on a reagent and a reaction temperature, etc., and is usually 0.5 to 24 hours. This reaction is preferably carried out at 20 to 100° C. in the presence of trimethylsilylacetamide in sulfoxides particularly in dimethyl sulfoxide for 6 to 12 hours.

Step F is the step of reducing the compound of formula (XV) to prepare the compound of formula (XIII).

The reaction is usually carried out in the presence of a reducing agent. The reducing agents which can be used are metal hydrides such as lithium borohydride, sodium borohydride, sodium cyanoborohydride, lithium aluminum hydride, diisobutyl aluminum hydride and the like. The reaction is usually carried out in the presence of a solvent The solvents used are not specifically limited, unless giving any influence on the reaction, which can include ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; water; and the mixtures thereof.

The reaction may be carried out at a temperature ranging from ice-cooling to reflux-heating. The reaction time can be varied, depending on a reagent and a reaction temperature, etc., and is usually 0.5 to 12 hours. Preferably, the reaction is carried out at a temperature ranging from ice-cooling to 50° C. in the presence of sodium borohydride or sodium cyanoborohydride in alcohols for 0.5 to 5 hours.

The compound of formula (IV) wherein n is 1 is commercially available, or can be prepared by various conventional processes, for example, the process shown below.

A compound of formula (XVIII')

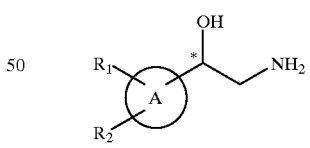

(XVIII')

wherein A, $R_1$ and $R_2$ are as defined for formula (I) may be prepared by reacting a compound of formula (XVI')

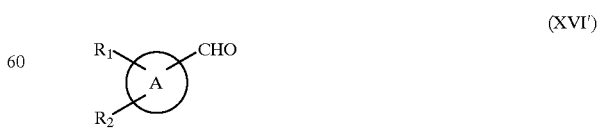

(XVI')

wherein A, $R_1$ and $R_2$ are as defined for formula (I) with a cyanogenating agent to prepare a compound of formula (XVII')

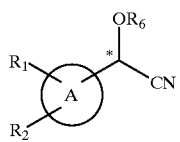

(XVII')

wherein A, $R_1$ and $R_2$ are as defined for formula (I) and $R_6$ is a hydrogen atom or a trimethylsilyl group (Step G), followed by reducing the compound of formula (XVII') (Step H).

Step G is the step of preparing the compound of formula (XVII'), and is usually carried out in the presence of a cyanogenating agent. The cyanogenating agents which can be used include trimethylsilylnitrile, hydrogen cyanide, sodium cyanide, potassium cyanide and the like. This reaction is usually carried out in the presence or absence of a Lewis acid catalyst, for example, a metal halide such as zinc iodide, aluminum chloride, titanium tetrachloride and the like; alkyl-metal halide such as diethylaluminum chloride, ethylaluminum dichloride and the like.

The solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; halogenated hydrocarbons such as chloroform, methylene chloride, carbon tetrachloride, 1,2-dichloroethylene and the like; amides such as dimethylformamide, dimethylacetamide, hexamethylphosphoric triamide and the like; alcohols such as methanol, ethanol, isopropanol and the like: sulfoxides such as dimethylsulfoxide and the like; water; and the mixtures thereof.

The reaction may be carried out at a temperature ranging from ice-cooling to reflux-heating. The reaction time can be varied, depending on a reagent and a reaction temperature, etc., and is usually 0.5 to 6 hours. The reaction is preferably carried out at a temperature ranging from ice-cooling to 50° C. in the presence of a catalytic amount of zinc iodide and trimethylsilylnitrile in halogenated hydrocarbons, in particular methylene chloride for 1 to 3 hours.

Step H is the step of reducing the compound of formula (XVII') to prepare the compound of formula (XVIII'). The reaction is usually carried out in the presence of a reducing agent. Reducing agents which can be used are metal hydrides such as lithium borohydride, sodium borohydride, sodium cyanoborohydride, lithium aluminum hydride, diisobutyl aluminum hydride and the like. The reaction is usually carried out in the presence of a solvent. The solvents used are not specifically limited, unless giving any influence on the reaction, which can include ethers such as diethyl ether, diisopropyl ether, tetrahydrofuran, dioxane and the like; alcohols such as methanol, ethanol, isopropanol and the like; and the mixtures thereof.

The reaction may be carried out at a temperature ranging from ice-cooling to reflux-heating. The reaction time can be varied, depending on a reagent and a reaction temperature, etc., and is usually 0.5 to 12 hours. Preferably, this reaction is carried out at a temperature ranging from 20° C. to reflux-heating in the presence of lithium aluminum hydride in ethers, in particular tetrahydrofuran for 1 to 5 hours.

A compound of formula (IV) wherein n is 2 can be prepared by various conventional processes, for example, the process shown below.

A compound of formula (XX)

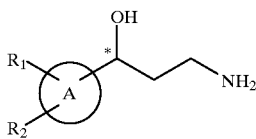

(XX)

wherein A, $R_1$ and $R_2$ are as defined for formula (I) may be prepared by reducing a compound of formula (XIX)

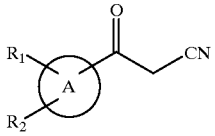

(XIX)

wherein A, $R_1$ and $R_2$ are as defined for formula (I).

The reaction is usually carried out in the presence of a reducing agent. The reducing agents which can be used are metal hydrides such as lithium borohydride, sodium borohydride, sodium cyanoborohydride, lithium aluminum hydride, diisobutyl aluminum hydride and the like. The reaction is usually carried out in the presence of a solvent. Solvents used are not specifically limited, unless giving any influence on the reaction, which can include ethers such as diethyl ether, diisopropyl ether, tetrahydrofuran, dioxane and the like; alcohols such as methanol, ethanol, isopropanol and the like; and the mixtures thereof.

The reaction may be carried out at a temperature broadly ranging from ice-cooling to reflux-heating. The reaction time can be varied, depending on a reagent and a reaction temperature, etc., and is usually 0.5 to 12 hours. Preferably, this reaction is carried out at a temperature ranging from 20° C. to reflux-heating in the presence of lithium aluminum hydride in ethers, in particular tetrahydrofuran for 1 to 5 hours.

The compound of formula (V) can be prepared by various conventional processes, for example, the process shown below.

The compound of formula (V)

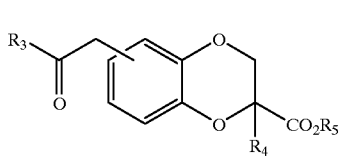

(V)

wherein $R_3$, $R_4$, and $R_5$ are as defined for formula (I) may be prepared by reacting a compound of formula (XXI)

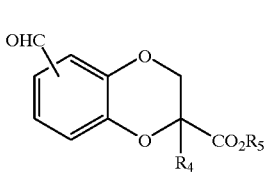

(XXI)

wherein $R_4$ and $R_5$ are as defined for formula (I) with a compound of formula (XXII)

$R_7NH_2$ (XXII)

wherein $R_7$ is a $(C_1$–$C_6)$alkyl group or a $(C_3$–$C_8)$cycloalkyl group to prepare a compound of formula (XXIII)

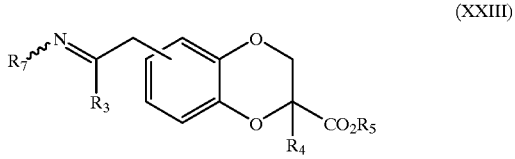

wherein $R_3$, $R_4$ and $R_5$ are as defined for formula (I) and $R_7$ is as defined for formula (XXII) (Step I), followed by reacting the compound of formula (XXIII) with a compound of formula (XXIV)

wherein $R_3$ is as defined for formula (I) to prepare a compound of formula (XXV)

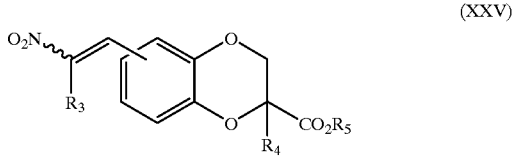

wherein $R_3$, $R_4$ and $R_5$ are as defined for formula (I) (Step J), followed by reducing and hydrating the compound of formula (XXV) (Step K).

Step I is the step of preparing the compound of formula (XXIII), and is usually carried out in the presence of a primary amine represented by formula (XXII) in the presence or absence of a solvent. The reaction may be carried out while removing a resulting water with Dean-Stark apparatus, etc., or in the presence of a dehydrating agent such as anhydrous sodium carbonate, anhydrous potassium carbonate, anhydrous sodium sulfate, anhydrous calcium chloride, anhydrous magnesium sulfate or molecular sieves. Preferably, the reaction is carried out in the presence of a solvent.

Amines represented by formula (XXII) include methylamine, ethylamine, butylamine, cyclohexylamine and the like. The solvents employed are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; and the mixtures thereof.

The reaction may be carried out at a temperature ranging from ice-cooling to reflux-heating. The reaction time can be varied, depending on a reagent and a reaction temperature, etc., and is usually 0.5 to 12 hours. The reaction is preferably carried out under reflux-heating in hydrocarbons for 1 to 5 hours. More preferably, the reaction is carried out by dehydrating under reflux-heating in benzene for 1 to 3 hours.

Step J is the step of preparing the compound of formula (XXV), and is usually carried out in the presence of an acid in the presence or absence of a solvent. The acids which can be used include inorganic acids such as hydrochloric acid, sulfuric acid and the like; organic acids such as acetic acid, propionic acid, pivalic acid and the like; sulfonic acids such as methanesulfonic acid, toluenesulfonic acid, camphorsulfonic acid and the like. The solvents employed are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; organic acids such as acetic acid, propionic acid and the like; and the mixtures thereof.

The compounds represented by formula (XXIV) include nitromethane, nitroethane, 1-nitrobutane, 1-nitropropane, 1-nitropentane, 1-nitrohexane and the like.

The reaction may be carried out at a temperature ranging from ice-cooling to reflux-heating. The reaction time can be varied, depending on a reagent and a reaction temperature, etc., and is usually 3 to 12 hours. The reaction is preferably carried out under reflux-heating in the organic acids, in particular acetic acid for 1 to 5 hours.

Step K is the step of preparing the compound of formula (V), and is usually carried out in the presence of a reducing agent. Reducing agents which can be used include reducing metal such as iron powder, zinc powder, copper powder and the like; tin chloride and the like. This reaction is preferably carried out in the presence of a solvent. The solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; organic acids such as acetic acid, propionic acid and the like; water; or the mixtures thereof.

The reaction may be carried out at a temperature ranging from ice-cooling to reflux-heating. The reaction time can be varied, depending on a reagent and a reaction temperature, etc., but is usually 1 to 6 hours. The reaction is preferably carried out under reflux-heating in the presence of iron powder in a mixed solvent of alcohols, organic acids and water, in particular a mixed solvent of methanol, acetic acid and water for 1 to 5 hours.

The compounds of formula (XXI) may be prepared according to the method disclosed by Durham et al in U.S. Pat. No. 4,205,079. In this case, the compounds of formula (XXI) are prepared as a mixture of regioisomers of an aldehyde group and they can be separated according to the following method.

A compound represented by formula (XXVII)

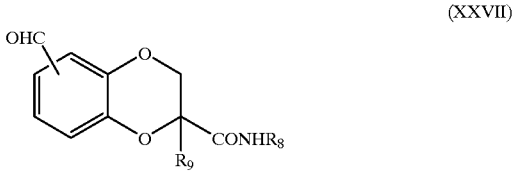

wherein $R_9$ represents a hydrogen atom or —$CONHR_8$ and $R_8$ is as defined for formula (XXVI) is prepared by reacting the compound of formula (XXI) with a compound of formula (XXVI)

$$R_8—NH_2 \quad (XXVI)$$

wherein $R_8$ is a hydrogen atom, a $C_1$–$C_6$ alkyl group, a phenyl group, a benzyl group or a phenethyl group.

This reaction is usually carried out by using 1–20 molar equivalent of the compound of formula (XXVI) in the presence or absence of a solvent while removing a resulting alcohol or water.

The compounds of formula (XXVI) can include ammonia, methylamine, ethylamine, butylamine, hexylamine, benzylamine, phenethylamine, aniline and the like.

The solvents employed are not specifically limited, unless giving any influence on the reaction, which can include hydrocarbons such as benzene, toluene, xylene, hexane, heptane and the like; ethers such is diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; and the mixtures thereof.

The reaction may be carried out at a temperature ranging from ice-cooling to reflux-heating. The reaction time can be varied, depending on a reagent and a reaction temperature, etc., and is usually 1 to 24 hours. The reaction is preferably carried out by using Dean-Stark apparatus under reflux-heating in the presence of phenethylamine in the hydrocarbons, in particular xylene for 3 to 6 hours.

The resultant compound of formula (XXVII) can be separated into individual regioisomers according to separation and purification methods such as silica gel column chromatography, fractional recrystallization or the like.

The compound of formula (XXVII) can be converted into the compound of formula (XXI) according to the following method.

The compound of formula (XXI)

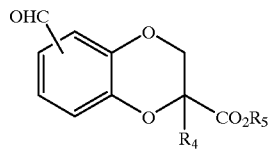

(XXI)

wherein $R_4$ is as defined for formula (I) and $R_5$ is a $C_1$–$C_6$ alkyl group can be prepared by hydrolysis of the compound of formula (XXVII) to give a compound of formula (XXVIII)

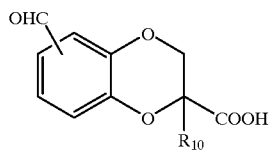

(XXVIII)

wherein $R_{10}$ is a hydrogen atom or a carboxy group (Step L), followed by esterification (Step M).

Step L is the step of preparing the compound of formula (XXVIII), and is usually carried out in the presence of an acid or a base. In case of reacting under acidic conditions, acids which can be used include inorganic acids such as hydrochloric acid, sulfuric acid, phosphoric acid, nitric acid and the like; organic acids such as acetic acid, propionic acid and the like; sulfonic acids such as methanesulfonic acid, toluenesulfonic acid, camphorsulfonic acid and the like; and the mixtures thereof. In case of reacting under basic conditions, bases which can be used include hydroxides such as sodium hydroxide, potassium hydroxide, lithium hydroxide and the like; carbonates such as potassium carbonate, sodium carbonate and the like; and the mixtures thereof.

The reaction is usually carried out in a solvent. The solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; organic acids such as acetic acid, propionic acid and the like; water; and the mixtures thereof.

The reaction may be carried out at a temperature ranging from ice-cooling to reflux-heating. The reaction time can be varied, depending on a reagent and a reaction temperature, etc., and is usually 3 to 24 hours. This reaction is preferably carried out under reflux-heating in the presence of hydrochloric acid or sulfuric acid in the mixed solvent of acetic acid and water for 6 to 12 hours. The compound of formula (XXVIII) is the compound of formula (XXI) wherein $R_5$ is a hydrogen atom.

Step M is the step of preparing the compound of formula (XXI) wherein $R_5$ is a $C_1$–$C_6$ alkyl croup. This reaction is carried out by using a $C_1$–$C_6$ alkanol under acidic conditions or by using a $C_1$–$C_6$ alkyl halide under basic conditions or by using a $C_1$–$C_6$ diazoalkane under acidic or neutral conditions.

In case of using the $C_1$–$C_6$ alkanol under acidic conditions, acids which can be used include inorganic acids such as hydrochloric acid, sulfuric acid and the like; organic acids such as acetic acid, propionic acid and the like; sulfonic acids such as methanesulfonic acid, toluenesulfonic acid, camphorsulfonic acid and the like; and the mixtures thereof. The $C_1$–$C_6$ alkanol employed can include methanol, ethanol, propanol, isopropanol, butanol, hexanol and the like. This reaction is preferably carried out in a solvent or by using the reactant $C_1$–$C_6$ alkanol itself as a solvent. Solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; and the mixtures thereof. The reaction may be carried out at a temperature ranging from ice-cooling to reflux-heating. The reaction time can be varied, depending on a reagent and a reaction temperature, etc., and is usually 1 to 6 hours. The reaction is preferably carried out under reflux-heating in the presence of sulfuric acid in hydrocarbons, in particular benzene for 1 to 2 hours while removing a resulting water.

In case of using the $C_1$–$C_6$ alkyl halide under basic conditions, bases which can be used include carbonates such as potassium carbonate, sodium carbonate and the like; hydroxides such as sodium hydroxide, potassium hydroxide, lithium hydroxide and the like; alkali metal hydrides such as sodium hydride, potassium hydride, calcium hydride and the like; and the mixtures thereof. The $C_1$–$C_6$ alkyl halides employed can include methyl iodide, ethyl iodide, propyl bromide, butyl bromide, hexyl bromide and the like.

This reaction is usually carried out in a solvent. The solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; sulforan; and the mixtures thereof. The reaction may be carried out at a temperature ranging from ice-cooling to reflux-heating. The reaction time can be varied, depending on a reagent and a reaction temperature, etc., and is usually 0.5 to 6 hours. This reaction is preferably carried out at a temperature ranging from ice-cooling to 25° C. in the presence of potassium carbonate in amides, in particular dimethylformamide for 0.5 to 3 hours.

In case of using the diazoalkane, the diazoalkanes which can be used include diazomethane, trimethylsilyl-diazomethane, diazoethane, diazopropane, diazohexane and the like. This reaction is usually carried out in a solvent. Solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; and the mixtures thereof. The reaction may be carried out at a temperature ranging from ice-cooling to 50° C. The reaction time can be varied, depending on a reagent and a reaction temperature, etc., and is usually 0.5 to 6 hours. The reaction is preferably carried out at a temperature ranging from ice-cooling to 25° C. in ethers, particularly diethyl ether for 0.5 to 3 hours.

The hydrolysis of an ester or an amide and the conversion of a carboxylic acid to an ester or an amide as described above are described in "Nobuo Izumiya, Tetsuo Kato, Haruhiko Aoyagi, Michinori Waki, Fundamentals and Experiment of Peptide Synthesis, Maruzene Company, 1985".

The compound of formula (XXVIII) wherein $R_{10}$ is a hydrogen atom can be also prepared by the following method.

The compound of formula (XXXII)

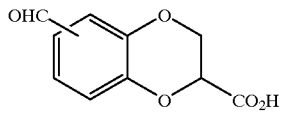
(XXXII)

can be prepared by reacting a compound of formula (XXIX)

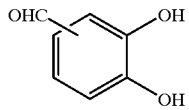
(XXIX)

with a compound of formula (XXX)

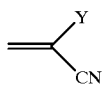
(XXX)

wherein Y is a halogen atom to give a compound of formula (XXXI) (Step N),

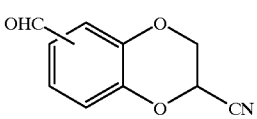
(XXXI)

followed by hydrolyzing the compound of formula (XXXI) (Step O).

Step N is the step of preparing the compound of formula (XXXI), and is usually carried out by using a base in a solvent. The bases can include carbonates such as potassium carbonate, sodium carbonate, sodium hydrogencarbonate and the like; hydroxides such as sodium hydroxide, potassium hydroxide, lithium hydroxide and the like; and the mixtures thereof. The solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; ketones such as acetone, methylethylketone and the like; and the mixtures thereof.

The reaction may be carried out at a temperature ranging from ice-cooling to reflux-heating. The reaction time can be varied, depending on a reagent and a reaction temperature, etc., and is usually 1 to 72 hours. This reaction is preferably carried out at a temperature ranging from 20° C. to reflux-heating in the presence of carbonates, in particular potassium carbonate in ketones, in particular acetone for 3 to 72 hours.

Step O is the step of preparing the compound of formula (XXXII), and is carried out by reacting the compound of formula (XXXI) with water in the presence of an acid or a base. In case of reacting under acidic conditions, the acids which can be used include inorganic acids such as hydrochloric acid, sulfuric acid, phosphoric acid, nitric acid and the like; organic acids such as acetic acid, propionic acid and the like; sulfonic acids such as methanesulfonic acid, toluenesulfonic acid, camphorsulfonic acid and the like; and the mixtures thereof. In case of reacting under basic conditions, the bases which can be used include hydroxides such as sodium hydroxide, potassium hydroxide, lithium hydroxide and the like; carbonates such as potassium carbonate, sodium carbonate and the like; and the mixtures thereof.

This reaction is usually carried out in water, or in water optionally mixed with other solvents. The solvents employed are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; organic acids such as acetic acid, propanoic acid and the like; and the mixtures thereof.

The reaction may be carried out at a temperature ranging-from ice-cooling to reflux-heating. The reaction time can be varied, depending on a reagent and a reaction temperature, etc., but is usually 3 to 24 hours. The reaction is preferably carried out under reflux-heating in the presence of hydrochloric acid or sulfuric acid in the mixed solvents of acetic acid and water for 6 to 12 hours.

Optical isomers of the 1,4-benzodioxin derivatives represented by formula (I) can be resolved optically by a fractional recrystallization using an optically active acid or base, or by a column chromatography having an optically active carrier. They can be also prepared by chiral synthetic methods. With regard to the separation of the above-mentioned optical isomers, the principle and utilization of the separation is described in "Separation of Optical Isomers, quarterly chemical review No.6, The Chemical Society of Japan, 1989".

The compounds represented by formula (XXXII)

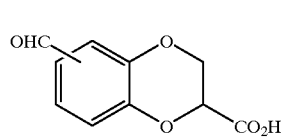
(XXXII)

can be resolved optically by the following method.

The compound represented by formula (XXXII)

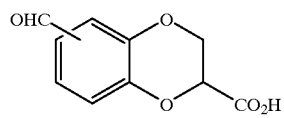
(XXXII)

is condensed with an optically active amine represented by formula (XXXIII)

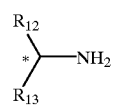
(XXXIII)

wherein $R_{12}$ is a phenyl group or a naphthyl group and $R_{13}$ is a $(C_1-C_4)$ alkyl group to give a compound represented by formula (XXXIV)

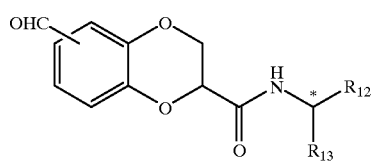
(XXXIV)

wherein $R_{12}$ and $R_{13}$ are as defined for formula (XXXIII) (Step P), and the diastereoisomers of formula (XXXIV) are separated by a fractional recrystallization or a column chromatography to give a compound represented by formula (XXXIVa)

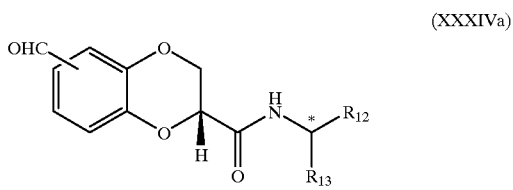
(XXXIVa)

wherein $R_{12}$ and $R_{13}$ are as defined for formula (XXXIII), and a compound represented by formula (XXXIVb)

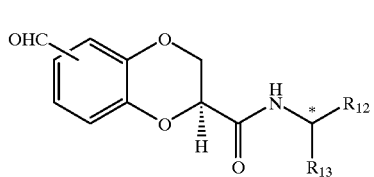
(XXXIVb)

wherein $R_{12}$ and $R_{13}$ are as defined for formula (XXXIII) (Step Q), and then the compounds of formulae (XXXIVa) and (XXXIVb) are respectively hydrolyzed to give the optically active compound of formula (XXXIIa)

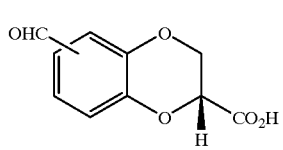
(XXXIIa)

from the compound of formula (XXXIVa) and the optically active compound of formula (XXXIIb)

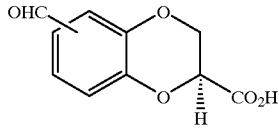
(XXXIIb)

from the compound of formula (XXXIVb) (Step R).

The compounds of formulae (XXXIIa) and (XXXIIb) are esterified according to the methods described in the above-mentioned Step M, and these esters are reacted according to the methods described in the above-mentioned Steps I–K to prepare a compound of formula (XXXVa)

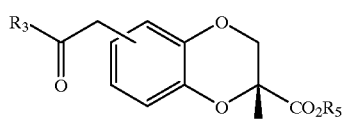
(XXXVa)

wherein $R_3$ and $R_5$ are as defined for formula (I) from the compound of formula (XXXIIa), and a compound of formula (XXXVb)

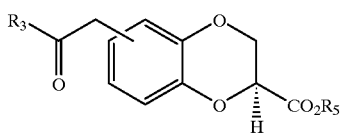

(XXXVb)

wherein $R_3$ and $R_5$ are as defined for formula (I) from the compound of formula (XXXIIb).

Step P is the step of preparing the compound of formula (XXXIV). This reaction is carried out by using 1–20 molar equivalents of the compound of formula (XXXIII) in the presence or absence of a solvent while removing a resulting water. The solvents employed in this reaction are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; and the mixtures thereof. Examples of the compounds represented by formula (XXXIII) can include (R)-(+)-1-phenylethylamine, (S)-(–)-1-phenylethylamine, (R)-(+)-1-(1-naphthyl)ethylamine, (S)-(–)-1-(1-naphthyl)ethylamine and the like, and (R)-(+)-1-phenylethylamine and (S)-(–)-1-phenylethylamine are preferable. The reaction can be occasionally carried out by using various condensing agents. Examples of the condensing agents can include carbodiimides such as 1,3-dicyclohexylcarbodiimide, 1-ethyl-3-(3'-dimethylaminopropyl)carbodiimide (WSCI), 1-ethyl-3-(3'-dimethylaminopropyl)carbodiimide hydrochloride (WSCI HCl) and the like, and 1-ethyl-3-(3'-dimethylaminopropyl)carbodiimide hydrochloride (WSCI HCl) is preferable. In case of using the condensing agent, the reaction can be occasionally carried out with various additives. Examples of the additives can include pyridines such as pyridine, 4-dimethylaminopyridine and the like, benzotriazoles such as 1-hydroxybenzotriazole (HOBt), 3,4-dihydroxy-3-hydroxy-4-oxo-1,2,3-benzotriazine (HOOBt) and the like, and 1-hydroxybenzotriazole (HOBt) is preferable. The reaction may be carried out at a temperature ranging from ice-cooling to reflux-heating. The reaction time can be varied, depending on a reagent and a reaction temperature, etc., and is usually 1 to 24 hours. The reaction is preferably carried out by using carbodiimides as a condensing agent and 4-dimethylaminopyridine or 1-hydroxybenzotriazole (HOBt) as an additive at a temperature ranging from ice-cooling to 50° C. in the presence of (R)-(+)-1-phenylethylamine or (S)-(–)-1-phenylethylamine in the solvent such as amides or halogenated hydrocarbons for 1 to 15 hours. The reaction is more preferably carried out by using 1-ethyl-3-(3'-dimethylaminopropyl)carbodiimide hydrochloride (WSCI HCl) as a condensing agent and 1-hydroxybenzotriazole (HOBt) as an additive at a temperature ranging from ice-cooling to 30° C. in the presence of (R)-(+)-1-phenylethylamine or (S)-(–)-1-phenylethylamine in dimethylformamide for 3 to 12 hours.

Step Q is the step of preparing the compounds of formulae (XXXIVa) and (XXXIVb) by separation and purification of the compound of formula (XXXIV), e.g., by a fractional recrystallization or a column chlomatography or both. In case of the fractional recrystallization, solvents employed therein are not specifically limited, unless giving any influence on the recrystallization, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; acetic acid esters such as ethyl acetate, methyl acetate and the like; and the mixtures thereof. The solvents preferably employed are acetic acid esters, alcohols, mixed solvents of acetic acid ester and hydrocarbons, and mixed solvents of alcohols and hydrocarbons. More preferably employed are ethyl acetate, mixed solvents of ethyl acetate and hexane (mixing ratio; 1:99–99:1, v/v), isopropanol or mixed solvents of isopropanol and hexane (mixing ratio; 1:99–99:1, v/v). Recrystallization temperature can be varied, depending on conditions of solvents, etc., and usually is ranging from ice-cooling to reflux-heating. The recrystallization is preferably carried out by dissolving in ethyl acetate or isopropanol, adding equal volumes of hexane and allowing to stand or stirring at 10 to 30° C.

In case of the column chromatography, column carriers used therein can include silica gel (crushed or spherical, particle diameter 5 μm–70 μm), and a mobile phase is not specifically limited, unless giving any influence on the separation, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; alcohols such as methanol, ethanol, isopropanol and the like; acetic acid esters such as ethyl acetate, methyl acetate and the like; and the mixtures thereof. The solvents as preferably employed are mixed solvents of acetic acid esters and hydrocarbones, in particular a mixed solvent of ethyl acetate and hexane. The column chromatography is preferably carried out by using silica gel (crushed, particle diameter 43 μm–63 μm) as a carrier and a mixed solvent of ethyl acetate and n-hexane (1:99–99:1) as a mobile phase at ordinary pressure to 50 kgf/cm².

Step R is the step of hydrolyzing the compound of formula (XXXIVa) or (XXXIVb). This reaction is carried out by reacting the compound with water in the presence of an acid or a base. In case of acidic conditions, the acids employed can include inorganic acids such as hydrochloric acid, sulfuric acid, phosphoric acid, nitric acid and the like; organic acids such as acetic acid, propionic acid and the like; sulfonic acids such as methanesulfonic acid, toluenesulfonic acid, camphorsulfonic acid and the like; and the mixtures thereof. In case of basic conditions, bases employed can include hydroxides such as sodium hydroxide, potassium hydroxide, lithium hydroxide and the like; carbonates such as potassium carbonate, sodium carbonate and the like; and the mixtures thereof. The reaction is usually carried out in a solvent. The solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; organic acids such as acetic acid, propionic acid and the like; water; and the mixtures thereof. The reaction may be carried out at a temperature ranging from ice-cooling to reflux-heating. The reaction time can be varied, depending on a reagent and a reaction temperature, etc., but is usually 12 to 48 hours. This reaction is preferably carried out under reflux-heating in the presence of hydrochloric acid or sulfuric acid in the mixed solvents of acetic acid and water for 24 to 36 hours.

In the compound represented by formula (XVIII'), the optically active compound represented by formula (XXXVI)

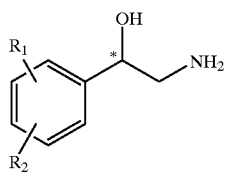

(XXXVI)

wherein $R_1$ and $R_2$ are as defined for formula (I) can be prepared by the following method.

A compound represented by formula (XXXVII)

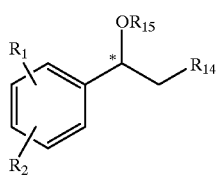

(XXXVII)

wherein $R_1$ and $R_2$ are as defined for formula (I), $R_{14}$ is a halogen atom, a $(C_1-C_6)$alkylsulfonyloxy group or an arylsulfonyloxy group which may be substituted by a $(C_1-C_4)$ alkyl group, and $R_{15}$ is a hydrogen atom or a $(C_1-C_6)$ alkoxymethyl group is reacted with a compound represented by formula (XXXVIII)

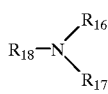

(XXXVIII)

wherein $R_{16}$ is a hydrogen atom, $R_{17}$ is a benzyl group which may be substituted by a $(C_1-C_6)$alkyl group or a $(C_1-C_6)$ alkoxy group, or $R_{16}$ and $R_{17}$ together form a phthaloyl group, and $R_{18}$ is a hydrogen atom or a potassium atom, or with a metal azide to prepare a compound represented by formula (XXXIX)

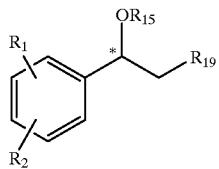

(XXXIX)

wherein $R_1$ and $R_2$ are as defined for formula (I), $R_{15}$ is as defined for formula (XXXVII) and $R_{19}$ is an azide group, a phthalimide group or a benzylamino group in which a benzyl moiety may be substituted by a $(C_1-C_6)$alkyl or a $(C_1-C_6)$alkoxy group (Step S).

When $R_{19}$ is an azide group or a benzylamino group in which a benzyl moiety may be substituted by a $(C_1-C_6)$alkyl or a $(C_1-C_6)$alkoxy group in formula (XXXIX), a compound represented by formula (XXXX)

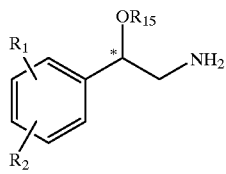

(XXXX)

wherein $R_1$ and $R_2$ are as defined for formula (I), and $R_{15}$ is as defined for formula (XXXVII) can be prepared by catalytic hydrogenation (Step T). When $R_{19}$ is a phthalimide group, the compound represented by formula (XXXX) can be prepared by hydrolysis or hydrazinolysis (Step U). The compound of formula (XXXX) wherein $R_{15}$ is a hydrogen atom is the compound represented by formula (XXXVI). When $R_{15}$ is a $(C_1-C_6)$alkoxymethyl group in formula (XXXX), the compound of formula (XXXVI) can be prepared by acidic hydrolysis (Step V).

Step S is the step of preparing the compound of formula (XXXIX) by reacting the compound of formula (XXXVII) with the compound of formula (XXXVIII) or by reacting the compound of formula (XXXVII) with metal azide. In case of reaction with the compound of formula (XXXVIII), the reaction is usually carried out in a solvent. The solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; water; pyridine; and the mixtures thereof. Examples of the compounds of formula (XXXVIII) include phthalimide, potassium phtalimide, benzylamine, 3-methoxybenzylamine, 4-methoxybenzylamine, 3,4-dimethoxybenzylamine, 3,5-dimethoxybenzylamine, 3,4,5-trimethoxybenzylamine, 4-methylbenzylamine and the like. The reaction may be occasionally carried out by adding bases. Bases employed can include carbonates such as potassium carbonate, sodium carbonate and the like; hydroxides such as sodium hydroxide, potassium hydroxide, lithium hydroxide and the like; alkali metal hydrides such as sodium hydride, potassium hydride, calcium hydride and the like; alkylamines such as triethylamine, diisopropylethylamine and the like; pyridines such as pyridine, 4-dimethylaminopyridine; and the mixtures thereof. The reaction may be carried out at a temperature ranging from ice-cooling to reflux-heating. The reaction time can be varied, depending on a reagent and a reaction temperature, etc., and is usually 1 to 24 hours. The reaction is preferably carried out by using potassium phthalimide or benzylamine as a compound of formula (XXXVIII) at 50 to 100° C. in dimethylformamide for 12 to 24 hours. In case of using metal azides, the reaction is usually carried out in a solvent. The solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; water; pyridine; and the mixtures thereof. Examples of the metal azides include sodium azide, potassium azide, lithium azide and the like. The reaction may be occasionally carried out by adding a base. Bases employed can include carbonates such as potassium carbonate, sodium carbonate and the like; hydroxides such as sodium hydroxide, potassium hydroxide, lithium hydroxide and the like; alkali metal hydrides such as sodium hydride, potassium hydride, calcium hydride and the like; alkylamines such as triethylamine, diisopropylethylamine and the like; pyridines such as pyridine, 4-dimethylaminopyridine; and the mixtures thereof. The reaction may be carried out at a temperature ranging from ice-cooling to reflux-heating. The reaction time can be varied, depending on a reagent and a reaction temperature, etc., but is usually 1 to 24 hours. The reaction is preferably carried out by using sodium azide at a temperature ranging from 100° C. to reflux-heating in dimethylformamide for 15 to 20 hours.

Step T is the step of preparing the compound of formula (XXXX), when $R_{19}$ is an azide group or a benzylamino group in the compound of formula (XXXIX), by catalytic hydrogenation. The reaction is usually carried out in the presence of a catalyst. The catalysts which can be used include the hydrogenation catalysts such as palladium-carbon, platinum oxide, palladium hydroxide and the like. The solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; organic acid esters such as methyl acetate, ethyl acetate and the like; organic acids such as acetic acid and the like; and the mixtures thereof. This reaction is carried out by using hydrogen gas at atmospheric pressure or at medium to high pressure, preferably using hydrogen gas at 1–5 kg/cm², or using formates as a hydrogen donor. The reaction is preferably carried out by using palladium-carbon as the catalyst at a temperature ranging from 50° C. to reflux-heating in the presence of ammonium formate in alcohols, in particular methanol or ethanol for 0.5 to 3 hours, or under hydrogen gas at atmospheric pressure at 10 to 30° C. in the presence of palladium-carbon in methanol or ethanol for 1 to 6 hours.

Step U is the step of preparing the compound of formula (XXXX) when $R_{19}$ is a phthalimide group in the compound of formula (XXXIX). This reaction is carried out by hydrolysis or hydrazinolysis. In case of hydrolysis, the reaction is usually carried out in water, occasionally by adding solvents. The solvents used are not specifically limited, unless giving any influence on the reaction, which can include ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; pyridine; and the mixtures thereof. The reaction may be usually carried out in the presence of a base. Bases employed can include carbonates such as potassium carbonate, sodium carbonate and the like; hydroxides such as sodium hydroxide, potassium hydroxide, lithium hydroxide and the like; and the mixtures thereof. The reaction may be carried out at a temperature ranging from ice-cooling to reflux-heating. The reaction time can be varied, depending on a reagent and a reaction temperature etc., but is usually 1 to 24 hours. This reaction is preferably carried out by using sodium hydroxide or potassium hydroxide as a base at a temperature ranging from 50° C. to reflux-heating in methanol or a mixed solvent of ethanol and water for 1 to 6 hours. In case of hydrazinolysis, the reaction is usually carried out by reacting with hydrazine in a solvent. Solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; water; pyridine; and the mixtures thereof. The reaction time can be varied, depending on a reagent and a reaction temperature, etc., and is usually 1 to 24 hours. This reaction is preferably carried out at a temperature ranging from 50° C. to reflux-heating in the presence of hydrazine in alcohols, in particular methanol, ethanol or a mixed solvent of alcohols and water for 0.5 to 3 hours.

Step V is the step of hydrolyzing the compound of formula (XXXX) wherein $R_{15}$ is a $(C_1-C_4)$ alkoxymethyl. This reaction is usually carried out in the presence of an acid in a solvent. Acids employed can include inorganic acids such as hydrochloric acid, sulfuric acid, nitric acid and the like; organic acids such as acetic acid, propionic acid, pivalic acid and the like; sulfonic acids such as methanesulfonic acid, toluenesulfonic acid, camphorsulfonic acid and the like. Solvents used are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene; ethers such as diethyl ether, diisopropyl ether, tetrahydrofuran, dioxane and the like; amides such as dimethylformamide, dimethylametamide, hexamethylphosphoric triamide and the like; alcohols such as methanol, ethanol, isopropanol and the like; sulfoxides such as dimethylsulfoxide and the like; sulforan; organic acid such as acetic acid, propionic acid and the like; water; and the mixtures thereof. The reaction may be carried out at a temperature ranging from ice-cooling to reflux-heating. The reaction time can be varied, depending on a reagent and a reaction temperature, etc., and is usually 3 to 12 hours. The reaction is preferably carried out by using hydrochloric acid as an acid at a temperature ranging from 50° C. to reflux-heating in alcohols, in particular a mixed solvent of methanol or ethanol and water for 1 to 6 hours.

The optically active compound represented by formula (XXXVII) can be also prepared by the following method.

A compound represented by formula (XXXX)

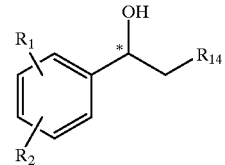

(XXXXII)

wherein $R_1$ and $R_2$ are as defined for formula (I), $R_{14}$ is as defined for formula (XXXVII) can be prepared by asymmetric reduction of the compound represented by formula (XXXXI)

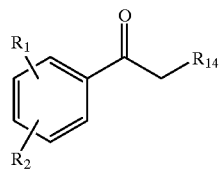

(XXXXI)

wherein $R_1$ and $R_2$ are as defined for formula (I), $R_{14}$ is as defined for formula (XXXVII) according to the methods described in J. Org. Chem., Vol. 53, 2861, 1988. The compound of formula (XXXXII) is the compound of formula (XXXVII) wherein $R_{15}$ is a hydrogen atom. Further, the compound of formula (XXXXII) is reacted with a compound of formula (XXXXIII)

$$R_{20}Z \quad \text{(XXXXIII)}$$

wherein $R_{20}$ is a $(C_1-C_4)$alkoxymethyl group and Z is a halogen atom to give the compound of formula (XXXVII) wherein $R_{15}$ is a $(C_1-C_6)$alkoxymethyl group (Step W).

Step W is the step of reacting the compound of formula (XXXXII) with the compound of formula (XXXXIII). This reaction is usually carried out in a solvent. The solvents used are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; sulforan; and the mixtures thereof. Examples of the compounds of formula (XXXXIII) include chloromethyl methyl ether, bromomethyl methyl ether, chloromethyl ethyl ether, bromomethyl ethyl ether, chloromethyl t-butyl ether, bromomethyl t-butyl ether and the like. The reaction is usually carried out in the presence of a base. Bases employed can include carbonates such as potassium carbonate, sodium carbonate and the like; hydroxides such as sodium hydroxide, potassium hydroxide, lithium hydroxide and the like; alkali metals hydride such as sodium hydride, potassium hydride, calcium hydride and the like; alkylamines such as triethylamine, N,N-diisopropylethylamine and the like; pyridines such as pyridine, 4-dimethylaminopyridine; and the mixtures thereof. The reaction may be carried out at a temperature ranging from ice-cooling to reflux-heating. The reaction time can be varied, depending on a reagent and a reaction temperature, etc., and is usually 1 to 24 hours. This reaction is preferably carried out by using chloromethyl methyl ether under reflux-heating in the presence of N,N-diisopropylethylamine and 4-dimethylaminopyridine in halogenated hydrocarbons, in particular methylene chloride for 12 to 24 hours.

The compound represented by formula (XXXXII) wherein $R_{14}$ is a $(C_1-C_6)$alkylsulfonyloxy group or an arylsulfonyloxy group which may be substituted by a $(C_1-C_4)$alkyl group can be also prepared by the following method.

The above-mentioned compound can be prepared by reducing an optically active mandelic acid derivative represented by formula (XXXXIV)

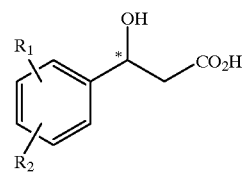

(XXXXIV)

wherein $R_1$ and $R_2$ are as defined for formula (I) to give a compound represented by formula (XXXXV)

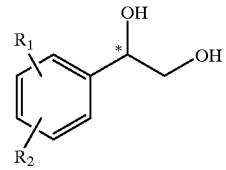

(XXXXV)

wherein $R_1$ and $R_2$ are as defined for formula (I) (Step X), followed by reacting it with a compound represented by formula (XXXXVI)

$$R_{21}SO_2Cl \quad \text{(XXXXVI)}$$

wherein $R_{21}$ is a $(C_1-C_6)$alkyl group or an aryl group which may be substituted by a $(C_1-C_4)$alkyl group (Step Y).

Step X is the step of reducing the compound of formula (XXXXIV). This reaction is usually carried out in the presence of a reducing agent. Reducing agents which can be used include metal hydrides such as lithium borohydride, sodium borohydride, sodium cyanoborohydride, lithium aluminum hydride, diisobutyl aluminum hydride and the like. The reaction is usually carried out in the presence of a solvent. The solvents used are not specifically limited, unless giving any influence on the reaction, which can include ethers such as diethyl ether, diisopropyl ether, tetrahydrofuran, dioxane and the like; halogenated hydrocarbons such as chloroform, methylene chloride, carbon tetrachloride, 1,2-dichloroethylene and the like; alcohols such as methanol, ethanol, isopropanol and the like; and the mixtures thereof. The reaction may be carried out at a temperature ranging from ice-cooling to reflux-heating. The reaction time can be varied, depending on a reagent and a reaction temperature, etc., and is usually 0.5 to 12 hours. Preferably, this reaction is carried out at a temperature ranging from 20° C. to reflux-heating in the presence of lithium aluminum hydride or borane in ethers, in particular tetrahydrofuran for 1 to 5 hours.

Step Y is the step of reacting the compound of formula (XXXXV) with the compound of formula (XXXXVI). This reaction is usually carried out in the presence of a solvent. Solvents used are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; sulforan; and the mixtures thereof.

Examples of the compounds of formula (XXXXVI) include methanesulfonyl chloride, ethanesulfonyl chloride, benzenesulfonyl chloride, p-toluenesulfonyl chloride, 1-naphthalenesulfonyl chloride, 2-naphthalenesulfonyl chloride and the like. The reaction is usually carried out in the presence of a base. Bases employed can include carbonates such as potassium carbonate, sodium carbonate and the like; hydroxides such as sodium hydroxide, potassium hydroxide, lithium hydroxide and the like; alkali metal hydrides such as sodium hydride, potassium hydride, calcium hydride and the like; alkylamines such as triethylamine, N,N-diisopropylethylamine and the like; pyridines such as pyridine, 4-dimethylaminopyridine and the like; and the mixtures thereof. The reaction may be carried out at a temperature ranging from ice-cooling to reflux-heating. The reaction time can be varied, depending on a reagent and a reaction temperature, etc., and is usually 1 to 24 hours. The reaction is preferably carried out by using methanesulfonyl chloride or p-toluenesulfonyl chloride at 0 to 50° C. in the presence of alkylamines in halogenated hydrocarbones or ethers for 1 to 12 hours. More preferably, the reaction is carried out by using methanesulfonyl chloride at 0 to 40° C. in the presence of triethylamine in tetrahydrofuran for 1 to 3 hours.

The compound of formula (XXXIX) wherein $R_{15}$ is a hydrogen atom and $R_{19}$ is a benzylamino group, of which the benzyl moiety may be substituted by a $(C_1-C_6)$alkyl group or a $(C_1-C_6)$alkoxy group can be also prepared by the following method ($\alpha$) or ($\beta$).

Method ($\alpha$)

The above compound can be prepared by reacting the compound of formula (XXXXIV) with a compound of formula (XXXXVII)

$$R_{22}NH_2 \qquad (XXXXVII)$$

wherein $R_{22}$ is a benzyl group which may be substituted by a $(C_1-C_6)$alkyl group or $(C_1-C_6)$alkoxy group to prepare a compound of formula (XXXXVIII)

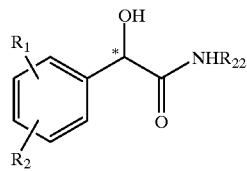
(XXXXVIII)

wherein $R_1$ and $R_2$ are as defined for formula (I) and $R_{22}$ is as defined for formula (XXXXVII) (Step Z), followed by reducing (Step A').

Step Z is the step of condensing the compound of formula (XXXXIV) with the compound of formula (XXXXVII). This reaction is usually carried out by using 1–20 molar equivalent of the compound of formula (XXXXVII) in the presence or absence of a solvent while removing a resulting water. Solvents used are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; and the mixtures thereof. Examples of the compounds of formula (XXXXVII) include benzylamine, 3-methoxybenzylamine, 4-methoxybenzylamine, 3,4-dimethoxybenzylamine, 3,5-dimethoxybenzylamine, 3,4,5-trimethoxybenzylamine, 4-methylbenzylamine and the like, benzylamine being preferred. The reaction can be occasionally carried out by adding various condensing agents. Examples of the condensing agents can include carbodiimides such as 1,3-dicyclohexylcarbodiimide, 1-ethyl-3-(3'-dimethylaminopropyl)carbodiimide (WSCI), 1-ethyl-3-(3'-dimethylaminopropyl)carbodiimide hydrochloride (WSCI HCl) and the like, 1-ethyl-3-(3'-dimethylaminopropyl)carbodiimide hydrochloride (WSCI HCl) being preferable. In case of using condensing agents, the reaction can be occasionally carried out with various additives. Examples of the additives can include pyridines such as pyridine, 4-dimethylaminopyridine and the like, benzotriazoles such as 1-hydroxybenzotriazole (HOBt) and the like, and 3,4-dihydroxy-3-hydroxy-4-oxo-1,2,3-benzotriazine (HOOBt), 1-hydroxybenzotriazole (HOBt) being preferable. The reaction may be carried out at a temperature ranging from ice-cooling to reflux-heating. The reaction time can be varied, depending on a reagent and a reaction temperature, etc., and is usually 1 to 24 hours. The reaction is preferably carried out by using carbodiimides as a condensing agent and 4-dimethylaminopyridine or 1-hydroxybenzotriazole (HOBt) as an additive at a temperature ranging from ice-cooling to 50° C. in the presence of benzylamine in amides or halogenated hydrocarbons for 1 to 15 hours. The reaction is more preferably carried out by using 1-ethyl-3-(3'-dimethylaminopropyl)carbodiimide hydrochloride (WSCI HCl) or 1,3-dicyclohexylcarbodiimide as a condensing agent and 1-hydroxybenzotriazole (HOBt) as an additive at 50 to 120° C. in the presence of benzylamine in dimethylformamide for 1 to 5 hours.

Step A' is the step of reducing the compound of formula (XXXXVIII). This reaction is usually carried out in the presence of a reducing agent. Reducing agents which can be used include metal hydrides such as lithium aluminum hydride, diisobutyl aluminum hydride, borane and the like. This reaction is usually carried out in the presence of a solvent. The solvents used are not specifically limited, unless giving any influence on the reaction, which can include ethers such as diethyl ether, diisopropyl ether, tetrahydrofuran, dioxane and the like; alcohols such as methanol, ethanol, isopropanol and the like; and the mixtures thereof. The reaction may be carried out at a temperature ranging from ice-cooling to reflux-heating. The reaction time can be varied, depending on a reagent and a reaction temperature, etc., and is usually 0.5 to 12 hours. Preferably, this reaction is carried out at a temperature ranging from 50° C. to reflux-heating in the presence of lithium aluminum hydride in ethers, in particular tetrahydrofuran for 1 to 5 hours.

Method ($\beta$)

The above-mentioned compound of formula (XXXIX) wherein $R_{15}$ is a hydrogen atom and $R_{19}$ is a benzylamino group can be prepared by reacting a compound of formula (XXXXIX)

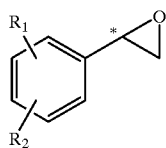
(XXXXIX)

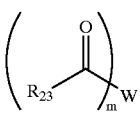
(XXXXXI)

wherein $R_1$ and $R_2$ are as defined for formula (I) with the compound of formula (XXXXVII). The compound represented by formula (XXXXIX) is commercially available, or any enantiomer thereof can be prepared according to the methods described in J. Org. Chem., Vol. 53, 2861, (1988), or J. Med. Chem., Vol. 35, 3081, (1991).

This reaction is usually carried out in a solvent in the presence or absence of inorganic bases such as sodium carbonate, potassium carbonate, sodium hydrogencarbonate and the like; tertiary amines such as triethylamine, diisopropylethylamine and the like; and pyridines such as pyridine, 4-methylaminopyridine and the like. The reaction is preferably carried out in the presence of a silylating agent such as trimethylsilylacetamide, trimethylsilylchloride and the like. Solvents employed are not specifically limited, unless giving any influence on the reaction, which can include hydrocarbons such as benzene, toluene, xylene, hexane, heptane and the like; halogenated hydrocarbons such as chloroform, methylene chloride, 1,2-dichloroethylene, carbon tetrachloride and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; pyridine; and the mixtures thereof. The reaction may be carried out at a temperature ranging from ice-cooling to reflux-heating. The reaction time can be varied, depending on a reagent and a reaction temperature, etc., and is usually 0.5 to 24 hours. The reaction is preferably carried out at 20 to 50° C. in the presence of trimethylsilylacetamide in dimethylformamide for 6 to 12 hours.

A compound represented by formula (XXXXX)

(XXXXX)
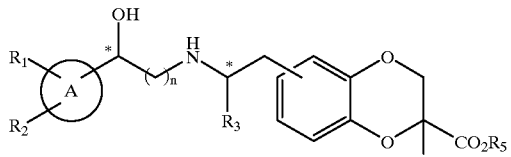

wherein A, n, $R_1$, $R_2$, $R_3$, $R_4$ and $R_5$ are as defined for formula (I), with the proviso that $R_3$ is not a hydrogen atom can be respectively separated into its optically active compounds by the following method.

The compound represented by formula (XXXXX) is reacted with a compound represented by formula (XXXXXI)

wherein $R_{23}$ is a $(C_1-C_6)$alkyl group, a $(C_1-C_6)$alkoxy group or a benzyloxy group, W is a chlorine atom or an oxygen atom, with the proviso that m is 1 when W is a chlorine atom and m is 2 when W is an oxygen atom, or with a compound represented by formula (XXXXXII)

(XXXXXII)

wherein Y is a chlorine atom or an imidazolyl group to give a compound represented by formula (XXXXXIII)

(XXXXXIII)
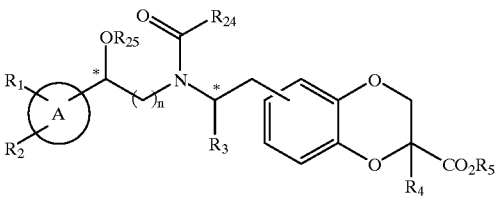

wherein A, n, $R_1$, $R_2$, $R_3$, $R_4$ and $R_5$ are as defined for formula (XXXXX) with the proviso that $R_3$ is not a hydrogen atom, $R_{24}$ is a $(C_1-C_4)$alkyl group, a $(C_1-C_4)$alkoxy group or a benzyloxy group, $R_{25}$ is a hydrogen atom, or $R_{24}$ and $R_{25}$ together represent a single bond (Step B'), and diastereoisomers of the compound represented by formula (XXXXXIII) are separated and purified by a fractional recrystallization, a medium pressure column chromatography or a preparative high performance liquid chromatography to give a compound represented by formula (XXXXXIIIa)

(XXXXXIIIa)
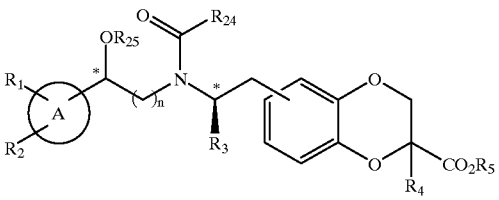

wherein A, n, $R_1$, $R_2$, $R_3$, $R_4$, $R_5$, $R_{24}$ and $R_{25}$ are as defined for formula (XXXXXIII) and a compound represented by formula (XXXXXIIIb)

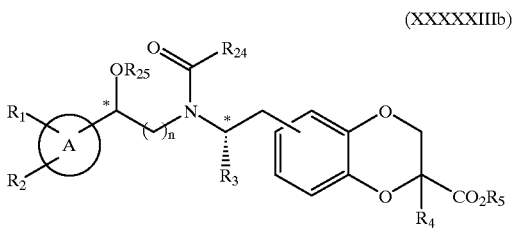

(XXXXXIIIb)

wherein A, n, $R_1$, $R_2$, $R_3$, $R_4$, $R_5$, $R_{24}$ and $R_{25}$ are as defined for formula (XXXXXIII) (Step C'), and then the compounds represented by formulae (XXXXXIIIa) and (XXXXXIIIb) are respectively hydrolyzed or catalytic-hydrogenated to give a compound of formula (XXXXXa)

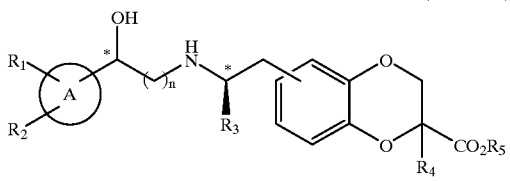

(XXXXXa)

wherein A, n, $R_1$, $R_2$, $R_3$, $R_4$ and $R_5$ are as defined for formula (XXXXX) from the compound of formula (XXXXXIIIa) and a compound of formula (XXXXXb)

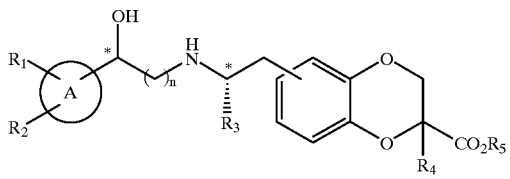

(XXXXXb)

wherein A, n, $R_1$, $R_2$, $R_3$, $R_4$ and $R_5$ are as defined for formula (XXXXX) from the compound of formula (XXXXXIIIb) (Step D').

Step B' is the step of preparing the compound of formula (XXXXXIII). This reaction is usually carried out in the presence of a solvent. Solvents used are not specifically limited, unless giving any influence on the reaction, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; sulfoxides such as dimethylsulfoxide and the like; sulforan; and the mixtures thereof. Examples of the compounds of formula (XXXXXI) include methyl chlorocarbonate, ethyl chlorocarbonate, di-t-butyl dicarbonate, acetyl chloride, acetic anhydride, carbobenzoxy chloride and the like. Examples of the compounds of formula (XXXXXII) include phosgene, N,N'-carbonyldiimidazole and the like. The reaction is usually carried out in the presence of a base. Bases employed can include carbonates such as potassium carbonate, sodium carbonate and the like; hydroxides such as sodium hydroxide, potassium hydroxide, lithium hydroxide, calcium hydroxide and the like; alkali metal hydrides such as sodium hydride, potassium hydride, calcium hydride and the like; tert-alkylamines such as triethylamine, N,N-diisopropylethylamine and the like; pyridines such as pyridine, 4-dimethylaminopyridine; and the mixtures thereof. The reaction may be carried out at a temperature ranging from ice-cooling to reflux-heating. The reaction time can be varied, depending on a reagent and a reaction temperature, etc., and is usually 1 to 24 hours. This reaction is preferably carried out by using di-t-butyl dicarbonate, carbobenzoxy chloride or N,N'-carbonyldiimidazole at 0 to 50° C. in the presence of alkylamine in halogenated hydrocarbones or ethers for 1 to 12 hours. More preferably, the reaction is carried out by using di-t-butyldicarbonate or N,N'-carbonyldiimidazole at 0 to 40° C. in the presence of triethylamine in tetrahydrofuran for 0.5 to 12 hours.

Step C' is the step of preparing compounds of formula (XXXXXIIIa) and formula (XXXXXIIIb) from the compound of formula (XXXXXIII) by separation and purification. This step is carried out by a fractional recrystallization, a medium pressure column chromatography or a preparative high performance liquid chromatography. In case of a fractional recrystallization, the solvents used are not specifically limited, unless giving any influence on the recrystallization, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; acetic acid esters such as ethyl acetate, methyl acetate and the like; and the mixtures thereof. Preferably used are acetic acid esters, alcohols, mixed solvents of acetic acid esters and hydrocarbons, mixed solvents of alcohols and hydrocarbons. More preferable are mixed solvents of ethyl acetate and hexane (mixing ratio; 1:99–99:1, v/v) or mixed solvents of isopropanol and hexane (mixing ratio; 1:99–99:1, v/v). The temperature of recrystallization can be varied, depending on conditions of solvents, etc., and usually ranging from ice-cooling to reflux-heating. The recrystallization is preferably carried out by dissolving in ethyl acetate or isopropanol, adding equal volumes of hexane and allowing to stand or stirring at 10 to 30° C.

In case of a column chromatography or a preparative high performance liquid chromatography, column carriers used can include silica gel (crushed or spherical, particle diameter 5 μm–70 μm), and a mobile phase used is not specifically limited, unless giving any influence on the separation, which can include hydrocarbons such as benzene, toluene, xylene, hexane, heptane and the like; halogenated hydrocarbons such as chloroform, methylene chloride, carbon tetrachloride, 1,2-dichloroethylene and the like; ethers such as diethyl ether, diisopropyl ether, tetrahydrofuran, dioxane and the like; alcohols such as methanol, ethanol, isopropanol and the like; acetic acid esters such as ethyl acetate, methyl acetate and the like; and the mixtures thereof. Preferably used are mixed solvents of acetic acid esters and hydrocarbons, in particular a mixed solvent of ethyl acetate and hexane. The column chromatography or preparative high performance liquid chromatography is preferably carried out by using silica gel (spherical, particle diameter 5 gm–20 μm) as a carrier and a mixed solvent of ethyl acetate and n-hexane (1:10–1:1, v/v) as a mobile phase at a pressure ranging from 5 kgf/cm² to 120 kgf/cm².

Step D' is the step of hydrolyzing or catalytic-hydrogenating the compound of formula (XXXXXIIIa) or formula (XXXXXIIIb). The hydrolysis is carried out by reacting the compound with water in the presence of an acid or a base. In case of acidic conditions, acids employed can include inorganic acids such as hydrochloric acid, sulfuric acid, phosphoric acid, nitric acid and the like; organic acids such as acetic acid, propionic acid and the like; sulfonic acids such as methanesulfonic acid, toluenesulfonic acid, camphorsulfonic acid and the like; and the mixtures thereof. In case of basic conditions, bases employed can include hydroxides such as sodium hydroxide, potassium hydroxide, lithium hydroxide and the like; carbonates such as potassium carbonate, sodium carbonate and the like; and the mixtures thereof. The reaction is usually carried out in a solvent. Solvents used are not specifically limited, unless giving any influence on the reaction, which can include hydrocarbons such as benzene, toluene, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; sulfoxides such as dimethylsulfoxide and the like; sulforan; organic acids such as acetic acid, propionic acid and the like; water; and the mixtures thereof. The reaction may be carried out at a temperature ranging from ice-cooling to reflux-heating. The reaction time can be varied, depending on a reagent and a reaction temperature, etc., and is usually 0.5 to 48 hours. The reaction is preferably carried out at a temperature ranging from 0° C. to reflux-heating in the presence of hydrochloric acid or sulfuric acid in alcohols, in particular methanol or ethanol or a mixed solvent of ethanol and water for 0.5 to 14 hours, or under reflux-heating in the presence of sodium hydroxide or potassium hydroxide in alcohols, in particular a mixed solvent of methanol or ethanol and water for 1 to 12 hours. In case of the compound of formula (XXXXXIIIa) or formula (XXXXXIIIb) wherein $R_{24}$ is a benzyloxy group, the reaction is also carried out by catalytic hydrogenation. In case of catalytic hydrogenation, the reaction is usually carried out in the presence of a catalyst. Catalysts which can be used include-the hydrogenation catalysts such as palladium-carbon, platinum oxide, palladium hydroxide and the like. Solvents used are not specifically limited, unless giving any influence on the reaction, which can include hydrocarbons such as benzene, toluere, xylene, hexane, heptane and the like; ethers such as diethyl ether, diisopropyl ether, tetrahydrofuran, dioxane and the like; amides such as dimethylformamide, dimethylacetamide, hexamethylphosphoric triamide and the like; alcohols such as methanol, ethanol, isopropanol and the like; organic acid esters such as methyl acetate, ethyl acetate and the like; organic acids such as acetic acid and the like; and the mixtures thereof. This reaction is carried out by using hydrogen gas at atmospheric pressure or at medium to high pressure, preferably using hydrogen gas at 1–5 kg/cm² or using formates as a hydrogen donor. The reaction is occasionally carried out by adding an acid. Acids employed can include inorganic acids such as hydrochloric acid, sulfuric acid, phosphoric acid, nitric acid and the like; organic acids such as acetic acid, propionic acid and the like; sulfonic acids such as methanesulfonic acid, toluenesulfonic acid, camphorsulfonic acid and the like; and the mixtures thereof. The reaction time can be varied, depending on a reagent and a reaction temperature, etc., and is usually 0.5 to 12 hours. This reaction is preferably carried out by using palladium hydroxide or palladium-carbon at 0 to 50° C. under hydrogen gas of atmospheric pressure in alcohols, in particular methanol or ethanol for 0.5 to 6 hours.

The present compounds of formula (I) may be converted, if desired, to the corresponding acid addition salts with pharmaceutically acceptable acids, and the acid addition salts are included within the scope of this invention. The acid addition salts include, for examples, the salts with inorganic acids such as hydrochloric acid, hydrobromic acid, sulfuric acid, phosphoric acid and the like, or the salts with organic acids such as acetic acid, succinic acid, oxalic acid, malic acid, tartaric acid, malonic acid, fumaric acid, maleic acid and the like.

The compounds of formula (I) wherein $R_5$ is a hydrogen atom may be converted, if desired, to the corresponding addition salts with pharmaceutically acceptable alkali metals, and the addition salts are included within the scope of this invention. The alkali metal addition salts include, for examples, sodium salt, lithium salt, potassium salt and the like.

The present compounds of the above-mentioned formula (I) and the salts thereof have β3 agonistic activity, antihyperglycemic activity and anti-obesity activity. Consequently, these compounds are useful for a prophylactic or therapeutic agent for diabetes, hyperglycemia and obesity in human or other mammals such as pet animals, and possess utility for increasing lean meat in edible animals.

The present compounds of formula (I) can be usually administered in various dosage forms which include the preparations adapted for oral or parenteral administration. Oral preparations include tablets, capsules, granules, powders and syrups, and parenteral preparations include injections (intravenous, intramuscular, subcutaneous), drops, suppositories.

These preparations can be prepared by conventional methods employing conventional additives such as excipients, binders, disintegrants, lubricants, flavorings, solubiliziing aids, suspending agents, coating agents or the like. The dosage of administration is depending upon severity of the disease, the age and weight of patients, and the mode of administration. Daily dosage of the active ingredient for adult is 0.01 to 2000 mg.

This invention will be further illustrated by the following examples. However, it is to be understood that the invention is not intended to be limited to the specific embodiments.

EXAMPLE 1

6-{2-[2-Hydroxy-2-(3-methoxyphenyl)ethyl]amino}propyl-2,3-dihydro-1,4-benzodioxin-2-carboxylic acid methyl ester

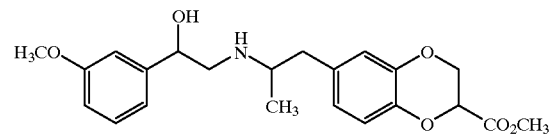

To a solution of 2-amino-1-(3-methoxyphenyl)ethanol (0.35 g) in benzene (50 ml) was added 6-acetonyl-2,3-dihydro-1,4-benzodioxin-2-carboxylic acid methyl ester (0.5 g), and the mixture was heated under reflux for one hour while removing a resulting water with Dean-Stark apparatus. After the solvent was distilled off under reduced pressure, the residue was dissolved in absolute methanol (20 ml). 5% palladium-carbon was added, and the mixture was stirred under hydrogen atmosphere for 5 hours. The reaction solution was filtered, and the solvent was distilled off under reduced pressure. The residue was chromatographed over silica gel (20 g) with 4% methanol/chloroform (v/v) as eluent to give the title compound (0.35 g, yield=42%) as a pale yellow oil.

¹H NMR (CDCl₃, 400 MHz) δ 1.06(d, J=6.3 Hz, 3H), 2.48–2.71(m, 3H), 2.85–2.99(m, 2H), 3.80(s, 3H), 3.81 (s,

3H), 4.35–4.37(m, 2H), 4.57(dd, J=3.9 Hz, 8.7 Hz, 0.5H), 4.63(dd, J=3.4 Hz, 8.7 Hz, 0.5H), 4.80–4.83(m, 1H), 6.66–6.69(m, 2H), 6.78–6.81(m, 1H), 6.89–6.93(m, 3H), 7.22(d, J=7.8 Hz, 1H).

Then, the corresponding hydrochloride was obtained as a pale pink amorphous solid in a conventional manner.

EXAMPLE 2

6-{2-[2-Hydroxy-2-(3-tolyl)ethyl]amino}propyl-2,3-dihydro-1,4-benzodioxin-2-carboxylic acid methyl ester

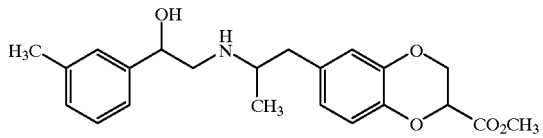

To a solution of 2-amino-1-(3-tolyl)ethanol (0.35 g) in benzene (100 ml) was added 6-acetonyl-2,3-dihydro-1,4-benzodioxin-2-carboxylic acid methyl ester (0.5 g), and the mixture was heated under reflux for one hour while removing a resulting water with Dean-Stark apparatus. After the solvent was distilled off under reduced pressure, the residue was dissolved in absolute methanol (20 ml). Platinum oxide (0.09 g) was added, and the mixture was stirred under hydrogen atmosphere for 5 hours. The reaction solution was filtered, and the solvent was distilled off under reduced pressure. The residue was chromatographed over silica gel (20 g) with 4% methanol/chloroform (v/v) as eluent to give the title compound (0.41 g, yield=46%) as a pale yellow oil.

$^1$H NMR (CDCl$_3$, 400 MHz) δ 1.07(d, J=6.3 Hz, 3H), 2.34(s, 3H), 2.50–2.56(m, 1H), 2.59–2.71(m, 2H), 2.87–3.00(m, 2H), 3.81(s, 3H), 4.37(d, J=3.4 Hz, 2H), 4.55–4.65(m, 1H), 4.81–4.83(m, 1H), 6.67–6.70(m, 2H), 6.90–6.93(m, 1H), 7.06–7.23(m, 4H).

Then, the corresponding hydrochloride was obtained as a brown amorphous solid in a conventional manner.

EXAMPLE 3

6-[2-(2-Hydroxy-2-phenylethyl)amino]propyl-2,3-dihydro-1,4-benzodioxin-2-carboxylic acid ethyl ester

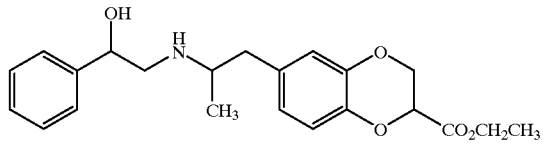

The title compound was obtained as a pale yellow oily substance by using 2-amino-1-phenylethanol and 6-acetonyl-2,3-dihydro-1,4-benzodioxin-2-carboxylic acid ethyl ester according to the same process as described in Example 2. Yield=70%.

$^1$H NMR (CDCl$_3$, 400 MHz) δ 1.07(d, J=6.4 Hz, 2H), 1.28 (t, J=7.3 Hz, 3H), 2.48–2.67(m, 3H), 2.80–2.98(m, 2H), 4.23–4.29(m, 2H), 4.36–4.39(m, 2H), 4.53(dd, J=3.4 Hz, 8.8 Hz, 0.6H), 4.60(dd, J=3.9 Hz, 8.8 Hz, 0.4H), 4.83(dd, J=3.9 Hz, 7.3 Hz, 1H), 6.65–6.69(m, 2H), 6.80–6.83(m, 1H), 7.24–7.33(m, 5H).

Then, the corresponding hydrochloride was obtained as a colorless amorphous solid in a conventional manner.

EXAMPLE 4

7-[2-(2-Hydroxy-2-phenylethyl)amino]propyl-2,3-dihydro-1,4-benzodioxin-2-carboxylic acid ethyl ester

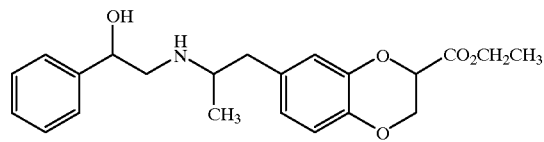

The title compound was obtained as a pale yellow oily substance by using 2-amino-1-phenylethanol and 7-acetonyl-2,3-dihydro-1,4-benzodioxin-2-carboxylic acid ethyl ester according to the same process as described in Example 2. Yield=77%.

$^1$H NMR (CDCl$_3$, 400 MHz) δ 1.05(d, J=5.8 Hz, 3H), 1.28(t, J=7.3 Hz; 3H), 2.48–2.71(m, 3H), 2.85–2.98(m, 2H), 4.23–4.29 (m, 2H), 4.34–4.36(m, 2H), 4.59(dd, J=3.4 Hz, 9.2 Hz, 0.7H), 4.65–4.67(m, 0.3H), 4.78–4.80(m, 1H), 6.61–6.66(m, 1H), 6.75–6.82(m, 2H), 7.24–7.33(m, 5H).

Then, the corresponding hydrochloride was obtained as a colorless amorphous solid in a conventional manner.

EXAMPLE 5

6-[2-(2-Hydroxy-2-piperonylethyl)amino]propyl-2,3-dihydro-1,4-benzodioxin-2-carboxylic acid methyl ester

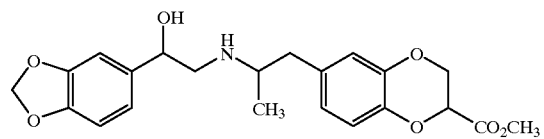

The title compound was obtained as a pale yellow oily substance by using 2-amino-1-piperonylethanol according to the same process as described in Example 2. Yield=76%.

$^1$H NMR (CDCl$_3$, 400 MHz) δ 1.06 (d, J=6.3 Hz, 3H), 1.40–2.20(br, 2H, substituted with deuterium oxide), 2.48–2.70(m, 3H), 2.79–2.96(m, 2H), 3.82(s, 3H), 4.30–4.44(m, 2H), 4.49(dd, J=3.9 Hz, 8.8 Hz, 0.5H), 4.56 (dd, J=3.4 Hz, 8.3 Hz, 0.5H), 4.83(brs, 1H), 5.94(s, 2H), 6.67(d, J=4.4 Hz, 1H), 6.68(d, J=6.3 Hz, 1H), 6.71–6.80(m, 2H), 6.85(d, J=3.4 Hz, 1H), 6.92(dd, J=3.4 Hz, 8.8 Hz, 1H).

Then, the corresponding hydrochloride was obtained as a yellow amorphous solid in a conventional manner.

$^1$H NMR(DMSO-d$_6$, 400 MHz) δ 1.10(d, J=9.8 Hz, 1.5 H), 1.12 (d, J=6.4 Hz, 1.5H), 2.44–2.60(m, 1H), 2.95–3.25 (m, 3H), 3.30–3.50(m, 1H), 3.69(s, 3H), 4.28(d, J=10.3 Hz, 1H), 4.42 (dd, J=3.4 Hz, 12.2 Hz, 1H), 4.90–5.03(m, 1H), 5.18(brs, 1H), 5.80–6.40(br, 1H, substituted with deuterium oxide), 6.005(s, 1H), 6.014(s, 1H), 6.70–6.80(m, 2H), 6.81–6.95(m, 3H), 6.99(s, 1H), 8.61–8.90(br, 1H, substituted with deuterium oxide), 9.30–9.50(br, 1H, substituted with deuterium oxide); $^{13}$C NMR(DMSO-d$_6$, 400 MHz) δ 14.8, 15.5, 37.2, 37.8, 50.7, 52.7, 54.8, 55.0, 64.8, 68.3, 68.4, 71.6, 101.2, 106.7, 108.3, 117.3, 117.8, 118.0, 119.6, 123.0, 123.1, 130.3, 135.8, 141.2, 142.9, 147.0, 147.5, 168.8.

EXAMPLE 6

6-{2-{2-[3-(4-Chlorophenoxy)phenyl]-2-hydroxyethyl}amino}propyl-2,3-dihydro-1,4-benzodioxin-2-carboxylic acid methyl ester

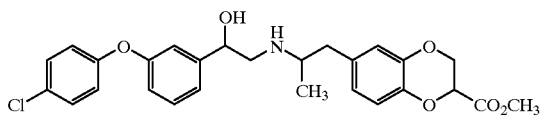

The title compound was obtained as a colorless oily substance by using 2-amino-1-[3-(4-chlorophenoxy)phenyl]ethanol according to the same process as described in Example 2. Yield=85%.

$^1$H NMR (CDCl$_3$, 400 MHz) δ 1.06(d, J=6.4 Hz, 3H), 1.20–2.40 (br, 2H, substituted with deuterium oxide), 2.48–2.70(m, 3H), 2.80–2.91(m, 1.5H), 2.97(dd, J=3.4 Hz, 12.2 Hz, 0.5H), 3.81(s, 3H), 4.30–4.40(m, 2H), 4.54(dd, J=3.4 Hz, 8.8 Hz, 0.5H), 4.61(dd, J=3.4 Hz, 8.8 Hz, 0.5H), 4.82(dd, J=3.9 Hz, 7.8 Hz, 1H), 6.60–6.73(m, 2H), 6.80–7.12(m, 6H), 7.20–7.40(m, 3H).

Then, the corresponding hydrochloride was obtained as a colorless amorphous solid in a conventional manner.

$^1$H NMR (DMSO-d$_6$, 400 MHz) δ 1.09(d, J=6.4 Hz, 1.5H), 1.11 (d, J=6.3 Hz, 1.5H), 2.48–2.60(m, 1H), 2.95–3.25(brm, 2H), 3.30–3.90(brm, 1H), 3.68(s, 3H), 4.26 (brd, J=11.2 Hz, 1H), 4.42(dd, J=2.9 Hz, 11.7 Hz, 1H), 5.02(brt, J=8.3 Hz, 1H), 5.16 (brs, 1H), 6.70–6.80(brm, 2H), 6.90(d, J=8.3 Hz, 1H), 6.95 (dd, J=2.0 Hz, 7.8 Hz, 1H), 6.99–7.27(m, 4H), 7.30–7.50(m, 2H), 8.60–8.80(br, 1H, substituted with deuterium oxide), 9.19–9.30(br, 1H, substituted with deuterium oxide); $^{13}$C NMR (DMSO-d$_6$, 400 MHz) δ 14.9, 15.6, 18.7, 37.3, 37.9, 50.8, 52.7, 55.0, 55.2, 56.3, 64.8, 68.2, 68.3, 71.6, 116.4, 117.2, 118.0, 118.3, 118.9, 120.5, 121.7, 123.0, 123.1, 127.5, 130.2, 130.3, 130.4, 141.2, 142.9, 144.5, 155.7, 156.6, 157.0, 168.7.

EXAMPLE 7

6-{2-[2-(4-Biphenyl)-2-hydroxyethyl]amino}propyl-2,3-dihydro-1,4-benzodioxin-2-carboxylic acid methyl ester

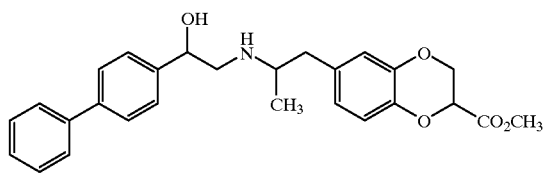

The title compound was obtained as a colorless oily substance by using 2-amino-1-(4-biphenyl)ethanol according to the same process as described in Example 2. Yield=84%.

$^1$H NMR (CDCl$_3$, 400 MHz) δ 1.08 (d, J=5.9 Hz, 3H), 1.50–2.30(br, 2H, substituted with deuterium oxide), 2.50–2.80(m, 3H), 2.83–2.98(m, 1.5H), 3.02(dd, J=3.4 Hz, 12.2 Hz, 0.5H), 3.806(s, 1.5H), 3.813(s, 1.5H), 4.35 (dd, J=3.9 Hz, 8.3 Hz, 2H), 4.64(dd, J=3.9 Hz, 9.3 Hz, 0.5H), 4.71(dd, J=3.9 Hz, 8.8 Hz, 0.5H), 4.74–4.88(in, 1H), 6.61–6.78(m, 2H), 6.91(d, J=7.3 Hz, 0.5H), 6.93(d, J=8.3 Hz, 0.5H), 7.20–7.70(m, 9H).

Then, the corresponding hydrochloride was obtained as a pale pink amorphous solid in a conventional manner.

$^1$H NMR (DMSO-d$_6$, 400 MHz) δ 1.13(d, J=6.3 Hz, 1.5H), 1.15 (d, J=6.4 Hz, 1.5H), 2.43–2.62(m, 1H), 3.00–3.31(m, 3H), 3.34–3.50(m, 1H), 3.69(s, 3H), 4.28(brd, J=9.8 Hz, 1H), 4.43 (dd, J=2.9 Hz, 11.7 Hz, 1H), 5.13(brt, J=7.8 Hz, 1H), 5.18(brs, 1H), 6.70–6.84(brm, 2H), 6.91(d, J=7.8 Hz, 1H), 7.30–7.75(m, 9H), 8.75–8.95(br, 1H, substituted with deuterium oxide), 9.46–9.65(br, 1H, substituted with deuterium oxide); $^{13}$C NMR (DMSO-d$_6$, 400 MHz) δ 14.8, 15.5, 37.1, 37.8, 50.6, 52.6, 54.8, 55.0, 64.7, 68.3, 69.0, 71.4, 117.2, 117.8, 122.9, 126.8, 127.6, 129.1, 130.3, 139.8, 139.9, 141.0, 141.1, 142.8, 168.6.

EXAMPLE 8

6-{2-[2-(3-Benzyloxyphenyl)-2-hydroxyethyl]amino}propyl-2,3-dihydro-1,4-benzodioxin-2-carboxylic acid methyl ester

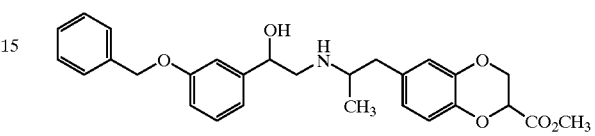

The title compound was obtained as a yellow oily substance by using 2-amino-1-(3-benzyloxyphenyl)ethanol according to the same process as described in Example 2. Yield=45%.

$^1$H NMR (CDCl$_3$, 400 MHz) δ 1.05(d, J=6.4 Hz, 3H), 2.20–2.90(m, 6.5H, 2H, substituted with deuterium oxide), 2.95(dd, J=3.4 Hz, 12.2 Hz, 0.5H), 3.80(s, 3H), 4.34(t, J=3.9 Hz, 2H), 4.58(dd, J=3.4 Hz, 8.8 Hz, 0.5H), 4.64 (dd, J=3.4 Hz, 8.3 Hz, 0.5H), 4.80(dd, J=3.9 Hz, 7.8 Hz, 1H), 5.05(s, 2H), 6.58–6.72(m, 2H), 6.76–6.96(m, 3H), 7.00(brs, 1H), 7.18–7.27(m, 2H), 7.28–7.46(m, 4H).

Then, the corresponding hydrochloride was obtained as a pale yellow amorphous solid in a conventional manner.

$^1$H NMR (DMSO-d$_6$, 400 MHz) δ 1.11(d, J=6.4 Hz, 1.5H), 1.13(d, J=6.3 Hz, 1.5H), 2.40–2.61(m, 1H), 2.95–3.25(m, 3H), 3.30–3.45(m, 1H), 3.69(s, 3H), 4.28(d, J=11.2 Hz, 1H), 4.42 (d, J=11.2 Hz, 1H), 5.03(brt, J=8.3 Hz, 1H), 5.12(s, 2H), 5.18(brs, 1H), 6.65–6.85(m, 2H), 6.86–7.05(m, 3H), 7.09(brs, 1H), 7.25–7.50(m, 6H), 8.65–8.90(brm, 1H, substituted with deuterium oxide), 9.35–9.55(brm, 1H, substituted with deuterium oxide); $^{13}$C NMR (DMSO-d$_6$, 400 MHz) δ 14.7, 15.4, 37.1, 37.7, 50.9, 52.4, 54.9, 64.6, 68.3, 68.4, 69.2, 71.3, 112.5, 112.6, 113.8, 117.0, 118.4, 122.7, 122.8, 127.7, 127.8, 128.3, 128.4, 129.5, 130.3, 137.0, 141.0, 142.7, 143.6, 158.4, 168.5.

EXAMPLE 9

6-[2-(2-Cyclohexyl-2-hydroxyethyl)amino]propyl-2,3-dihydro-1,4-benzodioxin-2-carboxylic acid methyl ester

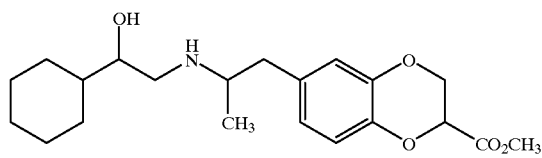

The title compound was obtained as a pale yellow oily substance by using 2-amino-1-cyclohexylethanol according to the same process as described in Example 2. Yield=82%.

$^1$H NMR (CDCl$_3$, 400 MHz) δ 0.95–1.40(m, 6H), 1.04(d, J=6.4 Hz, 1.5H), 1.05(d, J=6.4 Hz, 1.5H), 1.55–1.98(m, 5H), 2.34–2.70(m, 3H), 2.75(dd, J=3.4 Hz, 12.0 Hz, 0.5H), 2.80–2.91 (m, 1.5H), 3.19–3.31(m, 1H), 3.82(s, 3H), 4.30–4.48(m, 2H), 4.79–4.90(m, 1H), 6.69(s, 1H), 6.70(d, J=7.3 Hz, 1H), 6.92(dd, J=1.5 Hz, 8.1 Hz, 1H).

Then, the corresponding hydrochloride was obtained as a pale yellow amorphous solid in a conventional manner.

¹H NMR (DMSO-d₆, 400 MHz) δ 0.90–1.40(m, 6H), 1.09(d, J=6.8 Hz, 1.5H), 1.12(d, J=6.8 Hz, 1.5H), 2.45–2.60 (m, 1H), 2.75–2.88(m, 1H), 2.95–3.10(m, 1H), 3.11–3.20 (m, 1H), 3.29–3.40(brm, 1H), 3.59–3.67(brm, 1H), 3.70(s, 3H), 4.28(dd, J=2.9 Hz, 11.7 Hz, 1H), 4.42(dd, J=3.4 Hz, 11.7 Hz, 1H), 4.20–4.80(br, 1H, substituted with deuterium oxide), 5.18(brs, 1H), 6.73–6.78(m, 2H), 6.91(d, J=8.3 Hz, 1H), 8.44–8.70(brm, 1H, substituted with deuterium oxide), 9.05–9.25(brm, 1H, substituted with deuterium oxide); ¹³C NMR (DMSO-d₆, 400 MHz) δ 14.4, 15.3, 25.5, 25.6, 26.0, 27.4, 27.5, 28.4, 37.2, 37.7, 41.7, 47.8, 48.0, 48.6, 52.4, 54.6, 54.7, 54.9, 64.6, 70.0, 70.2, 71.3, 117.0, 117.6, 117.7, 122.7, 122.8, 130.2, 130.3, 140.0, 142.7, 168.4.

EXAMPLE 10
6-{2-[2-(3-Chlorophenyl)-2-hydroxyethyl]amino}propyl-2,3-dihydro-1,4-benzodioxin-2-carboxylic acid methyl ester

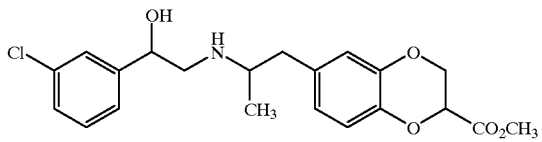

The title compound was obtained as a pale yellow oily substance by using 2-amino-1-(3-chlorophenyl)ethanol according to the same process as described in Example 2. Yield=46%.

¹H NMR (CDCl₃, 400 MHz) δ 1.07(d, J=6.4 Hz, 3H), 1.30–2.15(br, 2H, substituted with deuterium oxide), 2.49–2.67(m, 3H), 2.80–2.91(m, 1.5H), 2.97(dd, J=3.4 Hz, 12.2 Hz, 0.5H), 4.36–4.39(m, 2H), 4.53(dd, J=3.4 Hz, 8.8 Hz, 0.5H), 4.60(dd, J=3.9 Hz, 8.8 Hz, 0.5H), 4.83(dd, J=3.9 Hz, 7.3 Hz, 1H), 6.60–6.75(m, 2H), 6.92(d, J=8.8 Hz, 0.5H), 6.93(d, J=8.8 Hz, 0.5H), 7.18–7.28(m, 3H), 7.35(brs, 1H).

Then, the corresponding hydrochloride was obtained as a pale yellow amorphous solid in a conventional manner.

¹H NMR (DMSO-d₆, 400 MHz) δ 1.11(d, J=6.4 Hz, 1.5H), 1.14 (d, J=6.8 Hz, 1.5H), 2.45–2.60(m, 0.5H), 3.00–3.58(brm, 4.5H), 3.69(s, 3H), 4.28(dd, J=2.4 Hz, 11.7 Hz, 1H), 4.43(dd, J=3.4 Hz, 11.7 Hz, 1H), 5.09(brt, J=7.3 Hz, 1H), 5.13–5.21(m, 1H), 6.20–6.52(br, 1H, substituted with deuterium oxide), 6.70–6.82(m, 2H), 6.91(d, J=7.8 Hz, 1H), 7.31–7.41(m, 3H), 7.49(d, J=1.5 Hz, 1H), 8.73–8.95 (brm, 1H, substituted with deuterium oxide), 9.40–9.60 (brm, 1H, substituted with deuterium oxide); ¹³C NMR (DMSO-d₆, 400 MHz) δ 14.7, 15.4, 37.1, 37.7, 38.9, 50.6, 52.4, 54.8, 55.0, 6,4.6, 67.8, 68.0, 71.3, 117.0, 117.6, 117.7, 117.8, 122.7, 124.7, 125.9, 127.6, 128.3, 130.2, 130.3, 133.1, 141.0, 142.7, 144.4, 168.5.

EXAMPLE 11
6-{2-[2-Hydroxy-2-(3-trifluoromethylphenyl)ethyl]amino}propyl-2,3-dihydro-1,4-benzodioxin-2-carboxylic acid methyl ester

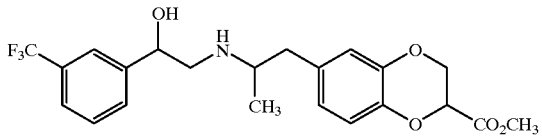

The title compound was obtained as a pale brown oily substance by using 2-amino-1-(3-trifluoromethylphenyl)ethanol according to the same process as described in Example 2. Yield=99%.

¹H NMR (CDCl₃, 400 MHz) δ 1.09(d, J=6.3 Hz, 3H), 1.80–3.10(br, 3H, substituted with deuterium oxide), 2.50–2.70(m, 3H), 2.85–2.99(m, 1.5H), 3.01(dd, J=3.9 Hz, 12.2 Hz, 0.5H), 3.81(s, 1.5H), 3.82(s, 1.5H), 4.37(t, J=3.9 Hz, 2H), 4.63(dd, J=3.4 Hz, 8.8 Hz, 0.5H), 4.70(dd, J=3.4 Hz, 8.8 Hz, 0.5H), 4.83(dd, J=3.9 Hz, 7.3 Hz, 1H), 6.62–6.74(m, 2H), 6.89–6.99(m, 1H), 7.40–7.60(m, 2H), 7.63 (s, 1H).

Then, the corresponding hydrochloride was obtained as a gray amorphous solid in a conventional manner.

m.p. 63–69° C. ¹H NMR (DMSO-d₆, 400 MHz) δ 1.12 (d, J=6.4 Hz, 1.5H), 1.14(d, J=6.4 Hz, 1.5H), 2.49–2.62(m, 1H), 3.10–3.54(m, 4H), 3.69(s, 3H), 4.28(brd, J=11.7 Hz, 1H), 4.42(dd, J=2.9 Hz, 11.7 Hz, 1H), 5.25–5.38(brm, 2H), 6.00–6.86(br, 1H, substituted with deuterium oxide), 6.76(s, 1H), 6.91(d, J=7.8 Hz, 1H), 7.64(t, J=7.3 Hz, 1H), 7.68(d, J=7.3 Hz, 1H), 7.74(d, J=7.3 Hz, 1H), 7.79(s, 1H), 8.80–9.00 (brm, 1H, substituted with deuterium oxide), 9.50–9.88 (brm, 1H, substituted with deuterium oxide); ¹³C NMR (DMSO-d₆, 400 MHz) δ 14.7, 15.4, 37.0, 37.7, 50.4, 52.5, 54.8, 55.0, 64.6, 67.8, 68.0, 71.4, 117.1, 117.7, 122.6, 122.8, 124.6, 125.7, 129.3, 129.6, 130.2, 130.3, 141.1, 142.8, 143.2, 168.6.

EXAMPLE 12
6-{2-[2-Hydroxy-2-(4-fluorophenyl)ethyl]amino}propyl-2,3-dihydro-1,4-benzodioxin-2-carboxylic acid methyl ester

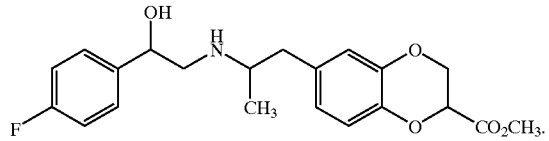

The title compound was obtained as a colorless oily substance by using 2-amino-1-(4-fluorophenyl)ethanol according to the same process as described in Example 2. Yield=88%.

¹H NMR (CDCl₃, 400 MHz) δ 1.06(d, J=6.0 Hz, 3H), 2.51–2.66(m, 3H), 2.83–2.93(m, 2H), 3.80(s, 1.5H), 3.81(s, 1.5H), 4.36–4.37(m, 2H), 4.53–4.63(m, 1H), 4.81–4.83(m, 1H), 6.65–6.69(m, 2H), 6.74–7.03(m, 3H), 7.25–7.34(m, 2H).

Then, the corresponding hydrochloride was obtained as a colorless amorphous solid in a conventional manner.

EXAMPLE 13
6-{2-[2-Hydroxy-2-(4-isopropylphenyl)ethyl]amino}propyl-2,3-dihydro-1,4-benzodioxin-2-carboxylic acid methyl ester

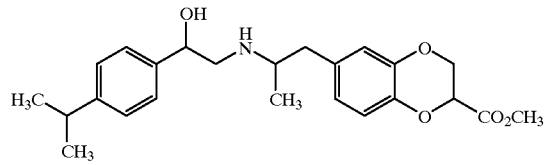

The title compound was obtained as a colorless oily substance by using 2-amino-1-(4-isopropylphenyl)ethanol according to the same process as described in Example 2. Yield=98%.

¹H NMR (CDCl₃, 400 MHz) δ 1.04(d, J=6.0 Hz, 3H), 1.23(d, J=7.0 Hz, 6H), 2.47–2.71(m, 3H), 2.85–2.96(m, 3H), 3.79(s, 1.5H), 3.80(s, 1.5H), 4.34–4.36(m, 2H), 4.79–4.82 (m, 1H), 4.54–4.63(m, 1H), 6.65–6.69(m, 2H), 6.89–6.95 (m, 1H), 7.19(d, J=8.0 Hz, 2H), 7.26(d, J=8.0 Hz, 2H).

Then, the corresponding hydrochloride was obtained as a colorless amorphous solid in a conventional manner.

EXAMPLE 14

6-[2-(3-Hydroxy-3-phenylpropyl)amino]propyl-2,3-dihydro-1,4-benzodioxin-2-carboxylic acid methyl ester

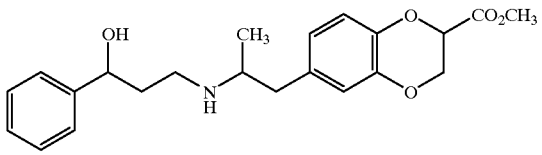

The title compound was obtained as a colorless oily substance by using 3-amino-1-phenylpropanol according to the same process as described in Example 2. Yield=35%.

$^1$H NMR (CDCl$_3$, 400 MHz) δ 1.08–1.13(m, 3H), 1.70–1.89(m, 2H), 2.51–3.00(m, 5H), 3.77(s, 1.5H), 3.79(s, 1.5H), 4.37–4.38(m, 2H), 4.82–4.84(m, 1H), 4.89–4.91(m, 1H), 6.70–6.71(m, 2H), 6.93–6.96(m, 1H), 7.23–7.37(m, 5H).

Then, the corresponding hydrochloride was obtained as a colorless amorphous solid in a conventional manner.

EXAMPLE 15

6-{2-[4-(4-Chlorophenyl)-4-hydroxypiperidinediyl]propyl}-2,3-dihydro-1,4-benzodioxin-2-carboxylic acid methyl ester

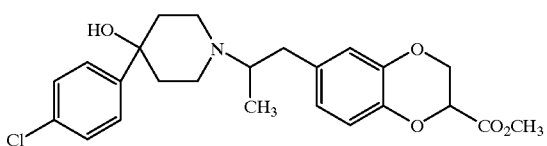

The title compound was obtained as a yellow oily substance by using 4-(4-chlorophenyl)-4-hydroxypiperidine according to the same process as described in Example 2. Yield=18%.

$^1$H NMR (CDCl$_3$, 400 MHz) δ 0.99(d, J=6.4 Hz, 3H), 1.21–1.28(m, 2H), 1.62–1.95(m, 3H, 1H, substituted with deuterium oxide), 2.02–2.20(m, 2H), 2.35(dd, J=9.8 Hz, 12.7 Hz, 1H), 2.65–3.00(m, 4H), 3.81(s, 3H), 4.28–4.42(m, 2H), 4.82(t, J=3.4 Hz, 1H), 6.60–6.80(m, 2H), 6.81–6.96(m, 1H), 7.31(d, J=11.8 Hz, 2H), 7.45(d, J=8.8 Hz, 2H).

Then, the corresponding hydrochloride was obtained as a pale yellow amorphous solid in a conventional manner.

$^1$H NMR (DMSO-d$_6$, 400 MHz) δ 1.00(d, J=5.9 Hz, 1.5H), 1.16(d, J=6.4 Hz, 1.5H), 1.49–2.10(m, 3H), 2.39–2.70(m, 2H), 2.96–3.80(m, 6H), 3.70(s, 3H), 3.90–4.60(brm, 1H, substituted with deuterium oxide), 4.30 (dd, J=2.4 Hz, 11.7 Hz, 1H), 4.44(dd, J=3.4 Hz, 11.7 Hz, 1H), 5.19(brs, 1H), 6.60–7.00(m, 3H), 7.38(d, J=8.8 Hz, 1H), 7.44(d, J=8.3 Hz, 1H), 7.53(d, J=8.3 Hz, 2H) $^{13}$C NMR (DMSO-d$_6$, 400 MHz) δ 12.3, 34.9, 35.5, 43.6, 45.4, 52.4, 61.9, 64.6, 67.3, 68.3, 71.4, 116.4, 117.0, 117.1, 117.7, 117.8, 122.7, 122.8, 126.7, 126.8, 128.1, 128.3, 130.3, 131.1, 131.5, 141.0, 142.7, 147.0, 168.5.

EXAMPLE 16

(2"R)-6-{2-[2-(3-Chlorophenyl)-2-hydroxyethyl]amino}propyl-2,3-dihydro-1,4-benzodioxin-2-carboxylic acid methyl ester

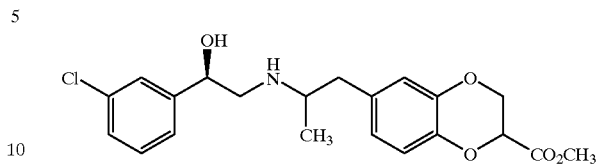

A solution of (R)-(−)-2-amino-1-(3-chlorophenyl)ethanol (1.50 g) and 6-acetonyl-2,3-dihydro-1,4-benzodioxin-2-carboxylic acid methyl ester (2.19 g) in benzene (40 ml) was heated under reflux for one hour while removing a resulting water with Dean-Stark apparatus and concentrated under reduced pressure. To a solution of the residue in methanol (40 ml) was added platinum oxide (0.15 g), and the mixture was stirred under hydrogen atmosphere for 1.5 hours. After the catalyst was filtered off, the filtrate was concentrated under reduced pressure. The residue was chromatographed over silica gel with methanol/ethyl acetate/aqueous ammonia (5/95/1, v/v) as eluent to give the title compound (3.51 g, yield=99%) as a pale yellow oil.

$^1$H NMR (CDCl$_3$, 400 MHz) δ 1.07(d, J=5.9 Hz, 3H), 1.50–2.49 (br, 2H, substituted with deuterium oxide), 2.50–2.70(m, 3H), 2.81–2.94(m, 1.5H), 2.97(dd, J=3.9 Hz, 5.2 Hz, 0.5H), 3.81, 3.82(pair of s, 3H), 4.32–4.42(m, 2H), 4.54(dd, J=3.4 Hz, 8.8 Hz, 0.5H), 4.61(dd, J=3.9 Hz, 8.8 Hz, 0.5H), 4.83(dd, J=3.9 Hz, 7.3 Hz, 1H), 6.62–6.73(m, 2H), 6.91(d, J=8.8 Hz, 0.5H), 6.93(d, J=8.3 Hz, 0.5H), 7.15–7.30 (m, 3H), 7.35(brs, 1H).

EXAMPLE 17

(2"S)-6-{2-[2-(3-Chlorophenyl)-2-hydroxyethyl]amino}propyl-2,3-dihydro-1,4-benzodioxin-2-carboxylic acid methyl ester

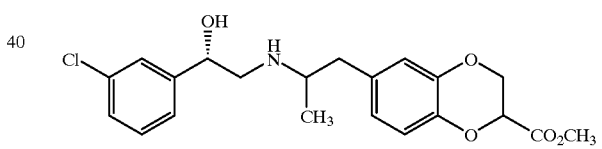

The title compound was obtained as a pale yellow oily substance by using (S)-(+)-2-amino-1-(3-chlorophenyl)ethanol according to the same process as described in Example 16. Yield=93%.

The spectral data were identical with those of Example 16.

EXAMPLE 18

(2"R)-6-[2-(2-Hydroxy-2-phenylethyl)amino]propyl-2,3-dihydro-1,4-benzodioxin-2-carboxylic acid methyl ester

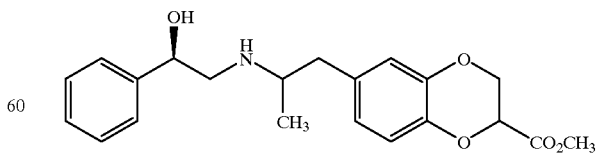

The title compound was obtained as a pale yellow oily substance by using (R)-(−)-2-amino-1-phenylethanol according to the same process as described in Example 16. Yield=40%.

EXAMPLE 19
(2"S)-6-[2-(2-Hydroxy-2-phenylethyl)amino]propyl-2,3-dihydro-1,4-benzodioxin-2-carboxylic acid methyl ester

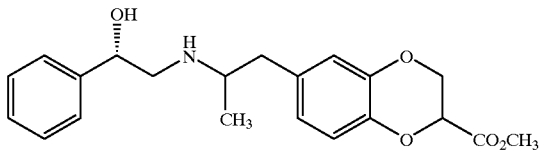

The title compound was obtained as a pale yellow amorphous solid by using (S)-(+)-2-amino-1-phenylethanol according to the same process as described in Example 16. Yield=52%.

The spectral data were identical with those of Example 18.

EXAMPLE 20
(2'R,2"R)-6-{2-[2-(3-Chlorophenyl)-2-hydroxyethyl]amino}propyl-2,3-dihydro-1,4-benzodioxin-2-carboxylic acid ethyl ester

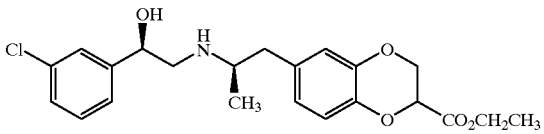

To a solution of (2'R,5"R)-6-{2-[5-(3-chlorophenyl)-2-oxo-3-oxazolidinyl]}propyl-2,3-dihydro-1,4-benzodioxin-2-carboxylic acid methyl ester (1.55 g) in ethanol (7.2 ml) was added 20% aqueous solution of sodium hydroxide (7.2 ml), and the mixture was heated under reflux for 3 hours. After the reaction solution was ice-cooled, concentrated hydrochloric acid was added to be pH 1–2, and concentrated under reduced pressure. Ethanol and benzene were added, and the solution was concentrated under reduced pressure. Being diluted with ethanol, the insolubles were filtered off. To the residue were added ethanol and benzene, and the mixture was heated under reflux for 1.5 hours while removing a resulting water with Dean-Stark apparatus. The solvent was distilled off under reduced pressure, and the residue was diluted with ethyl acetate, and washed in turn with saturated aqueous solution of sodium hydrogencarbonate and saturated aqueous sodium chloride. The organic layer was dried over anhydrous sodium sulfate, and concentrated under reduced pressure. The residue was chromatographed over silica gel with ethanol/ethyl acetate/aqueous ammonia (2/98/0.1, v/v) as eluent to give the title compound (0.71 g, yield=48%) as a pale yellow oil.

$[\alpha]_D^{27}$=−28.4°(c 1.67, CHCl$_3$); $^1$H NMR (CDCl$_3$, 400 MHz) δ 1.06(d, J=6.4 Hz, 3H), 1.286, 1.292(pair of t, J=6.8 Hz, 7.3 Hz, 3H), 1.40–2.80(br, 2H, substituted with deuterium oxide), 2.50–2.70 m, 3H), 2.81–2.91(m, 2H), 4.20–4.35(m, 2H), 4.37(d, J=3.9 Hz, 2H), 4.52(brd, J=6.8 Hz, 1H), 4.80(t, J=3.9 Hz, 1H), 6.61–6.71(m, 2H), 6.93(d, J=8.8 Hz, 1H), 7.15–7.30(m, 3H), 7.35 (s, 1H).

Then, the corresponding hydrochloride was obtained as a colorless amorphous solid in a conventional manner.

$^1$H NMR (DMSO-d$_6$, 400 MHz) δ 1.10 (d, J=5.9 Hz, 3H), 1.18(t, J=6.8 Hz, 3H), 2.45–2.61(m, 1H), 3.00–3.50(brm, 4H), 4.15(q, J=6.3 Hz, 2H), 4.28(dd, J=2.4 Hz, 10.5 Hz, 1H), 4.42(dd, J=2.9 Hz, 11.7 Hz, 1H), 5.07(brd, J=9.3 Hz, 1H), 5.15(brs, 1H), 6.37(brs, 1H, substituted with deuterium oxide), 6.75(d, J=12.2 Hz, 1H), 6.77(brs, 1H), 6.91(d, J=7.8 Hz, 1H), 7.32–7.47(m, 3H), 7.49(brs, 1H), 8.82(brs, 1H, substituted with deuterium oxide), 9.37(brs, 1H, substituted with deuterium oxide)

$^{13}$C NMR (DMSO-d$_6$) δ 14.1, 14.7, 37.7, 50.3, 54.9, 61.4, 64.8, 67.8, 71.4, 117.2, 117.7, 122.8, 124.9, 126.0, 127.9, 128.4, 130.5, 133.2, 141.2, 142.9, 144.3, 168.1.

EXAMPLE 21
(2'S,2"R)-6-{2-[2-(3-Chlorophenyl)-2-hydroxyethyl]amino}propyl-2,3-dihydro-1,4-benzodioxin-2-carboxylic acid ethyl ester

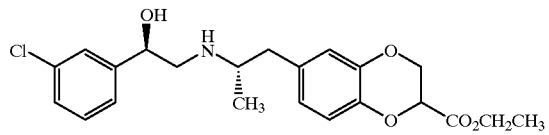

The title compound was obtained as a pale yellow oily substance by using (2'S,5"R)-6-{2-[5-(3-chlorophenyl)-2-oxo-3-oxazolidinyl]}propyl-2,3-dihydro-1,4-benzodioxin-2-carboxylic acid methyl ester according to the same process as described in Example 20. Yield=50%.

$[\alpha]_D^{25}$=−17.9° (c 1.57, CHCl$_3$).

$^1$H NMR (CDCl$_3$, 400 MHz) δ 1.06 (d, J=6.3 Hz, 3H), 1.29(t, J=6.8 Hz, 3H), 1.40–2.45(br, 2H, substituted with deuterium oxide), 2.48–2.70(m, 3H), 2.86(dd, J=6.4 Hz, 13.2 Hz, 1H), 2.96(dd, J=3.4 Hz, 12.2 Hz, 1H), 4.20–4.45 (m, 4H), 4.59(dd, J=3.4 Hz, 8.3 Hz, 1H), 4.80(t, J=3.9 Hz, 1H), 6.61–6.73(m, 2H), 6.91(d, J=8.8 Hz, 1H), 7.16–7.31(m, 3H), 7.34(s, 1H).

Then, the corresponding hydrochloride was obtained as a colorless amorphous solid in a conventional manner.

$^1$H NMR (DMSO-d$_6$, 400 MHz) δ 1.13(d, J=6.3z, 3H), 1.17(t, J=7.3 Hz, 3H), 2.48–2.60(m, 1H), 3.00–3.50(m, 4H), 4.15(q, J=6.4 Hz, 2H), 4.27(dd, J=2.5 Hz, 11.7 Hz, 1H) 4.42(dd, J=2.9 Hz, 11.7 Hz, 1H), 5.06(brd, J=10.3 Hz, 1H), 5.15(t, J=2.9 Hz, 1H), 6.36(d, J=3.9 Hz, 1H, substituted with deuterium oxide), 6.75(d, J=8.3 Hz, 1H), 6.78(s, 1H), 6.90 (d, J=8.3 Hz, 1H), 7.35–7.46(m, 3H), 7.49(s, 1H), 8.76(brs, 1H, substituted with deuterium oxide), 9.42(brs, 1H, substituted with deuterium oxide).

$^{13}$C NMR (DMSO-d$_6$, 400 MHz) δ 14.0, 15.5, 37.1, 50.4, 55.0, 61.4, 64.8, 68.0, 71.4, 79.3, 117.1, 117.7, 122.9, 124.9, 126.0, 127.9, 130.2, 130.5, 133.2, 141.2, 142.8, 144.3, 168.1.

EXAMPLE 22
(2'S,2"S)-6-{2-[2-(3-Chlorophenyl)-2-hydroxyethyl]amino}propyl-2,3-dihydro-1,4-benzodioxin-2-carboxylic acid ethyl ester

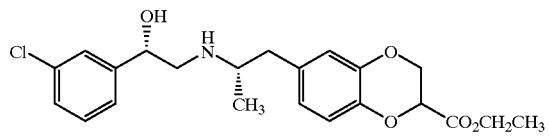

The title compound was obtained as a pale yellow oily substance by using (2'S,5"S)-6-{2-[5-(3-chlorophenyl)-2- oxo-3-oxazolidinyl]}propyl-2,3-dihydro-1,4-benzodioxin-2-carboxylic acid methyl ester according to the same process as described in Example 20. Yield=39%.

$[\alpha]_D^{31}$=+27.0° (c 1.03, CHCl$_3$).

The spectral data were identical with those of Example 20.

Then, the corresponding hydrochloride was obtained as a colorless amorphous solid in a conventional manner.

EXAMPLE 23

(2'R,2"S)-6-{2-[2-(3-Chlorophenyl)-2-hydroxyethyl]amino}propyl-2,3-dihydro-1,4-benzodioxin-2-carboxylic acid ethyl ester

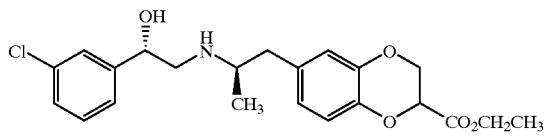

The title compound was obtained as a pale yellow oily substance by using (2'R,5"S)-6-{2-[5-(3-chlorophenyl)-2-oxo-3-oxazolidinyl]}propyl-2,3-dihydro-1,4-benzodioxin-2-carboxylic acid methyl ester according to the same process as described in Example 20. Yield=47%.

$[\alpha]_D^{31}$=+19.4° (c 1.06, CHCl$_3$).

The spectral data were identical with those of Example 21.

Then, the corresponding hydrochloride was obtained as a colorless amorphous solid in a conventional manner.

EXAMPLE 24

(2'R,2"R)-6-[2-(2-Hydroxy-2-phenylethyl)amino]propyl-2,3-dihydro-1,4-benzodioxin-2-carboxylic acid ethyl ester

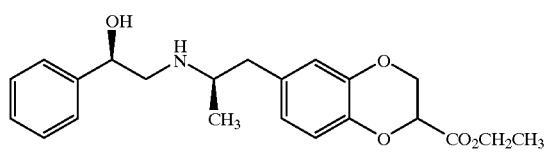

The title compound was obtained as a pale brown oily substance by using (2'R,5"R)-6-{2-[2-oxo-5-phenyl-3-oxazolidinyl]}propyl-2,3-dihydro-1,4-benzodioxin-2-carboxylic acid methyl ester according to the same process as described in Example 20. Yield=39%.

$^1$H NMR (CDCl$_3$, 400 MHz) δ 1.06 (d, J=6.4 Hz, 3H), 1.28(t, J=7.3 Hz, 1.5H), 1.29(t, J=7.3 Hz, 1.5H), 1.60–2.60 (br, 2H, substituted with deuterium oxide), 2.52(dd, J=6.3 Hz, 13.7 Hz, 0.5H), 2.53(dd, J=6.3 Hz, 13.7 Hz, 0.5H), 2.61(dd, J=6.8 Hz, 13.7 Hz, 0.5H), 2.62(dd, J=7.3 Hz, 13.7 Hz, 0.5H), 2.68(dd, J=9.3 Hz, 12.2 Hz, 1H), 2.80–3.00(m, 2H), 4.20–4.34(m, 2H), 4.37(d, J=4.2 Hz, 2H), 4.58(dd, J=2.9 Hz, 7.8 Hz, 1H), 4.80 (t, J=4.4 Hz, 1H), 6.61(m, 2H), 6.92(d, J=8.8 Hz, 1H), 7.20–7.40(m, 5H); $^{13}$C NMR (CDCl$_3$, 400 MHz) δ 14.1, 20.2, 42.9, 54.0, 54.2, 61.9, 64.9, 71.7, 71.9, 117.2, 117.7, 122.8, 122.9, 125.7, 127.4, 128.3, 132.8, 140.7, 142.4, 142.6, 168.0.

Then, the corresponding hydrochloride was obtained as a pale yellow amorphous solid in a conventional manner.

$^1$H NMR (DMSO-d$_6$, 400 MHz) δ 1.10(d, J=6.4 Hz, 3H), 1.18(t, J=7.3 Hz; 3H), 2.45–2.70(m, 1H), 2.98–3.24(m, 3H), 3.27–3.50(m, 1H), 4.15(q, J=6.8 Hz, 2H), 4.27(dd, J=2.9 Hz, 11.7 Hz, 1H), 4.42(dd, J=3.4 Hz, 11.7 Hz, 1H), 5.04(brd, J=9.3 Hz, 1H), 5.15(brs, 1H), 6.22 (brs, 1H, substituted with deuterium oxide), 6.75(d, J=12.2 Hz, 1H), 6.77(s, 1H), 6.91(d, J=8.3 Hz, 1H), 7.28–7.50(m, 5H), 8.78(brs, 1H, substituted with deuterium oxide), 9.36(brs, 1H, substituted with deuterium oxide); $^{13}$C NMR (DMSO-d$_6$) δ 14.0, 14.7, 37.7, 50.6, 54.7, 54.8, 61.4, 64.7, 68.4, 71.4, 117.1, 117.7, 122.8, 126.1, 127.9, 128.4, 128.5, 130.1, 141.1, 141.8, 142.8, 168.0.

EXAMPLE 25

(2'S,2"R)-6-[2-(2-Hydroxy-2-phenylethyl)amino]propyl-2,3-dihydro-1,4-benzodioxin-2-carboxylic acid ethyl ester

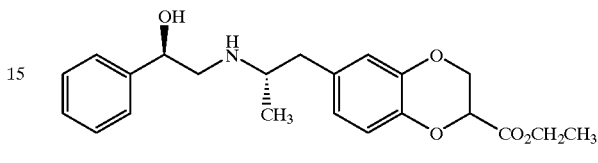

The title compound was obtained as a colorless oily substance by using (2'S,5"R)-6-{2-[2-oxo-5-phenyl-3-oxazolidinyl]}propyl-2,3-dihydro-1,4-benzodioxin-2-carboxylic acid methyl ester according to the same process as described in Example 20. Yield=41%.

$^1$H NMR (CDCl$_3$, 400 MHz) δ 1.06 (d, J=6.3 Hz, 3H), 1.29(t, J=7.3 Hz, 3H), 2.10–3.40(m, 7H, 2H, substituted with deuterium oxide), 4.16–4.50(m, 4H), 4.66(dd, J=3.4 Hz, 8.8 Hz, 1H), 4.79(t, J=4.4 Hz, 1H), 6.60–7.02(m, 3H), 7.20–7.60(m, 5H); $^{13}$C NMR (CDCl$_3$, 400 MHz) δ 14.1, 20.5, 42.7, 54.5, 54.6, 61.9, 64.9, 71.9, 72.2, 117.1, 117.7, 117.8, 122.9, 123.0, 125.7, 127.4, 128.3, 132.8, 140.7, 142.6, 167.9.

Then, the corresponding hydrochloride was obtained as a pale yellow amorphous solid in a conventional manner.

$^1$H NMR (DMSO-d$_6$, 400 MHz) δ 1.13 (d, J=6.4 Hz, 3H), 1.17(t, J=7.3 Hz, 3H), 2.41–2.60(m, 1H), 2.99–3.60(m, 4H), 4.15(q, J=7.3 Hz, 2H), 4.27(dd, J=2.4 Hz, 11.7 Hz, 1H), 4.42(dd, J=3.4 Hz, 12.2 Hz, 1H), 5.03(brd, J=8.8 Hz, 1H), 5.15(brt, J=2.9 Hz, 1H), 6.22(brs, 1H, substituted with deuterium oxide), 6.75(d, J=8.3 Hz, 1H), 6.78(brs, 1H), 6.90(d, J=8.3 Hz, 1H), 7.26–7.50(m, 5H), 8.74(brs, 1H, substituted with deuterium oxide), 9.46(brs, 1H, substituted with deuterium oxide); $^{13}$C NMR (DMSO-d$_6$, 400 MHz) δ 14.0, 15.4, 37.1, 50.7, 54.9, 56.0, 61.4, 64.7, 68.5, 71.4, 117.1, 117.7, 117.8, 122.8, 122.9, 126.1, 127.9, 128.5, 130.2, 141.1, 141.8, 142.8, 168.0.

EXAMPLE 26

(2'S,2"S)-6-[2-(2-Hydroxy-2-phenylethyl)amino]propyl-2,3-dihydro-1,4-benzodioxin-2-carboxylic acid ethyl ester

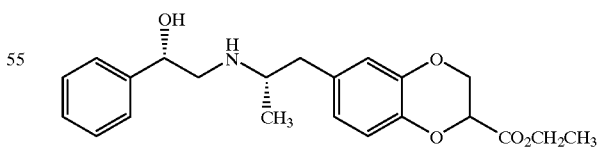

The title compound was obtained as a pale yellow oily substance by using (2'S,5"S)-6-{2-[2-oxo-5-phenyl-3-oxazolidinyl]}propyl-2,3-dihydro-1,4-benzodioxin-2-carboxylic acid methyl ester according to the same process as described in Example 20. Yield=45%.

The spectral data were identical with those of Example 24.

EXAMPLE 27

(2'R,2"S)-6-[2-(2-Hydroxy-2-phenylethyl)amino]propyl-2,3-dihydro-1,4-benzodioxin-2-carboxylic acid ethyl ester

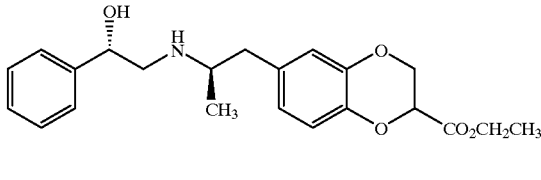

The title compound was obtained as a pale yellow oily substance by using (2'R,5"S)-6-{2-[2-oxo-5-phenyl-3-oxazolidinyl]}propyl-2,3-dihydro-1,4-benzodioxin-2-carboxylic acid methyl ester according to the same process as described in Example 20. Yield=53%.

The spectral data were identical with those of Example 25.

EXAMPLE 28

(2R,2'R,2"R)-6-{2-[2-(3-Chlorophenyl)-2-hydroxyethyl]amino}propyl-2,3-dihydro-1,4-benzodioxin-2-carboxylic acid ethyl ester hydrochloride

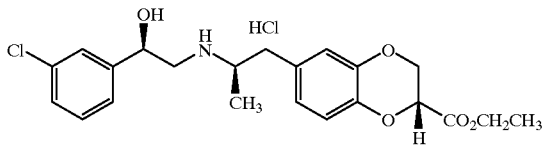

To a solution of (2R,2'R,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester (590 mg) obtained in Preparation Example 58 in ethanol (20 ml) was added concentrated hydrochloric acid (0.14 ml), and the mixture was heated under reflux for 4.5 hours while removing a resulting methanol with Dean-Stark apparatus. The reaction solution was concentrated under reduced pressure, and the residue was recrystallized from ethanol/diethyl ether (3/1, v/v) to give the title compound (393 mg, yield=74%) as colorless crystals.

m.p. 165–168° C. $[\alpha]_D^{29}$=−10.6° (c 1.00, $CH_3CH_2OH$); $^1H$ NMR(DMSO-$d_6$, 400 MHz) δ 1.10(d, J=6.3 Hz, 3H), 1.18(t, J=6.8 Hz, 3H), 2.42–2.60(m, 1H), 2.98–3.23(brm, 3H), 3.28–3.48(m, 1H), 4.15(q, J=6.8 Hz, 2H), 4.27(dd, J=2.9 Hz, 11.7 Hz, 1H), 4.32(dd, J=3.4 Hz, 11.7 Hz, 1H), 5.07(brd, J=10.3 Hz, 1H), 5.15(t, J=2.9 Hz, 1H), 6.36(d, J=3.9 Hz, 1H, substituted with deuterium oxide), 6.75(d, J=9.3 Hz, 1H), 6.76(s, 1H), 6.91(d, J=8.3 Hz, 1H), 7.24–7.46 (m, 3H), 7.49(brs, 1H), 8.81(brs, 1H, substituted with deuterium oxide), 9.35(brs, 1H, substituted with deuterium oxide); $^{13}C$ NMR (DMSO-$d_6$, 400 MHz) δ 14.0, 14.7, 37.7, 50.3, 54.8, 61.4, 64.7, 67.8, 71.4, 117.1, 117.7, 122.7, 124.8, 126.0, 127.8, 130.1, 130.4, 133.2, 141.1, 142.8, 144.3, 168.0.

EXAMPLE 29

(2R,2'S,2"R)-6-{2-[2-(3-Chlorophenyl)-2-hydroxyethyl]amino}propyl-2,3-dihydro-1,4-benzodioxin-2-carboxylic acid ethyl ester

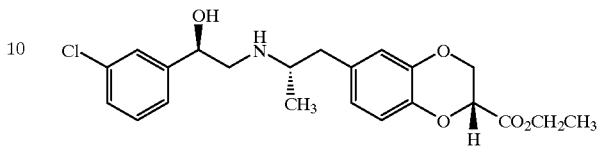

To a solution of (2R,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester (530 mg) obtained in Preparation Example 58 in ethanol (20 ml) was added concentrated hydrochloric acid (0.13 ml), and the mixture was heated under reflux for 5 hours while removing a resulting methanol with Dean-Stark apparatus. The reaction solution was concentrated under reduced pressure, and the residue was dissolved in ethyl acetate (50 ml). The solution was washed in turn with saturated aqueous solution of sodium hydrogencarbonate (10 ml) and saturated aqueous sodium chloride (10 ml), dried over sodium sulfate, and the solvent was distilled off under reduced pressure. The residue was subjected to a silica gel column chromatography (silica gel 30 g) to give the title compound (346 mg, yield=79%) as a colorless oil from the fraction of ethanol/ethyl acetate/aqueous ammonia (2/98/0.1, v/v).

$[\alpha]_D^{29}$=−5.8° (c 1.03, $CHCl_3$); $_1H$ NMR ($CDCl_3$, 400 MHz) δ 1.06(d, J=6.3 Hz, 3H), 1.29(t, J=6.8 Hz, 3H), 2.52(dd, J=6.3 Hz, 13.7 Hz, 1H), 2.57(dd, J=8.8 Hz, 12.2 Hz, 1H), 2.61(dd, J=6.8 Hz, 13.7 Hz, 1H), 2.86(sixtet, J=6.3 Hz, 1H), 2.96(dd, J=3.4 Hz, 12.2 Hz, 1H), 4.20–4.32(m, 2H), 4.33–4.41(m, 2H), 4.59(dd, J=3.4 Hz, 8.3 Hz, 1H), 4.79(t, J=3.9 Hz, 1H), 6.66(d, J=6.8 Hz, 1H), 6.66(d, J=1.5 Hz, 1H), 6.91(d, J=8.8 Hz, 1H), 7.18–7.28(m, 3H), 7.34(s, 1H).

Then, the corresponding hydrochloride was obtained as a colorless amorphous solid in a conventional manner.

$[\alpha]_D^{29}$=+3.3° (c 1.05, $CH_3CH_2OH$); $^1H$ NMR (DMSO-$d_6$, 400 MHz) δ 1.12(d, J=6.3 Hz, 3H), 1.17(t, J=6.8 Hz, 3H), 2.49–2.56(m, 1H), 2.99–3.57(m, 4H), 4.14(q, J=7.3 Hz, 2H), 4.27(dd, J=2.4 Hz, 11.7 Hz, 1H), 4.41(dd, J=3.4 Hz, 11.7 Hz, 1H), 5.05(brd, J=7.8 Hz, 1H), 5.15(brt, J=3.0 Hz, 1H), 6.20–6.70(brs, 1H, substituted with deuterium oxide), 6.74 (d, J=8.3 Hz, 1H), 6.78(s, 1H), 6.90(d, J=8.3 Hz, 1H), 7.34–7.46(m, 3H), 7.49(s, 1H), 8.75(brs, 1H, substituted with deuterium oxide), 9.38(brs, 1H, substituted with deuterium oxide); $^{13}C$ NMR (DMSO-$d_6$, 400 MHz) δ 14.0, 15.4, 37.0, 50.3, 55.0, 61.4, 64.8, 67.9, 71.4, 117.1, 117.7, 122.9, 124.9, 126.0, 127.8, 130.1, 130.4, 133.2, 141.1, 142.8, 144.3, 168.1.

EXAMPLE 30
(2S,2'R,2"R)-6-{2-[2-(3-Chlorophenyl)-2-hydroxyethyl]amino}propyl-2,3-dihydro-1,4-benzodioxin-2-carboxylic acid ethyl ester

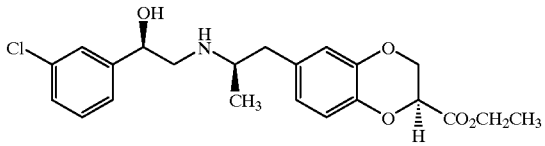

The title compound was obtained as a colorless oily substance by using (2S,2'R,2"R)-6-{2-[(N-tert-butoxycarbonyl-(2-(3-chlorophenyl)-2-hydroxymethyl]amino}propyl-2,3-dihydro-1,4-benzodioxin-2-carboxylic acid methyl ester obtained in Preparation Example 59 according to the same process as described in Example 29. Yield=79%.

$[\alpha]_D^{29}$=−44.7° (c 1.05, CHCl$_3$); $^1$H NMR (CDCl$_3$, 400 MHz) δ 1.09(d, J=6.3 Hz, 3H), 1.29(t, J=7.3 Hz, 3H), 2.56(dd, J=6.3 Hz, 13.7 Hz, 1H), 2.62(dd, J=6.3 Hz, 11.7 Hz, 1H), 2.64(dd, J=9.3 Hz, 12.2 Hz, 1H), 2.80–2.92(m, 2H), 4.20–4.32(m, 2H), 4.37(d, J=4.4 Hz, 2H), 4.56(dd, J=3.4 Hz, 9.4 Hz, 1H), 4.80(t, J=3.9 Hz, 1H), 6.68(s, 1H), 6.70(dd, J=2.0 Hz, 6.3 Hz, 1H), 6.93(d, J=8.8 Hz, 1H), 7.17–7.30(m, 3H), 7.36(s, 1H).

Then, the corresponding hydrochloride was obtained in a conventional manner, and recrystallized from ethanol to give colorless crystals.

m.p. 186–188° C. $[\alpha]_D^{27}$=−51.8° (c 1.01, CH$_3$CH$_2$OH); $^1$H NMR (DMSO-d$_6$, 400 MHz) δ 1.10(d, J=5.9 Hz, 3H), 1.17(t, J=6.8 Hz, 3H), 2.47–2.61(m, 1H), 3.00–3.25(m, 3H), 3.30–3.42(m, 1H), 4.15(q, J=6.8 Hz, 2H), 4.28(dd, J=1.7 Hz, 10.3 Hz, 1H), 4.42(dd, J=2.4 Hz, 11.7 Hz, 1H), 5.07(brd, J=10.3 Hz, 1H), 5.15 (brt, J=3.0 Hz, 1H), 6.36(brd, J=3.9 Hz, 1H, substituted with deuterium oxide), 6.74(d, J=8.8 Hz, 1H), 6.77(s, 1H), 6.91 (d, J=8.3 Hz, 1H), 7.35–7.46(m, 3H), 7.49 (s, 1H), 8.81(brs, 1H, substituted with deuterium oxide), 9.35(brs, 1H, substituted with deuterium oxide); $^{13}$C NMR (DMSO-d$_6$, 400 MHz) δ 14.1, 14.8, 37.8, 50.3, 54.9, 61.4, 64.8, 57.9, 71.5, 117.2, 117.7, 122.9, 124.9, 126.0, 127.9, 130.2, 130.5, 133.3, 141.3, 142.9, 144.3, 168.1.

EXAMPLE 31
(2S,2'S,2"R)-6-{2-[2-(3-Chlorophenyl)-2-hydroxyethyl]amino}propyl-2,3-dihydro-1,4-benzodioxin-2-carboxylic acid ethyl ester

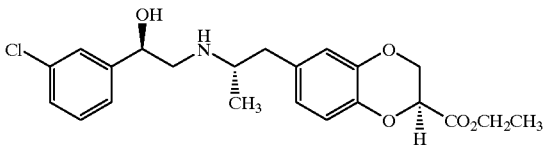

The title compound was obtained as a colorless oily substance by using (2S,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester obtained in Preparation Example 59 according to the same process as described in Example 29. Yield=70%.

$[\alpha]_D^{27}$=−37.2° (c 1.04, CHCl$_3$); $^1$H NMR (CDCl$_3$, 400 MHz) δ 1.06(d, J=6.3 Hz, 3H), 1.29(t, J=7.3 Hz, 3H), 2.52(dd, J=6.3 Hz, 13.2 Hz, 1H), 2.55(dd, J=3.4 Hz, 8.8 Hz, 1H), 2.61(dd, J=6.8 Hz, 13.7 Hz, 1H), 2.86(sixtet, J=6.3 Hz, 1H), 2.96(dd, J=3.4 Hz, 12.2 Hz, 1H), 4.20–4.33(m, 2H), 4.34–4.41(m, 2H), 4.59(dd, J=3.4 Hz, 8.8 Hz, 1H), 4.79(t, J=4.4 Hz, 1H), 6.60–6.71(m, 2H), 6.91(d, J=8.3 Hz, 1H), 7.15–7.30(m, 3H), 7.34(s, 1H).

Then, the corresponding hydrochloride was obtained as a colorless amorphous solid in a conventional manner.

$[\alpha]_D^{29}$=−35.5° (c 1.00, CH$_3$CH$_2$OH); $^1$H NMR (DMSO-d$_6$, 400 MHz) δ0 1.13 (d, J=6.3 Hz, 3H), 1.17(d, J=6.8 Hz, 3H), 2.45–2.60(m, 1H), 3.00–3.50(m, 4H), 4.15(q, J=6.8 Hz, 2H), 4.27(dd, J=2.4 Hz, 11.7 Hz, 1H), 4.42(dd, J=3.4 Hz, 12.2 Hz, 1H), 5.04(brd, J=9.8 Hz, 1H), 5.15 (t, J=2.9 Hz, 1H), 6.36(brd, J=3.3 Hz, 1H, substituted with deuterium oxide), 6.75(d, J=8.8 Hz, 1H), 6.77(s, 1H), 6.90(d, J=7.8 Hz, 1H), 7.35–7.47(m, 3H), 7.49(s, 1H), 8.74(brs, 1H, substituted with deuterium oxide), 9.35(brs, 1H, substituted with deuterium oxide); $^{13}$C NMR (DMSO-d$_6$, 400 MHz) δ 14.1, 15.5, 37.1, 50.3, 55.0, 61.5, 64.8, 68.0, 71.5, 117.2, 117.9, 122.9, 124.9, 126.1, 128.0, 130.1, 130.5, 133.3, 141.2, 142.9, 144.3, 168.2.

EXAMPLE 32
(2S,2'R,2"R)-6-{2-[2-(3-Chlorophenyl)-2-hydroxyethyl]amino}propyl-2,3-dihydro-1,4-benzodioxin-2-carboxylic acid hydrochloride

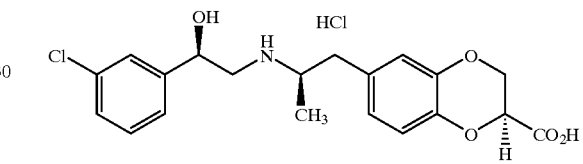

To a solution of (2S,2'R,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid ethyl ester (390 mg) obtained in Preparation Example 61 in ethanol (5 ml) was added concentrated hydrochloric acid (0.11 ml), and the mixture was heated under reflux for 30 minutes. Then water (25 ml) was added, and the mixture was heated under reflux for 12 hours while removing ethanol with Dean-Stark apparatus. The reaction solution was concentrated under reduced pressure, and the residue was subjected to a reverse phase medium pressure column chromatography (ODS AM 120-S50, 40 g, available from YMC). After collecting the fraction of acetonitrile/water (30/70, v/v), to this fraction was added concentrated hydrochloric acid (1 ml). The solvent was distilled off under reduced pressure to give the title compound (169 mg, yield=53%) as a colorless amorphous solid.

$[\alpha]_D^{29}$=−51.4° (c 0.40, 1,4-dioxane/water, 1/1, v/v); $^1$H NMR (DMSO-d$_6$, 400 MHz) δ 1.10(d, J=6.3 Hz, 3H), 2.47–2.60(m, 1H), 3.07(brt, J=11.2 Hz, 1H), 3.12–3.22(brm, 1H), 3.28–3.48(brm, 2H), 4.25(dd, J=2.9 Hz, 11.7 Hz, 1H), 4.40(dd, J=3.4 Hz, 11.7 Hz, 1H), 5.01(t, J=3.4 Hz, 1H), 5.05(brd, J=8.3 Hz, 1H), 6.36(brs, 1H, substituted with deuterium oxide), 6.73(dd, J=2.0 Hz, 8.3 Hz, 1H), 6.76(d, J=2.0 Hz, 1H), 5.89(d, J=8.3 Hz, 1H), 7.35–7.46(m, 3H), 7.49(s, 1H), 8.65–8.90(br, 1H, substituted with deuterium oxide), 9.25–9.40(br, 1H, substituted with deuterium oxide), 13.1–13.6(br, 1H, substituted with deuterium oxide); $^{13}$C NMR (DMSO-d$_6$, 400 MHz) δ 14.7, 37.7, 50.2, 54.8, 64.8, 67.8, 71.3, 117.1, 117.6, 122.7, 124.8, 126.0, 127.8, 129.9, 130.4, 133.2, 141.3, 142.9, 144.3, 169.5.

EXAMPLE 33

(2S,2'S,2"R)-6-{2-[2-(3-Chlorophenyl)-2-hydroxyethyl] amino}propyl-2,3-dihydro-1,4-benzodioxin-2-carboxylic acid hydrochloride

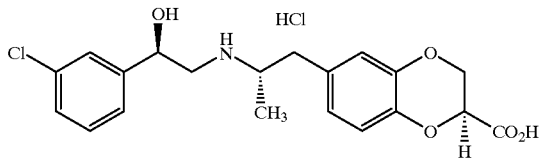

The title compound was obtained as a colorless amorphous solid by using (2S,2'S,2"R)-6-{2-[(N-tert-butoxycarbonyl-(2-(3-chlorophenyl)-2-hydroxy)ethyl] amino}propyl-2,3-dihydro-1,4-benzodioxin-2-carboxylic acid ethyl ester obtained in Preparation Example 61 according to the same process as described in Example 32. Yield= 19%.

$[\alpha]_D^{29}$=−34.0° (c 0.57, 1,4-dioxane/water, 1/1, v/v); $^1$H NMR (DMSO-d$_6$, 400 MHz) δ 1.13(d, J=6.8 Hz, 3H), 2.45–2.56(m, 1H), 3.00–3.30(m, 1H), 3.32–3.45(brm, 1H), 4.25(dd, J=2.9 Hz, 11.7 Hz, 1H), 4.40(dd, J=3.4 Hz, 11.7 Hz, 1H), 5.00–5.10(m,2H), 6.35(brs, 1H, substituted with deuterium oxide), 6.74(dd, J=1.5Hz, 8.3 Hz, 1H), 6.77(d, J=1.5 Hz, 1H), 6.88(d, J=8.3 Hz, 1H), 7.35–7.48(m, 3H), 7.49(s, 1H), 8.72(brs, 1H, substituted with deuterium oxide), 9.29 (brs, 1H, substituted with deuterium oxide), 13.35(brs, 1H, substituted with deuterium oxide); $^{13}$C NMR (DMSO-d$_6$, 400 MHz) δ 15.5, 37.0, 50.2, 55.0, 64.8, 67.9, 71.3, 117.1, 117.8, 122.7, 124.9, 126.0, 127.9, 129.9, 130.4, 133.2, 141.3, 142.9, 144.3, 169.5.

EXAMPLE 34

(2R,2'R,2"R)-6-{2-[2-(3-Chlorophenyl)-2-hydroxyethyl] amino}propyl-2,3-dihydro-1,4-benzodioxin-2-carboxylic acid hydrochloride

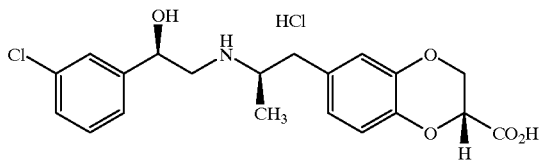

The title compound was obtained as a colorless amorphous solid by using (2R,2'R,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid ethyl ester obtained in Preparation Example 60 according to the same process as described in Example 32. Yield=45%.

$[\alpha]_D^{28}$=−13.0° (c 0.84, 1,4-dioxane/water, 1/1, v/v); $^1$H NMR (DMSO-d$_6$, 400 MHz) δ 1.11 (d, J=6.3 Hz, 3H), 2.45–2.60(m, 1H), 3.00–3.25(brm, 3H), 3.30–3.60(brm, 1H), 4.25(dd, J=2.4 Hz, 11.7 Hz, 1H), 4.41(dd, J=3.4 Hz, 11.7 Hz, 1H), 5.02(t, J=2.9 Hz, 1H), 5.05(d, J=13.2 Hz, 1H), 6.36(brs, 1H, substituted with deuterium oxide), 6.74(brd, J=8.8 Hz, 1H), 6.76(brs, 1H), 6.89(d, J=8.3 Hz, 1H), 7.35–7.47(m, 3H), 7.49(s, 1H), 8.79(brs, 1H, substituted with deuterium oxide), 9.27(brs, 1H, substituted with deuterium oxide), 13.38(brs, 1H, substituted with deuterium oxide); $^{13}$C NMR (DMSO-d$_6$, 400 MHz) δ 14.7, 37.7, 50.2, 54.8, 64.8, 67.8, 71.2, 117.1, 117.7, 122.6, 124.8, 125.9, 127.8, 129.9, 130.4, 133.2, 141.3, 142.8, 144.3, 169.4.

EXAMPLE 35

(2R,2'S,2"R)-6-{2-[2-(3-Chlorophenyl)-2-hydroxyethyl] amino}propyl-2,3-dihydro-1,4-benzodioxin-2-carboxylic acid hydrochloride

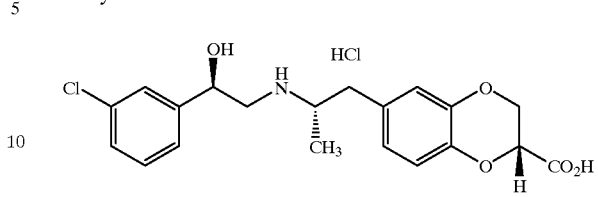

The title compound was obtained as a colorless amorphous solid by using (2R,2'S,2"R)-6-{2-[(N-tert-butoxycarbonyl-(2-(3-chlorophenyl)-2-hydroxy)ethyl] amino}propyl-2,3-dihydro-1,4-benzodioxin-2-carboxylic acid ethyl ester obtained in Preparation Example 60 according to the same process as described in Example 32. Yield= 46%.

$[\alpha]_D^{28}$=+4.2° (c 0.62, 1,4-dioxane/water, 1/1, v/v) $^1$H NMR (DMSO-d$_6$, 400 MHz) δ 1.12(d, J=6.8 Hz, 3H), 2.45–2.59(m, 1H), 3.00–3.48(m, 4H), 4.25(dd, J=2.4 Hz, 11.7 Hz, 1H), 4.40(dd, J=3.4 Hz, 11.7 Hz, 1H), 5.00–5.08(m, 2H), 6.36(brs, 1H, substituted with deuterium oxide), 6.73 (brd, J=7.8 Hz, 1H), 6.77(brs, 1H), 6.88(d, J=7.8 Hz, 1H), 7.35–7.46(m, 3H), 7.49 (s, 1H), 8.71(brs, 1H, substituted with deuterium oxide), 9.29(brs, 1H, substituted with deuterium oxide), 13.40(brs, 1H, substituted with deuterium oxide); $^{13}$C NMR (DMSO-d$_6$, 400 MHz) δ 15.5, 37.0, 50.2, 55.0, 64.8, 68.0, 71.2, 117.1, 117.7, 122.8, 124.9, 126.0, 127.9, 129.9, 130.5, 133.2, 141.3, 142.9, 144.3, 169.5.

Preparation Example 1

2-Amino-1-(3-methoxyphenyl)ethanol

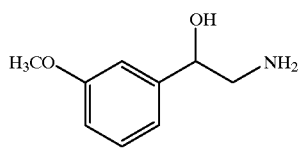

To a solution of 3-methoxybenzaldehyde (2.72 g) in dichloromethane (100 ml) was added zinc iodide (0.12 g), and ice-cooled. A solution of cyanotrimethylsilane (2.39 g) in dichloromethane (20 ml) was added dropwise over a period of 20 minutes, and the mixture was stirred at room temperature for 2 hours. The solvent was distilled off under reduced pressure, and the residue was dissolved in tetrahydrofuran (200 ml). After lithium aluminum hydride (0.81 g) was added under ice-cooling, the mixture was heated under reflux for 2 hours. The reaction solution was ice-cooled, and an excess reagent was inactivated by saturated aqueous solution of sodium sulfate, and then the solution was filtered with Celite. The solvent was distilled off under reduced pressure. The residue was chromatographed over silica gel (80 g) with 1% aqueous ammonia/10% methanol/chloroform (v/v) as eluent to give the title compound (1.93 g, yield=58%) as colorless crystals.

$^1$H NMR (CDCl$_3$, 400MHz) δ 2.80(dd, J=7.8 Hz, 12.7 Hz, 1H), 2.97(dd, J=3.9 Hz, 12.7 Hz, 1H), 3.80(s, 3H), 4.60(dd, J=3.9 Hz, 7.8 Hz, 1H), 6.79–6.82(m, 1H), 6.90–6.92(m, 2H), 7.23–7.27(m, 1H).

Preparation Example 2
2-Amino-1-(3-tolyl)ethanol

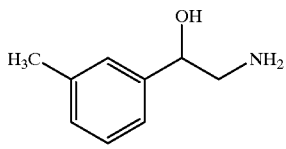

The title compound was obtained as colorless crystals by using 3-methylbenzaldehyde according to the same process as described in Preparation Example 1. Yield=89%.

$^1$H NMR (CDCl$_3$, 400 MHz) δ 2.53(s, 3H), 2.82(dd, J=7.8 Hz, 12.7 Hz, 1H), 3.01(dd, J=3.9 Hz, 12.7 Hz, 1H), 4.63(dd, J=3.9 Hz, 7.8 Hz, 1H), 7.08–7.23(m, 4H)

Preparation Example 3
2-Amino-1-piperonylethanol

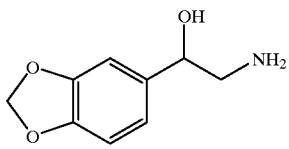

The title compound was obtained as a yellow oily substance by using piperonal according to the same process as described in Preparation Example 1. Yield=92%. A part of the compound was recrystallized from ethyl acetate-normal hexane, and the spectral data was measured.

m.p. 85–89° C.; $^1$H NMR (CDCl$_3$, 400 MHz) δ 1.80–2.30 (br, 2H, substituted with deuterium oxide), 2.76(dd, J=8.3 Hz, 12.7 Hz, 1H), 2.93(dd, J=3.9 Hz, 12.7 Hz, 1H), 4.53(dd, J=3.9 Hz, 7.8 Hz, 1H), 5.94(s, 2H), 6.77(d, J=7.8 Hz, 1H), 6.80(dd, J=1.0 Hz, 8.3 Hz, 1H), 6.86(s, 1H).

Then, the corresponding hydrochloride was obtained as colorless crystals in a conventional manner. m.p. 182–185° C. (recrystallized from methanol); $^1$H NMR (D$_2$O, 400 MHz, internal standard substance: sodium 3-trimethylsilylpropanesulfonate) δ 3.21(dd, J=8.3 Hz, 13.2 Hz, 1H), 3.27(dd, J=4.4 Hz, 13.2 Hz, 1H), 4.92(dd, J=4.4 Hz, 8.3 Hz, 1H), 6.00(s, 2H), 6.93(s, 2H), 6.97(s, 1H).

Preparation Example 4
2-Amino-1-[3-(4-chlorophenoxy)phenyl]ethanol

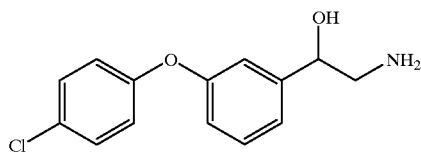

The title compound was obtained as colorless crystals by using 3-(4-chlorophenoxy)benzaldehyde according to the same process as described in Preparation Example 1. Yield=57%.

m.p. 86.5–87.5° C.; $^1$H NMR (CDCl$_3$, 400 MHz) δ 0.91–2.40(br, 2H, substituted with deuterium oxide), 2.76 (dd, J=7.3 Hz, 12.7 Hz, 1H), 3.02(dd, J=3.9 Hz, 12.7 Hz, 1H), 4.60(dd, J=3.9 Hz, 7.8 Hz, 1H), 6.89(dd, J=2.4 Hz, 8.3 Hz, 1H), 6.90–6.97(m, 1H), 6.94(d, J=9.3 Hz, 1H), 7.02(s, 1H), 7.10(d, J=7.3 Hz, 1H), 7.23–7.35(m, 3H).

Preparation Example 5
2-Amino-1-(4-biphenyl)ethanol

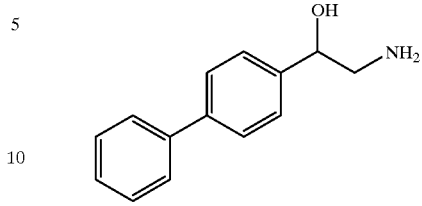

The title compound was obtained as pale orange crystals by using 4-biphenylbenzaldehyde according to the same process as described in Preparation Example 1. Yield=45%.

m.p. 128.5–129.5° C. (recrystallized from ethyl acetate); $^1$H NMR (CDCl$_3$, 400 MHz) δ 1.09–2.40(br, 2H, substituted with deuterium oxide), 2.85(dd, J=7.8 Hz, 12.7 Hz, 1H), 3.04(dd, J=4.4 Hz, 12.7 Hz, 1H), 4.68(dd, J=3.9 Hz, 7.8 Hz, 1H), 7.30–7.66(m, 9H).

Preparation Example 6
2-Amino-1-(3-benzyloxyphenyl)ethanol

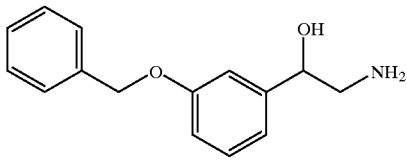

The title compound was obtained as pale brown crystals by using 3-benzyloxybenzaldehyde according to the same process as described in Preparation Example 1. Yield=64%.

m.p. 106–109° C. (recrystallized from ethyl acetate-normal hexane); $^1$H NMR (CDCl$_3$, 400 MHz) δ 1.20–2.20 (br, 3H, substituted with deuterium oxide), 2.79(dd, J=7.8 Hz, 12.7 Hz, 1H), 2.99(dd, J=3.9 Hz, 12.7 Hz, 1H), 4.60(dd, J=6.9 Hz, 7.8 Hz, 1H), 5.07(s, 2H), 6.89(dd, J=2.0 Hz, 8.3 Hz, 1H), 6.93(d, J=7.8 Hz, 1H), 7.02(s, 1H), 7.20–7.46(m, 6H).

Preparation Example 7
2-Amino 1-cyclohexylethanol

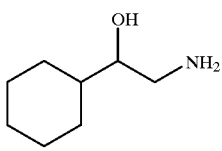

The title compound was obtained as colorless crystals by using cyclohexylcarbaldehyde according to the same process as described in Preparation Example 1. Yield=41%.

m.p. 86–88° C. (recrystallized from ethyl acetate-normal hexane); $^1$H NMR (CDCl$_3$, 400 MHz) δ 0.95–2.10(m, 13H, 3H, substituted with deuterium oxide), 1.88(brd, J=12.7 Hz, 1H), 2.56(dd, J=8.8 Hz, 12.7 Hz, 1H), 2.56(dd, J=8.8 Hz, 12.7 Hz, 1H), 2.88(dd, J=2.9 Hz, 12.7 Hz, 1H), 3.24(ddd, J=2.9 Hz, 6.3 Hz, 9.3 Hz, 1H).

Preparation Example 8

2-Amino-1-(3-chlorophenyl)ethanol

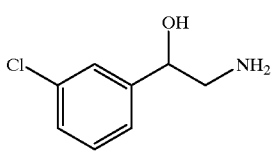

The title compound was obtained as a pale red oily substance by using 3-chlorobenzaldehyde according to the same process as described in Preparation Example 1. Yield= 70%.

$^1$H NMR (CDCl$_3$, 400 MHz) δ 1.86–2.39(brs, 3H, substituted with deuterium oxide), 2.77(dd, J=7.8 Hz, 12.7 Hz, 1H), 3.00(dd, J=3.4 Hz, 12.3 Hz, 1H), 4.61(dd, J=3.9 Hz, 7.8 Hz, 1H), 7.10–7.36(m, 3H), 7.38(s, 1H).

Preparation Example 9

2-Amino-1-(3-trifluoromethylphenyl)ethanol

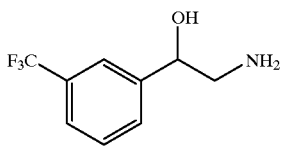

The title compound was obtained as pale brown crystals by using 3-trifluoromethylbenzaldehyde according to the same process as described in Preparation Example 1. Yield= 63%.

m.p. 52–54° C. (recrystallized from ethyl acetate-normal hexane); $^1$H NMR (CDCl$_3$, 400 MHz) δ 1.09–2.90(br, 3H, substituted with deuterium oxide), 2.75(dd, J=7.8 Hz, 12.7 Hz, 1H), 2.97(dd, J=3.4 Hz, 12.7 Hz, 1H), 4.68(dd, J=3.4 Hz, 7.8 Hz, 1H), 7.45(t, J=7.8 Hz, 1H), 7.49–7.57 (m, 2H), 7.62(s, 1H).

Preparation Example 10

2-Amino-1-(4-fluorophenyl)ethanol

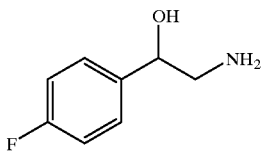

The title compound was obtained as a white solid by using 4-fluorobenzaldehyde according to the same process as described in Preparation Example 1. Yield=14%.

$^1$H NMR (CDCl$_3$, 400 MHz) δ 2.73–2.78(m, 1H), 2.94–2.98(m, 1H), 4.61(q, J=4.0 Hz, 1H), 7.00–7.05(m, 2H), 7.29–7.33(m, 2H).

Preparation Example 11

2-Amino-1-(4-isopropylphenyl)ethanol

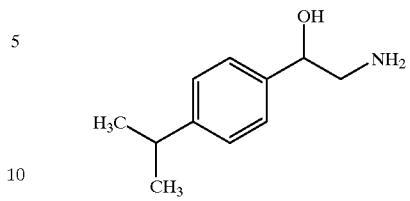

The title compound was obtained as a white solid by using 4-isopropylbenzaldehyde according to the same process as described in Preparation Example 1. Yield=51%.

$^1$H NMR (CDCl$_3$, 400 MHz) δ 1.24(d, J=7.0 Hz, 6H), 2.79–3.00(m, 3H), 4.60(dd, J=4 Hz, 8 Hz, 1H), 7.21(d, J=8.0 Hz, 2H), 7.27(d, J=8.0 Hz, 2H).

Preparation Example 12

3-Amino-1-phenylpropanol

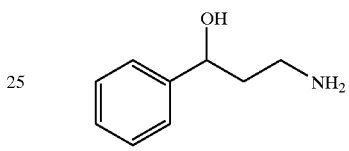

To a solution of benzoylacetonitrile (2.92 g) in tetrahydrofuran (150 ml) was added lithium aluminum hydride (3.03 g) under ice-cooling and the mixture was heated under reflux for 4 hours. The reaction solution was ice-cooled, and an excess reagent was inactivated by a 10% aqueous solution of sodium hydroxide, and then the solution was filtered with Celite. The solvent was distilled off under reduced pressure to give the title compound (2.71 g, yield=90%) as a colorless oily substance.

$^1$H NMR (CDCl$_3$, 400 MHz) δ 1.70–1.89(m, 2H), 2.90–2.96(m, 1H), 3.03–3.12(m, 1H), 4.94(dd, J=3 Hz, 8 Hz, 1H), 7.17–7.38(m, 5H).

Preparation Example 13

2-Cyano-6-formyl-2,3-dihydro-1,4-benzodioxin

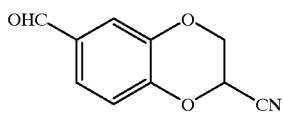

To a solution of 3,4-dihydroxybenzaldehyde (60 g) in acetone (1000 ml) was added potassium carbonate (132.1 g), and ice-cooled. 2-Chloroacrylonitrile (78.8 g) was added dropwise over a period of 30 minutes, and the mixture was stirred at room temperature for 72 hours. The reaction solution was filtered, and the solvent was distilled off under reduced pressure. The residue was diluted with ethyl acetate (500 ml), and washed in turn with refined water (400 ml) and saturated aqueous sodium chloride solution (300 ml). The organic layer was dried over anhydrous magnesium sulfate, and the solvent was distilled off under reduced pressure. The residue was chromatographed over silica gel (350 g) with ethyl acetate/benzene (1/99–1/95, v/v) as eluent to give a pale yellow oily substance (72.16 g, yield=88.4%). The oily substance which was obtained as recrystallized from benzene/normal hexane to give the title compound (66.8 g, yield=81%) as colorless crystals.

m.p. 63–65° C.; $^1$H NMR (CDCl$_3$, 400 MHz) δ 4.41(dd, J=2.4 Hz, 11.7 Hz, 1H), 4.50(dd, J=3.9 Hz, 12.2 Hz, 1H), 5.23(dd, J=2.9 Hz, 3.9 Hz, 1H), 7.11(d, J=8.8 Hz, 1H), 7.500(d, J=2.0 Hz, 1H), 7.502(dd, J=2.0 Hz, 8.8 Hz, 1H), 9.87(s, 1H); $^{13}$C NMR (DMSO-d$_6$, 400 MHz) δ 62.0, 64.5, 114.0, 118.4, 118.9, 124.8, 132.1, 142.6, 145.5, 190.3.

Preparation Example 14

6-Formyl-2,3-dihydro-1,4-benzodioxin-2-carboxylic acid

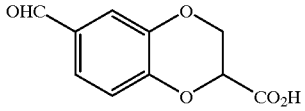

To a solution of 2-cyano-6-formyl-2,3-dihydro-1,4-benzodioxin (47 g) in acetic acid (80 ml) were added refined water (80 ml) and concentrated sulfuric acid (28.4 ml), and the mixture was heated under reflux for 10 hours. The reaction solution was ice-cooled, and the precipitated crystal was filtered out to give the title compound (46.83 g, yield=90%) as colorless crystals.

m.p. 227–227.5° C.; $^1$H NMR (CDCl$_3$, 400 MHz) δ 4.32(dd, J=2.4 Hz, 11.7 Hz, 1H), 4.53(dd, J=2.9 Hz, 11.7 Hz, 1H), 5.20(s, 1H), 7.14(d, J=8.3 Hz, 1H), 7.38(d, J=2.0 Hz, 1H), 7.48(dd, J=2.0 Hz, 8.3 Hz, 1H), 9.81(s, 1H); $^{13}$C NMR (DMSO-d$_6$, 400 MHz) δ 64.9, 71.8, 117.75, 117.83, 124.3, 130.4, 143.5, 148.1, 169.2, 191.4.

Preparation Example 15

6-Formyl-2,3-dihydro-1,4-benzodioxin-2-carboxylic acid methyl ester

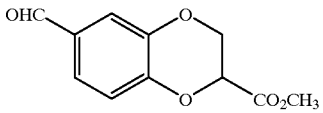

To a solution of 6-formyl-2,3-dihydro-1,4-benzodioxin-2-carboxylic acid (46.83 g) in dimethylformamide (400 ml) was added potassium carbonate (37.3 g), and iodomethane (16.8 ml) was added dropwise under ice-cooling. The mixture was stirred at room temperature for 2.5 hours. The reaction solution was filtered, and the solvent was distilled off under reduced pressure. To the residue was added water (400 ml), and the solution was extracted with ethyl acetate (400 ml×2). The combined organic layer was washed with a saturated aqueous sodium chloride solution, and the solvent was distilled off under reduced pressure. The residue was crystallized from ethyl acetate/hexane, and filtered off. The filtrate was distilled off under reduced pressure. The residue was chromatographed over silica gel (150 g) with ethyl acetate/hexane (1/3–1/2, v/v) as eluent to give a pale yellow oily substance (48.9 g, yield=92%). A part of the oily substance was recrystallized from ethyl acetate-normal hexane to give the title compound as colorless crystals.

m.p. 63–65° C.; $^1$H NMR (CDCl$_3$, 400 MHz) d 3.83(s, 3H), 4.39(dd, J=2.9 Hz, J=11.7 Hz, 1H), 4.48(dd, J=4.4 Hz, 11.7 Hz, 1H), 4.94(dd, J=2.9 Hz, 4.4 Hz, 1H), 7.13(d, J=8.8 Hz, 1H), 7.41(d, J=2.0 Hz, 1H), 7.47(dd, J=2.0 Hz, 8.3 Hz, 1H), 9.84(s, 1H); $^{13}$C NMR (CDCl$_3$, 400 MHz) δ 53.0, 64.7, 72.2, 117.9, 118.3, 124.8, 131.0, 143.3, 147.7, 167.8, 190.6.

Preparation Example 16

6-Acetonyl-2,3-dihydro-1,4-benzodioxin-2-carboxylic acid methyl ester

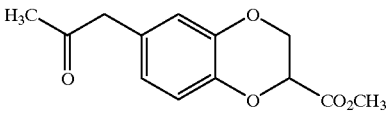

To a solution of 6-formyl-2,3-dihydro-1,4-benzodioxin-2-carboxylic acid methyl ester (48.9 g) in benzene (300 ml) was added cyclohexylamine (30.2 ml), and the mixture was heated under reflux for one hour while removing a resulting water with Dean-Stark apparatus. The solvent was distilled off under reduced pressure, and the residue was dissolved in acetic acid (200 ml). Then nitroethane (40.0 ml) was added, and the mixture was heated at 110° C. for 2.5 hours. The solvent was distilled off under reduced pressure, and the residue was diluted with ethyl acetate (300 ml). The solution was washed in turn with refined water (200 ml×2), saturated aqueous solution of sodium hydrogencarbonate (200 ml×2) and saturated aqueous sodium chloride (200 ml). The organic layer was dried over anhydrous magnesium sulfate, and the solvent was distilled off under reduced pressure to give a brown oily substance (67.16 g).

To a solution of the oily substance (67.16 g) which was obtained in methanol (315 ml) were added refined water (90 ml) and iron powder (67.22 g), acetic acid (405 ml) was added dropwise over a period of 30 minutes under reflux-heating, and the mixture was heated under reflux for further one hour. After the reaction solution was ice-cooled, concentrated hydrochloric acid (90 ml) was added, and the solution was filtered with Celite. The solvent was distilled off under reduced pressure. To the residue was added water (400 ml), the solution was filtered with Celite, and extracted with chloroform (300 ml×2). The combined organic layer was washed in turn with refined water (300 ml×2), saturated aqueous solution of sodium hydrogencarbonate (200 ml×2) and saturated aqueous sodium chloride (200 ml), and dried over anhydrous magnesium sulfate. The solvent was distilled off under reduced pressure, and the crude crystals which were obtained were recrystallized from ethyl acetate/hexane to give the title compound (29.65 g, 53%) as pale pink crystals.

m.p. 74–75° C. (recrystallized from ethyl acetate-normal hexane); $^1$H NMR (CDCl$_3$, 400 MHz) δ 2.14(s, 3H), 3.58(s, 2H), 3.81(s, 3H), 4.37(d, J=2.9 Hz, 2H), 4.84(t, J=3.9 Hz, 1H), 6.69–6.76(m, 2H), 6.96(d, J=8.8 Hz, 1H); $^{13}$C NMR (CDCl$_3$, 400 MHz) δ 29.2, 50.1, 52.7, 64.8, 71.9, 117.5, 118.1, 123.1, 127.8, 141.2, 142.8, 168.3, 206.4.

Preparation Example 17

6-Acetonyl-2,3-dihydro-1,4-benzodioxin-2-carboxylic acid ethyl ester

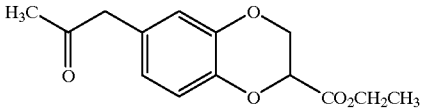

To a solution of 6-acetonyl-2,3-dihydro-1,4-benzodioxin-2-carboxylic acid methyl ester (1.0 g) in ethanol (100 ml) was added concentrated sulfuric acid (0.5 ml) and the mixture was heated under reflux for 2 hours. The solvent was distilled off under reduced pressure, and the residue was dissolved in ethyl acetate (50 ml), the solution was washed in turn with refined water (100 ml×2) and saturated aqueous sodium chloride solution (50 ml). The organic layer was dried over anhydrous sodium sulfate, and the solvent was distilled off under reduced pressure to give the title compound 1.07 g (100%) as a pale yellow oily substance.

$^1$H NMR (CDC13, 400 MHz) δ 1.29(t, J=7.3 Hz, 3H), 2.14(s, 3H), 3.59(s, 2H), 4.24–4.30(m, 2H), 4.37(d, J=3.9 Hz, 2H), 4.80(t, J=3.9 Hz, 1H), 6.69–6.76(m, 2H), 6.96(d, J=8.8 Hz, 1H).

Preparation Example 18

6-Formyl-2,3-dihydro-1,4-benzodioxin-2-carboxylic acid ethyl ester and 7-Formyl-2,3-dihydro-1,4-benzodioxin-2-carboxylic acid ethyl ester

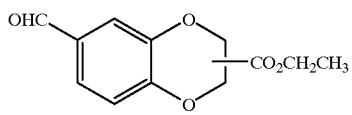

To a solution of 3,4-dihydroxybenzaldehyde (30 g) in acetone (1000 ml) were added ethyl 2,3-dibromopropionate (58 g) and potassium carbonate (60 g), and the mixture was heated under reflux for 3 hours. The reaction solution was filtered, and the solvent was distilled off under reduced pressure. The residue was diluted with ethyl acetate (500 ml), and washed in turn with 1N aqueous solution of sodium hydroxide (150 ml×2), refined water (150 ml×2) and saturated aqueous sodium chloride solution (150 ml). The organic layer was dried over anhydrous sodium sulfate, and concentrated under reduced pressure. The residue was chromatographed over silica gel (200 g) with 30% ethyl acetate-:hexane (v/v) as eluent to give regioisomers mixture (25.7 g, yield=50%, 40:60) of the title compounds as a colorless oily substance.

MS (EI) 264, 163; $^1$H NMR (CDCl$_3$, 400 MHz) δ 1.26–1.34(m, 3H), 4.24–4.31(m, 2H), 4.37–4.49(m, 2H), 4.88(dd, J=2.9 Hz, 4.3 Hz, 0.4H), 4.91(dd, J=2.9 Hz, 4.3 Hz, 0.6H), 7.00(d, J=8.3 Hz, 0.4H), 7.13(d, J=8.3 Hz, 0.6H), 7.45–7.54(m, 2H), 9.84(s, 0.4H), 9.85(s, 0.6H).

Preparation Example 19

6-Acetonyl-2,3-dihydro-1,4-benzodioxin-2-carboxylic acid ethyl ester and 7-Acetonyl-2,3-dihydro-1,4-benzodioxin-2-carboxylic acid ethyl ester

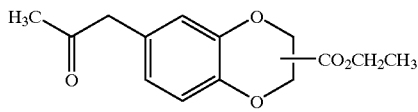

The title compounds were obtained as a pale yellow oily substance by using the mixture of 6-formyl-2,3-dihydro-1,4-benzodioxin-2-carboxylic acid ethyl ester and 7-formyl-2,3-dihydro-1,4-benzodioxin-2-carboxylic acid ethyl ester which were obtained in Preparation Example 18 according to the same process as described in Preparation Example 16. Yield=43%.

MS (EI) 264, 221; $^1$H NMR (CDCl$_3$, 400 MHz) δ 1.29 (t, J=7.0 Hz, 3H), 2.14(s, 3H), 3.58–3.59(m, 2H), 4.24–4.29(m, 2H), 4.37–4.38(m, 2H), 4.79–4.82(m, 1H), 6.70–6.97(m, 3H).

Preparation Example 20

N-Phenethyl-7-formyl-2,3-dihydro-1,4-benzodioxin-2-carboxamide

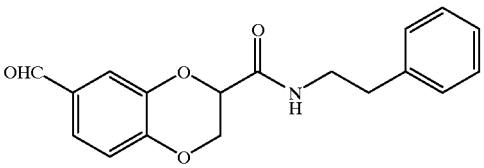

To a solution of the mixture (20 g) of 6-formyl-2,3-dihydro-1,4-benzodioxin-2-carboxylic acid ethyl ester and 7-formyl-2,3-dihydro-1,4-benzodioxin-2-carboxylic acid ethyl ester which were obtained in Preparation Example 18 in xylene (100 ml) was added 2-phenethylamine (31.8 ml), and the mixture was heated under reflux at 160° C. for 3 hours while removing a resulting ethanol with Dean-Stark apparatus. After the reaction solution was ice-cooled, 5N aqueous solution of hydrochloric acid (100 ml) was added, and extracted with ethyl acetate (400 ml×3). The organic layers were combined, and the solvent was distilled off under reduced pressure. The residue was chromatographed over silica gel (150 g) with 30% ethyl acetate:hexane (v/v) as eluent to give regioisomers mixture (23.4 g, yield=89%) of the amide as a pale yellow oily substance.

The oily substance was chromatographed by medium-pressure silica gel column chromatography with 30% ethyl acetate: hexane (v/v) as eluent to give the title compound (yield=18%) as a low polar and colorless oily substance.

$^1$H NMR (CDCl$_3$, 400 MHz) δ 2.77–2.87(m, 2H), 3.50–3.58(m, 1H), 3.60–3.67(m, 1H), 4.27(dd, J=6.8 Hz, 11.7 Hz, 1H), 4.55(dd, J=2.9, 11.7 Hz, 1H), 4.69(dd, J=2.9 Hz, 6.8 Hz, 1H), 6.56(brs, 1H), 7.04(d, J=8.3 Hz, 1H), 7.11(d, J=6.8 Hz, 2H), 7.22–7.29(m, 3H), 7.40–7.60(m, 2H), 9.84(s, 1H).

Preparation Example 21

7-Formyl-2,3-dihydro-1,4-benzodioxin-2-carboxylic acid ethyl ester

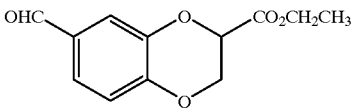

To a solution of N-phenethyl-7-formyl-2,3-dihydro-1,4-benzodioxin-2-carboxamide (2.42 g) in acetic acid (50 ml) was added concentrated hydrochloric acid (15 ml), and the mixture was heated under reflux for 7 hours. After that, concentrated hydrochloric acid (15 ml) was added, and the mixture was further heated under reflux for 13 hours. The reaction solution was ice-cooled, refined water (200 ml) was added, and extracted with ethyl acetate (150 ml×2). The solvent was distilled off under reduced pressure. The residue was dissolved in ethanol (100 ml), benzene (100 ml) and concentrated sulfuric acid (0.2 ml) were added, and the mixture was heated under reflux for 1.5 hours while removing a resulting water with Dean-Stark apparatus. The reaction solution was ice-cooled, diluted with ethyl acetate (200 ml), and washed with refined water (200 ml×3). The organic layer was dried over anhydrous sodium sulfate, and the solvent was distilled off under reduced pressure to give the title compound (1.44 g, yield=78%) as a pale yellow oily substance.

$^1$H NMR (CDCl$_3$, 400 MHz) δ 1.28(t, J=7.3 Hz, 3H), 4.23–4.31(m, 2H), 4.43(dd, J=2.9 Hz, 11.2 Hz, 1H), 4.50(dd,

J=4.4 Hz, 11.7 Hz, 1H), 4.88(dd, J=2.9 Hz, 4.4 Hz, 1H), 7.00(d, J=8.3 Hz, 1H), 7.44(dd, J=1.9 Hz, 8.3 Hz, 1H), 7.54(d, J=1.9 Hz, 1H), 9.84(s, 1H).

Preparation Example 22
7-Acetonyl-2,3-dihydro-1,4-benzodioxin-2-carboxylic acid ethyl ester

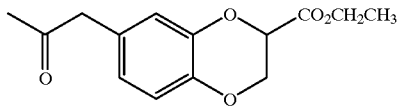

The title compound was obtained as a pale yellow oily substance by using 7-formyl-2,3-dihydro-1,4-benzodioxin-2-carboxylic acid ethyl ester according to the same process as described in Preparation Example 16. Yield=53%.

$^1$H NMR (CDCl$_3$, 400 MHz) δ 1.29(t, J=7.3 Hz, 3H), 2.14(s, 3H), 3.59(s, 2H), 4.24–4.30(m, 2H), 4.37(d, J=3.9 Hz, 2H), 4.81(t, J=3.9 Hz; 1H), 6.69(d, J=8.3 Hz, 1H), 6.70–6.86(m, 2H).

Preparation Example 23
(R)-(−)-1-(3'-Chlorophenyl)-1,2-ethanediol

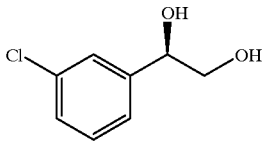

To a suspension of lithium aluminum hydride (3.26 g) in tetrahydrofuran (100 ml) was added (R)-3'-chloromandelic acid (5.0 g, available from Nittou Chemical Industry), and the mixture was heated under reflux for 2 hours. The reaction solution was ice-cooled, and an excess reagent was inactivated by aqueous ammonia, and then the precipitated insolubles were filtered out. The filtrate was extracted with ethyl acetate (100 ml×3), and washed with saturated aqueous solution of sodium chloride (50 ml). The extract was dried over anhydrous magnesium sulfate, and concentrated under reduced pressure. The residue was chromatographed over silica gel with ethyl acetate/hexane (1:1, v/v) as eluent to give the title compound 3.83 g, (yield=83%) as a pale yellow oily substance.

[α]$_D^{26}$=−52.9° (c 1.14, CHCl$_3$); $^1$H NMR (CDCl$_3$, 400 MHz) δ 2.11(brt, J=4.9 Hz, 1H, substituted with deuterium oxide), 2.66(brd, J=3.4 Hz, 1H, substituted with deuterium oxide), 3.64(ddd, J=3.9 Hz, 7.8 Hz, 11.7 Hz, 1H), 3.78(ddd, J=3.4 Hz, 6.8 Hz, 10.7 Hz, 1H), 4.75–4.88(m, 1H), 7.20–7.36(m, 3H), 7.39(s, 1H).

Preparation Example 24
(R)-(−) 1-(3-Chlorophenyl)-1,2-ethanediol-2-methanesulfonate

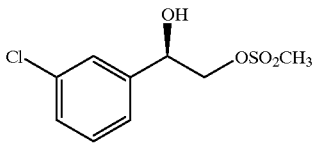

To a solution of (R)-(−)-1-(3'-chlorophenyl)-1,2-ethanediol (19.45 g) in tetrahydrofuran (200 ml) were added in turn triethylamine (18.9 ml) and methanesulfonyl chloride (11.3 ml) under ice-cooling, and the mixture was stirred for 2 hours. The reaction solution was diluted with ethyl acetate (200 ml), and washed in turn with a 10% aqueous solution of hydrochloric acid (100 ml), saturated aqueous solution of sodium hydrogencarbonate (100 ml) and saturated aqueous sodium chloride (100 ml). The organic layer was dried over anhydrous magnesium sulfate, and concentrated under reduced pressure. The residue was chromatographed over silica gel with ethyl acetate/benzene (1/7, v/v) as eluent to give the title compound (21.1 g, yield=75%) as a colorless oily substance.

[α]$_D^{26}$=−42.6° (c 2.21, CHCl$_3$); $^1$H NMR (CDCl$_3$, 400 MHz) δ 2.68(brd, J=2.9 Hz, 1H, substituted with deuterium oxide), 3.06(s, 3H), 4.25(dd, J=8.3 Hz, 11.2 Hz, 1H), 4.33 (dd, J=2.9 Hz, 10.7 Hz, 1H), 5.04(dt, J=3.4 Hz, 7.8 Hz, 1H), 7.20–7.40(m, 3H), 7.42(s, 1H).

Preparation Example 25
(R)-(−)-1-(3-Chlorophenyl)-1-methoxymethyloxy-2-ethanol methanesulfonate

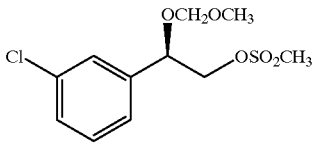

To a solution of (R)-(−)-1-(3-chlorophenyl)-1,2-ethanediol-2-methanesulfonate (21.1 g) in dichloromethane (200 ml) were added in turn chloromethyl methyl ether (10.9 ml) and 4-dimethylaminopyridine (5.15 g), and N,N-diisopropylethylamine (19.8 ml) was added dropwise over a period of 20 minutes under ice-cooling. The mixture was heated under reflux for 24 hours. The reaction solution was diluted with chloroform (100 ml), and washed in turn with saturated aqueous solution of sodium hydrogencarbonate (80 ml) and saturated aqueous sodium chloride (80 ml). The organic layer was dried over anhydrous sodium sulfate, and concentrated under reduced pressure. The residue was chromatographed over silica gel with ethyl acetate/benzene (1/7, v/v) as eluent to give the title compound (20.81 g, yield= 84%) as a colorless oily substance.

[α]$_D^{24}$=−127.1° (c 2.12, CHCl$_3$); $^1$H NMR (CDCl$_3$, 400 MHz) δ 3.00(s, 3H), 3.38(s, 3H), 4.27(dd, J=3.9 Hz, 11.2 Hz, 1H), 4.33(dd, J=7.8 Hz, 11.2 Hz, 1H), 4.60(d, J=6.8 Hz, 1H), 4.65 (d, J=6.8 Hz, 1H), 4.91(dd, J=3.9 Hz, 7.8 Hz, 1H), 7.20–7.40(m, 4H).

Preparation Example 26
(R)-(−)-N-[2-(3-Chlorophenyl)-2-methoxymethyloxyethyl]phthalimide

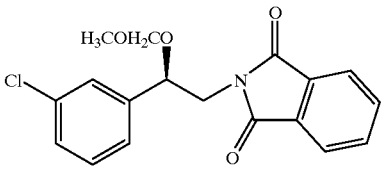

To a solution of (R)-(−)-1-(3-chlorophenyl)-1-methoxymethyloxy-2-ethanol methanesulfonate (20.81 g) in dimethylformamide (300 ml) was added potassium phthalimide (39.26 g), and the mixture was heated at 80° C. for 20 hours. The insoluble material was filtered out, and the solvent was distilled off under reduced pressure. The residue was diluted with diisopropyl ether (200 ml), and washed in turn with water (100 ml) and saturated aqueous sodium chloride (100 ml). The organic layer was dried over anhydrous magnesium sulfate, and concentrated under reduced pressure. The residue was chromatographed over silica gel with ethyl acetate/benzene (1/99, v/v) as eluent to give the title compound (19.87 g, yield=81%) as colorless crystals.

m.p. 81–84° C.; $[\alpha]_D^{25}$=–93.2° (c 2.12, CHCl$_3$); $^1$H NMR(CDCl$_3$) δ 3.09(s, 3H), 3.75(dd, J=4.4 Hz 14.2 Hz, 1H), 4.08(dd, J=9.3 Hz, 14.2 Hz, 1H), 4.49(d, J=13.7 Hz, 1H), 4.51(d, J=13.7 Hz, 1H), 5.01(dd, J=4.4 Hz, 9.3 Hz, 1H), 7.23–7.38(m, 3H), 7.46(s, 1H), 7.73(dd, J=2.9 Hz, 5.4 Hz, 2H), 7.87(dd, J=2.9 Hz, 5.4 Hz, 2H).

Preparation Example 27
(R)-(-)-N-[2-(3-Chlorophenyl)-2-hydroxyethyl]phthalimide

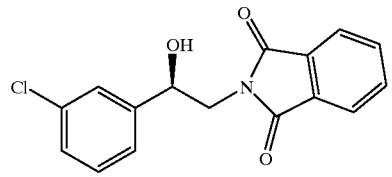

To a solution of (R)-(-)-N-[2-(3-chlorophenyl)-2-methoxymethyloxyethyl]phthalimide (18.0 g) in methanol (150 ml) were added a 10% aqueous solution of hydrochloric acid (22.8 ml) and water (30 ml), and the mixture was heated under reflux for 4 hours. The reaction solution was concentrated under reduced pressure. The residue was diluted with ethyl acetate (150 ml), and washed in turn with water (50 ml), saturated solution of sodium hydrogencarbonate (50 ml) and saturated aqueous sodium chloride (50 ml). The organic layer was dried over anhydrous magnesium sulfate, and concentrated under reduced pressure. The residue was recrystallized from ethyl acetate/hexane to give the title compound (9.27 g, yield=59%) as colorless crystals.

m.p. 143–145° C.; $[\alpha]_D^{25}$=–21.4° (c=2.40, CHCl$_3$) $^1$H NMR (CDCl$_3$, 400 MHz) δ 3.07(d, J=4.9 Hz, 1H, substituted with deuterium oxide), 3.94(dd, J=3.9 Hz, 14.2 Hz, 1H), 4.00(dd, J=7.8 Hz, 14.2 Hz, 1H), 5.05(quint, J=4.4 Hz, 1H), 7.24–7.36(m, 3H), 7.48(s, 1H), 7.74(dd, J=2.9 Hz, 5.4 Hz, 2H), 7.87(dd, J=2.9 Hz, 5.4 Hz, 2H).

Preparation Example 28
(R)-(-)-2-Amino-1-(3-chlorophenyl)ethanol

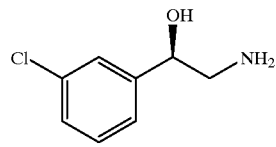

To a suspension of (R)-(-)-N-[2-(3-chlorophenyl)-2-hydroxyethyl]phthalimide (7.20 g) in ethanol (80 ml) was added hydrazine hydrate (2.2 ml), and the mixture was heated under reflux for 0.5 hours. After water (50 ml) was added to the reaction solution and the insoluble material was dissolved, the solvent was distilled off under reduced pressure. The residue was diluted with a 10% aqueous solution of sodium hydroxide (100 ml), and extracted with chloroform (100 ml×3). The solvent was distilled off under reduced pressure to give the title compound (4.01 g, yield=98%) as a colorless oily substance. A part of the compound was subjected to a silica gel column chromatography to give the title compound from the fraction of methanol/ethyl acetate/aqueous ammonia (15/85/2, v/v/v). As a result of measuring the spectral data of this compound, the data were identical with those of Preparation Example 8.

$[\alpha]_D^{26}$=–59.5° (c 1.13, CHCl$_3$).

Preparation Example 29
(S)-2-Chloro-1-(3-chlorophenyl)-1-methoxymethyloxyethane

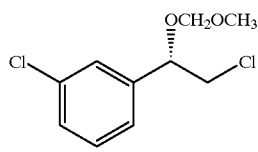

To a solution of (S)-2-chloro-1-(3-chlorophenyl)ethanol (5.9 g) which was prepared by the method as described in J. Med. Chem. Vol. 35, 3081, (1991) in dichloromethane (150 ml) were added 4-dimethylaminopyridine (0.37 g) and chloromethyl methyl ether (4.70 ml). N,N-Diisopropylethylamine (10.7 ml) was added dropwise under ice-cooling, and the mixture was stirred at room temperature for 40 hours. The reaction solution was diluted with chloroform (100 ml), and washed in turn with saturated aqueous solution of sodium hydrogencarbonate (50 ml) and saturated aqueous sodium chloride (50 ml). The organic layer was dried over anhydrous sodium sulfate, and the solvent was distilled off under reduced pressure. The residue was chromatographed over silica gel with ethyl acetate/hexane (1/9, v/v) as eluent to give the title compound (5.81 g, yield=80%) as a colorless oily substance.

$^1$H NMR (CDCl$_3$, 400 MHz) δ 3.40(s, 3H), 3.62(dd, J=4.3 Hz, 11.2 Hz, 1H), 3.70(dd, J=7.8 Hz, 11.2 Hz, 1H), 4.59(d, J=6.8 Hz, 1H), 4.65(d, J=6.8 Hz, 1H), 4.79(dd, J=4.3 Hz, 7.8 Hz, 1H), 7.23–7.35(m, 4H).

Preparation Example 30
(S)-2-(3-Chlorophenyl)-2-methoxymethyloxyethylazide

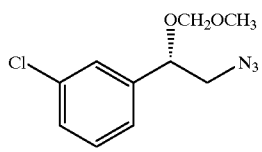

To a solution of (S)-2-chloro-1-(3-chlorophenyl)-1-methoxymethyloxyethane (5.81 g) in dimethylformamide (150 ml) was added sodium azide (16 g), and the mixture was heated with stirring at 120° C. for 17 hours. The reaction solution was diluted with ethyl acetate (100 ml), and washed in turn with water (100 ml) and saturated aqueous sodium chloride (100 ml). The organic layer was dried over anhydrous sodium sulfate, and the solvent was distilled off under reduced pressure to give the title compound (5.61 g, yield=85%) as a colorless oily substance.

$^1$H NMR (CDCl$_3$, 400 MHz) δ 3.27(dd, J=3.9 Hz, 13.1 Hz, 1H), 3.41(s, 3H), 3.51(dd, J=8.7 Hz, 13.1 Hz, 1H), 4.58(d, J=6.8 Hz, 1H), 4.64(d, J=6.8 Hz, 1H), 4.77(dd, J=3.9 Hz, 8.7 Hz, 1H), 7.20–7.35(m, 4H).

Preparation Example 31

(S)-2-(3-Chlorophenyl)-2-methoxymethyloxyethylamine

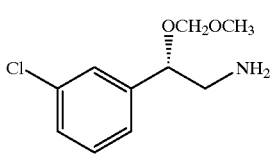

To a solution of (S)-2-(3-chlorophenyl)-2-methoxymethyloxyethyl azide (5.6 g) in methanol (60 ml) was added platinum oxide (0.4 g), and the mixture was stirred under hydrogen atmosphere at room temperature for 4 hours. The catalysis was filtered out, and the solvent was distilled off under reduced pressure. The residue was chromatographed over silica gel with 5% methanol/chloroform (v/v) as eluent to give the title compound (4.21 g, yield= 83%) as a colorless oily substance.

$^1$H NMR (CDCl$_3$, 400 MHz) δ 1.46(brs, 2H), 2.89(dd, J=4.4 Hz, 13.6 Hz, 1H), 2.95(dd, J=6.8 Hz, 13.6 Hz, 1H), 3.38(s, 3H), 4.56(dd, J=4.4 Hz, 6.8 Hz, 1H), 4.58(d, J=6.3 Hz, 1H), 4.61(d, J=6.3 Hz, 1H), 7.18–7.21(m, 1H), 7.25–7.28(m, 2H), 7.30–7.32(m, 1H).

Preparation Example 32

(S)-(+)-2-Amino-1-(3-chlorophenyl)ethanol

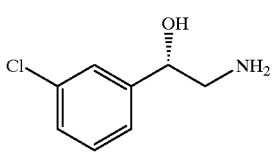

To a solution of (S)-2-(3-chlorophenyl)-2-methoxymethyloxyethylamine (4.2 g) in methanol (50 ml) were added concentrated hydrochloric acid (6 ml) and water (10 ml), and the mixture was heated under reflux for 2 hours. The insoluble material was filtered out, and the solvent was distilled off under reduced pressure to give the hydrochloride (3.37 g, yield=83%) of the title compound as pale yellow crystals.

After the crystals which were obtained were recrystallized from isopropanol/diisopropyl ether, the crystals were dissolved in water (50 ml). 1N aqueous solution of sodium hydroxide (100 ml) was added to the solution, and extracted with ethyl acetate (100 ml×5). The extract was washed with saturated aqueous sodium chloride (50 ml), dried over anhydrous sodium sulfate, and concentrated under reduced pressure to give the title compound (1.10 g) as a pale yellow oily substance.

$[α]_D^{24}$=+56.0° (c=0.71, CHCl$_3$).

The spectral data were identical with those of Preparation Example 8.

Preparation Example 33

(S)-(+)-N-Benzylmandelamide

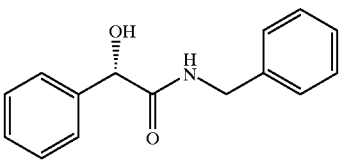

After (S)-(−)-mandelic acid (15 g) and 1-hydroxybenzotriazole (21.1 g) were added to a solution of benzylamine (15.8 g) in dimethylformamide (200 ml), a solution of dicyclohexylcarbodiimide (30.5 g) in dimethylformamide (50 ml) was added dropwise over a period of 10 minutes and the mixture was heated with stirring at 100° C. for 2 hours. The reaction solution was ice-cooled, water (300 ml) was added, and the precipitated insoluble material was filtered out. The filtrate was extracted with ethyl acetate (300 ml), and the organic layer was washed in turn with a 10% aqueous solution of hydrochloric acid (150 ml) and saturated aqueous sodium chloride (150 ml). The organic layer was dried over anhydrous magnesium sulfate, and the solvent was distilled off under reduced pressure. The residue was recrystallized from ethyl acetate (50 ml) to give the title compound (9.09 g, yield=38%) as colorless crystals.

$[α]_D^{30}$=+44.7° (c 1.51, CH$_3$OH); $^1$H NMR (CDCl$_3$, 400 MHz) δ 4.38–4.57(m, 2H), 5.12(s, 1H), 6.42–6.60(brs, 1H), 7.19–7.42(m, 10H).

Preparation Example 34

(R)-(−)-N-Benzylmandelamide

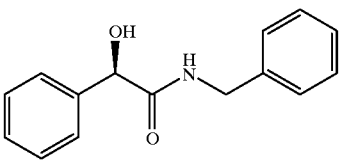

The title compound (9.3 g, yield=39%) was obtained as colorless crystals by using (R)-mandelic acid according to the same process as described in Preparation Example 33.

The spectral data were identical with those of Preparation Example 33.

Preparation Example 35

(S)-(+)-2-Benzylamino-1-phenylethanol

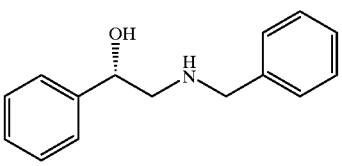

To a suspension of lithium aluminum hydride (5.92 g) in tetrahydrofuran was added dropwise a solution of (S)-(+)-N-benzylmandelamide (8.0 g) in tetrahydrofuran (80 ml) over a period of 10 minutes under ice-cooling, and the mixture was heated under reflux for 3 hours. The excess reagent was inactivated by aqueous ammonia, and the precipitated insoluble material was filtered out. The filtrate was extracted with ethyl acetate (200 ml), and washed with saturated aqueous solution of sodium chloride (50 ml). The extract was dried over anhydrous sodium sulfate, and the solvent was distilled off under reduced pressure. The residue was chromatographed over silica gel with methanol/ethyl acetate/aqueous ammonia. (10/90/0.1, v/v) as eluent to give the title compound (3.28 g, yield=44%) as colorless crystals. $[\alpha]_D^{26}$=+35.4° (c 1.00, CH$_3$OH); $^1$H NMR (CDCl$_3$, 400 MHz) δ 1.33–2.22(br, 2H, substituted with deuterium oxide), 2.76(dd, J=8.8 Hz, 12.2 Hz, 1H), 2.95(dd, J=3.4 Hz, 12.2 Hz, 1H), 3.82(d, J=13.2 Hz, 1H), 3.87(d, J=13.2Hz, 1H), 4.73(dd, J=3.9 Hz, 8.8 Hz, 1H), 7.22–7.38(m, 5H).

Preparation Example 36
(R)-(−)-2-Benzylamino-1-phenylethanol

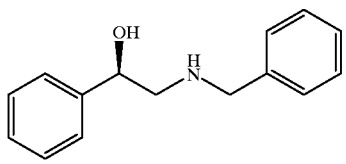

The title compound was obtained as colorless crystals by using (R)-(−)-N-benzylmandelamide according to the same process as described in Preparation Example 35. Yield=30%.

$[\alpha]_D^{23}$=−34.2° (c 1.03, CH$_3$OH).

The spectral data were identical with those of Preparation Example 35.

Preparation Example 37
(S)-(+)-2-Amino-1-phenylethanol

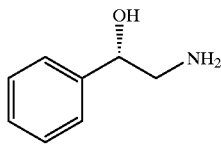

To a solution of (S)-(+)-2-benzylamino-1-phenylethanol (3.0 g) in methanol (30 ml) were added ammonium formate (4.17 g) and 10% palladium carbon (0.60 g), and the mixture was heated under reflux for one hour. The insoluble material was filtered out, and the solvent was distilled off under reduced pressure to give the title compound (1.97 g) as pale yellow crystals.

$^1$H NMR (CDCl$_3$, 400 MHz) δ 2.01 (brs, 3H, substituted with deuterium oxide), 2.81(dd, J=7.8 Hz, 12.7 Hz, 1H), 3.00(dd, J=3.9 Hz, 12.7 Hz, 1H), 4.64(dd, J=3.9 Hz, 7.8 Hz, 1H), 7.20–7.41(m, 5H).

Preparation Example 38
(R)-(−)-2-Amino-1-phenylethanol

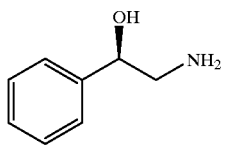

The title compound was obtained as pale yellow crystals by using (R)-(−)-2-benzylamino-1-phenylethanol according to the same process as described in Preparation Example 37.

Preparation Example 39
(R)-(−)-2-Benzylamino-1-(3-chlorophenyl)ethanol

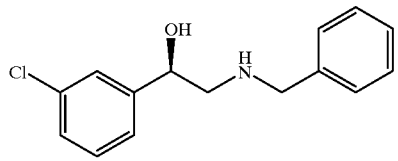

To a solution of benzylamine (2.90 ml) in dimethylformamide (60 ml) was added trimethylsilylacetamide (3.81 g), and the mixture was stirred at room temperature for one hour. To the reaction solution was added dropwise a solution of (R)-3-chlorostyrene oxide which was prepared by the method as described in J. Med. Chem. Vol. 35, 3081, (1991) (otherwise available from Nitto Chemical Industry) in dimethylformamide (20 ml), and the mixture was heated at 90° C. for 26 hours. To the reaction solution was added ethyl acetate (100 ml), and washed in turn with water (20 ml), 1N aqueous solution of hydrochloric acid (20 ml) and saturated aqueous sodium chloride (20 ml). The organic layer was dried over anhydrous sodium sulfate, and the solvent was distilled off under reduced pressure. The residue was chromatographed over silica gel with 5% methanol/chloroform (v/v) as eluent to give the title compound 3.1g, yield=66%) as colorless crystals.

$^1$H NMR (CDCl$_3$, 400 MHz) δ 1.20–2.40(br, 2H, substituted with deuterium oxide), 2.70(dd, J=8.8 Hz, 12.2 Hz, 1H), 2.93(dd, J=3.9 Hz, 12.2 Hz, 1H), 3.81(d, J=13.2 Hz, 1H), 3.86(d, J=13.2 Hz, 1H), 4.68(dd, J=3.4 Hz, 8.8 Hz, 1H), 7.18–7.41(m, 9H).

Preparation Example 40
(S)-(+)-2-Benzylamino-1-(3-chlorophenyl)ethanol

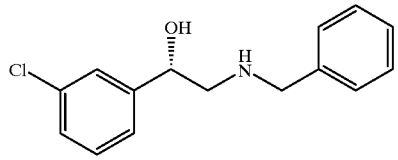

The title compound was obtained as colorless crystals by using (S)-3-chlorostyrene oxide according to the same process as described in Preparation Example 39. Yield=49%.

m.p. 71.5–72.5° C. (recrystallized from diisopropyl ether/hexane); $[\alpha]_D^{27}$=+49.2° (c 1.12, CHCl$_3$).

The spectral data were identical with those of Preparation Example 39.

Preparation Example 41
(R)-(−)-2-Amino-1-phenylethanol

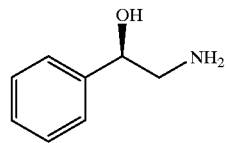

The title compound was obtained as colorless crystals by using (R)-(−)-2-benzylamino-1-(3-chlorophenyl)ethanol according to the same process as described in Preparation Example 37. Yield=92%.

$[\alpha]_D^{25}$=−21.3° (c 1.07, CHCl$_3$).

The spectral data were identical with those of Preparation Example 37.

Preparation Example 42
(S)-(+)-2-Amino-1-phenylethanol

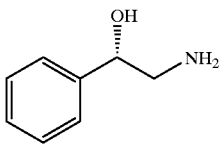

The title compound was obtained as colorless crystals by using (S)-(+)-2-benzylamino-1-(3-chlorophenyl)ethanol according to the same process as described in Preparation Example 37. Yield=92%.

The spectral data were identical with those of Preparation Example 37.

Preparation Example 43
(2'R,5"R)-6-{2-[5-(3-chlorophenyl)-2-oxo-3-oxazolidinyl]}propyl-2,3-dihydro-1,4-benzodioxin-2-carboxylic acid methyl ester

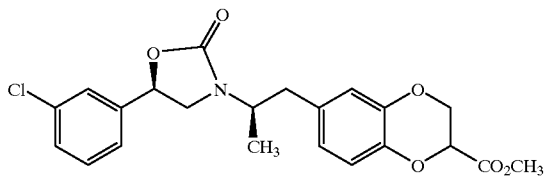

and
(2'S,5"R)-6-{2-[5-(3-Chlorophenyl)-2-oxo-3-oxazolidinyl]}propyl-2,3-dihydro-1,4-benzodioxin-2-carboxylic acid methyl ester

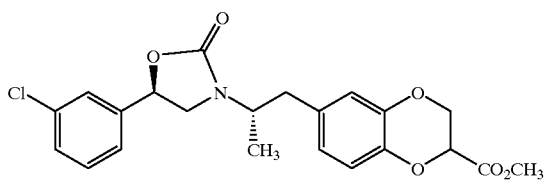

To a solution of (2"R)-6-{2-[2-(3-chlorophenyl)-2-hydroxyethyl]amino}propyl-2,3-dihydro-1,4-benzodioxin-2-carboxylic acid methyl ester (3.51 g) prepared in Example 16 and triethylamine (8.45 ml) in tetrahydrofuran (50 ml) was added N,N'-carbonyldiimidazole (4.91 g) under ice-cooling, and the mixture was stirred at room temperature for 0.5 hours. The reaction solution was diluted with ethyl acetate (100 ml), and washed in turn with a 10% aqueous solution of hydrochloric acid (50 ml), saturated aqueous solution of sodium hydrogencarbonate (50 ml) and saturated aqueous sodium chloride (50 ml). The organic layer was dried over anhydrous magnesium sulfate, and the solvent was distilled off under reduced pressure. The residue was chromatographed over silica gel with ethyl acetate/benzene (1/10, v/v) as eluent to give the high polar (2'R,5"R)-6-{2-[5-(3-chlorophenyl)-2-oxo-3-oxazolidinyl]}propyl-2,3-dihydro-1,4-benzodioxin-2-carboxylic acid methyl ester (1.55 g, yield=42%) and the low polar (2'S,5"R)-6-{2-[5-(3-chlorophenyl)-2-oxo-3-oxazolidinyl]}propyl-2,3-dihydro-1,4-benzodioxin-2-carboxylic acid methyl ester (1.24 g, yield=33%) as a pale yellow oily substance.

(2'R,5"R)-6-{2-[5-(3-Chlorophenyl)-2-oxo-3-oxazolidinyl]}propyl-2,3-dihydro-1,4-benzodioxin-2-carboxylic acid methyl ester $[\alpha]_D^{26}$=−46.0° (c 2.98, CHCl$_3$); $^1$H NMR (CDCl$_3$, 400 MHz) δ 1.240, 1.242(pair of d, J=6.8 Hz, 6.4 Hz, 3H), 2.62–2.76(m, 2H), 3.27(dd, J=6.8 Hz, 8.8 Hz, 1H), 3.78–3.87(m, 1H), 3.81(s, 3H), 4.24(quint, J=8.3 Hz, 1H), 4.30–4.41(m, 2H), 4.82(t, J=3.4 Hz, 1H), 5.37(dd, J=6.8 Hz, 9.3 Hz, 1H), 6.62–6.73(m, 2H), 6.91(d, J=8.8 Hz, 0.5H), 6.93(d, J=8.3 Hz, 0.5H), 7.15–7.30(m, 3H), 7.35(brs, 1H).

(2'S,5"R)-6-{2-[5-(3-Chlorophenyl)-2-oxo-3-oxazolidinyl]}propyl-2,3-dihydro-1,4-benzodioxin-2-carboxylic acid methyl ester $[\alpha]_D^{25}$ =+43.3° (c 1.05, CHCl$_3$); $^1$H NMR (CDCl$_3$, 400 MHz) δ 1.19(d, J=6.8 Hz, 3H), 2.71(ddd, J=3.9 Hz, 6.8 Hz, 13.7 Hz, 1H), 2.80(ddd, J=2.4 Hz, 7.8 Hz, 13.7 Hz, 1H), 3.26(dd, J=8.8 Hz, 17.1 Hz, 1H), 3.74(dt, J=8.8 Hz, 17.1 Hz, 1H), 3.81, 3.82(pair of s, 3H), 4.17(sixtet, J=7.3 Hz, 1H), 4.32–4.41(m, 2H), 4.83(t, J=3.9 Hz, 1H), 5.33(t, J=8.3 Hz, 1H), 6.71–6.80(m, 2H), 6.94(dd, J=2.0 Hz, 7.8 Hz, 1H), 7.14–7.22(m, 1H), 7.25–7.40(m, 3H).

Preparation Example 44
(2'S,5"S)-6-{2-[5-(3-Chlorophenyl)-2-oxo-3-oxazolidinyl]}propyl-2,3-dihydro-1,4-benzodioxin-2-carboxylic acid methyl ester

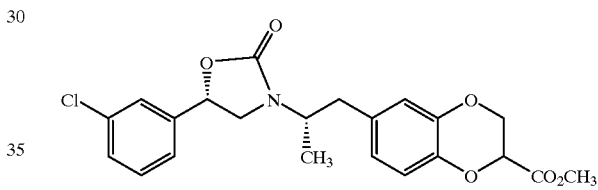

and
(2'R,5"S)-6-{2-[5-(3-chlorophenyl)-2-oxo-3-oxazolidinyl]}propyl-2,3-dihydro-1,4-benzodioxin-2-carboxylic acid methyl ester

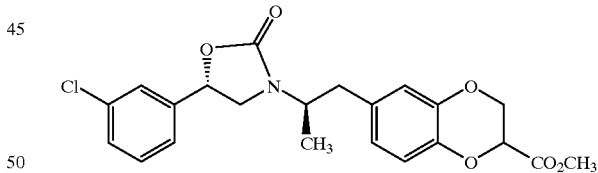

A colorless oily (2'S,5"S)-6-{2-[5-(3-chlorophenyl)-2-oxo-3-oxazolidinyl]}propyl-2,3-dihydro-1,4-benzodioxin-2-carboxylic acid methyl ester (yield=41%) and a colorless oily (2'R,5"S)-6-{2-[5-(3-chlorophenyl)-2-oxo-3-oxazolidinyl]}propyl-2,3-dihydro-1,4-benzodioxin-2-carboxylic acid methyl ester (yield=32%) were obtained by using (2"S)-6-{2-[2-(3-chlorophenyl)-2-hydroxyethyl]amino}propyl-2,3-dihydro- 1,4-benzodioxin-2-carboxylic acid methyl ester obtained in Example 17 according to the same process as described in Preparation Example 43.

(2'S,5"S)-6-{2-[5-(3-Chlorophenyl)-2-oxo-3-oxazolidinyl]}propyl-2,3-dihydro-1,4-benzodioxin-2-carboxylic acid methyl ester $[\alpha]_D^{25}$=+46.1° (c 1.06, CHCl$_3$).

The spectral data were identical with those of (2'R,5"R)-6-{2-[5-(3-chlorophenyl)-2-oxo-3-oxazolidinyl]}propyl-2,3-dihydro-1,4-benzodioxin-2-carboxylic acid methyl ester.

(2'R,5"S)-6-{2-[5-(3-Chlorophenyl)-2-oxo-3-oxazolidinyl]}propyl-2,3-dihydro-1,4-benzodioxin-2-carboxylic acid methyl ester $[\alpha]_D^{24}=-41.2$ (c 1.12, $CHCl_3$).

The spectral data were identical with those of (2'S,5"R)-6-{2-[5-(3-chlorophenyl)-2-oxo-3-oxazolidinyl]}propyl-2,3-dihydro-1,4-benzodioxin-2-carboxylic acid methyl ester.

Preparation Example 45

(2'R,5"R)-6-[2-(2-Oxo-5-phenyl-3-oxazolidinyl)]propyl-2,3-dihydro-1,4-benzodioxin-2-carboxylic acid methyl ester

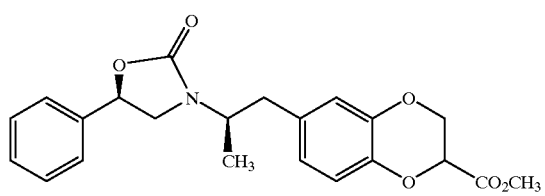

and
(2'S,5"R)-6-[2-(2-oxo-5-phenyl-3-oxazolidinyl)]propyl-2,3-dihydro-1,4-benzodioxin-2-carboxylic acid methyl ester

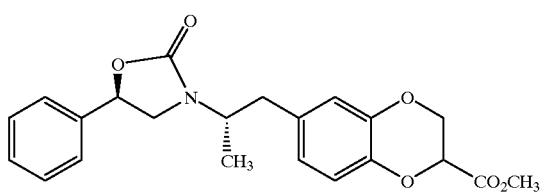

A colorless oily (2'R,5"R)-6-[2-(2-oxo-5-phenyl-3-oxazolidinyl)]propyl-2,3-dihydro-1,4-benzodioxin-2-carboxylic acid methyl ester (yield=48%) and a colorless oily (2'S,5"R)-6-[2-(2-oxo-5-phenyl-3-oxazolidinyl)]propyl-2,3-dihydro-1,4-benzodioxin-2-carboxylic acid methyl ester (yield=39%) were obtained by using (2"R)-6-[2-(2-hydroxy-2-phenylethyl)amino]propyl-2,3-dihydro-1,4-benzodioxin-2-carboxylic acid methyl ester obtained in Example 18 according to the same process as described in Preparation Example 43.

(2'R,5"R)-6-[2-(2-Oxo-5-phenyl-3-oxazolidinyl)]propyl-2,3-dihydro-1,4-benzodioxin-2-carboxylic acid methyl ester $^1$H NMR ($CDCl_3$, 400 MHz) δ 1.23(d, J=6.4 Hz, 3H), 2.69(d, J=7.8 Hz, 2H), 3.31(t, J=7.3 Hz, 1H), 3.75–3.87(m, 1H), 3.81(s, 3H), 4.25(quint, J=6.8 Hz, 1H), 4.30–4.40(m, 2H), 4.83(t, J=3.9 Hz, 1H), 5.39(dd, J=6.8, 9.3 Hz, 1H), 6.60(m, 2H), 6.89 (t, J=7.8 Hz, 1H), 7.10–7.20(m, 2H), 7.29–7.40(m, 3H).

(2'S,5"R)-6-[2-(2-Oxo-5-phenyl-3-oxazolidinyl)]propyl-2,3-dihydro-1,4-benzodioxin-2-carboxylic acid methyl ester $^1$H NMR ($CDCl_3$, 400 MHz) δ 1.19(d, J=6.3 Hz, 3H), 2.70(ddd, J=2.4 Hz, 6.8 Hz, 13.7 Hz, 1H), 2.81(ddd, J=2.4 Hz, 7.8 Hz, 14.2 Hz, 1H), 3.31(dd, J=8.3 Hz, 15.6 Hz, 1H), 3.74(dd, J=8.8 Hz, 17.6 Hz, 1H), 3.80(s, 1.5H), 3.81(s, 1.5H), 4.12–4.25(m, 1H), 4.37(d, J=3.9 Hz, 2H), 4.83(t, J=3.9 Hz, 1H), 5.36(t, J=8.3 Hz, 1H), 6.70–6.80(m, 2H), 6.94(d, J=8.8 Hz, 1H), 7.22–7.45(m, 5H).

Preparation Example 46

(2'S,5"S)-6-[2-(2-Oxo-5-phenyl-3-oxazolidinyl)]propyl-2,3-dihydro-1,4-benzodioxin-2-carboxylic acid methyl ester

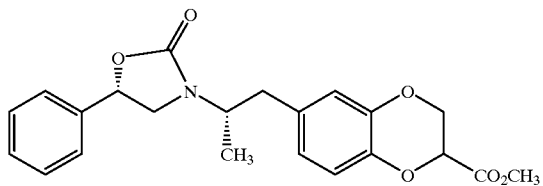

and
(2'R,5"S)-6-[2-(2-oxo-5-phenyl-3-oxazolidinyl)]propyl-2,3-dihydro-1,4-benzodioxin-2-carboxylic acid methyl ester

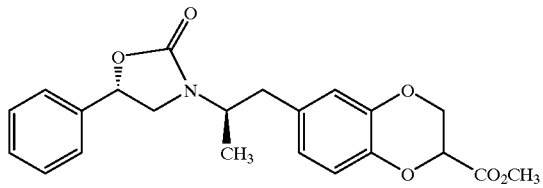

A pale yellow oily (2'S,5"S)-6-[2-(2-oxo-5-phenyl-3-oxazolidinyl)]propyl-2,3-dihydro-1,4-benzodioxin-2-carboxylic acid methyl ester (yield=43%) and a pale yellow oily (2'R,5"S)-6-[2-(2-oxo-5-phenyl-3-oxazolidinyl)] propyl- 2,3-dihydro-1,4-benzodioxin-2-carboxylic acid methyl ester (yield=37%) were obtained by using (2"S)-6-[2-(2-hydroxy-2-phenylethyl)amino]propyl-2,3-dihydro-1,4-benzodioxin-2-carboxylic acid methyl ester obtained in Example 19 according to the same process as described in Preparation Example 43.

(2'S,5"S)-6-[2-(2-Oxo-5-phenyl-3-oxazolidinyl)]propyl-2,3-dihydro-1,4-benzodioxin-2-carboxylic acid methyl ester The spectral data were identical with those of (2'R,5"R)-6-[2-(2-oxo-5-phenyl-3-oxazolidinyl)]propyl-2,3-dihydro-1,4-benzodioxin-2-carboxylic acid methyl ester.

(2'R,5"S)-6-[2-(2-Oxo-5-phenyl-3-oxazolidinyl)]propyl-2,3-dihydro-1,4-benzodioxin-2-carboxylic acid methyl ester The spectral data were identical with those of (2'S,5"R)-6-[2-(2-oxo-5-phenyl-3-oxazolidinyl)]propyl-2,3-dihydro-1,4-benzodioxin-2-carboxylic acid methyl ester.

Preparation Example 47

6-Formyl-N-(R)-phenylethyl-2,3-dihydro-1,4-benzodioxin-2-(R)-carboxamide

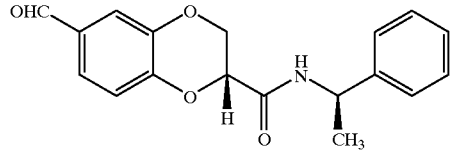

and
6-formyl-N-(R)-phenylethyl-2,3-dihydro-1,4-benzodioxin-2-(S)-carboxamide

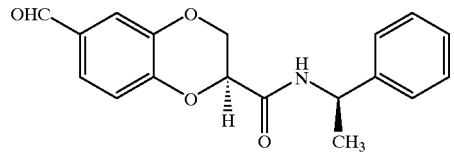

To a solution of 6-formyl-2,3-dihydro-1,4-benzodioxin-2-carboxylic acid (20.0 g) obtained in Preparation Example 14 in dimethylformamide (300 ml) were added (R)-(+)-phenylethylamine (11.65 g) and 1-hydroxybenzotriazole (15.59 g), followed by 1-ethyl-3-(3-dimethylaminopropyl) carbodiimide hydrochloride (WSCI HCl, 20.28 g), and the mixture was stirred at room temperature for 15 hours. To the reaction solution was added water (100 ml), and dimethylformamide was distilled off under reduced pressure. The residue was extracted with ethyl acetate (150 ml×3), and the combined organic layer was washed in turn with a 10% (w/v) aqueous solution of hydrochloric acid (100 ml), saturated aqeos solution of sodium hydrogencarbonate (100 ml), water (100 ml) and saturated aqueous sodium chloride (100 ml). The organic layer was dried over magnesium sulfate, and the solvent was distilled off under reduced pressure. The precipitated crystals were recrystallized from ethyl acetate to give 6-formyl-N-(R)-phenylethyl-2,3-dihydro-1,4-benzodioxin-2-(S)-carboxamide (11.65 g, yield=39%) as pale yellow crystals. Further, the mother liquor was chromatographed over silica gel (Li Chroprep Si-60, 400 g, available from Merck) to give 6-formyl-N-(R)-phenylethyl-2,3-dihydro- 1,4-benzodioxin-2-(R)-carboxamide (12.74 g, yield=43%) as a pale yellow oily substance from the fraction of ethyl acetate/hexane (1/3, v/v). A part of the oily substance was recrystallized from isopropanol-normal hexane to give the colorless prisms, and the analytical data were measured. 6-Formyl-N-(R)-phenylethyl-2,3-dihydro-1,4-benzodioxin-2-(R)-carboxamide m.p. 98–100° C.; $[\alpha]_D^{29}=-35.3°$ (c 1.36, CHCl$_3$); $^1$H NMR (CDCl$_3$, 400 MHz) δ 1.49(d, J=6.8 Hz, 3H), 4.24(dd, J=7.8 Hz, 11.7 Hz, 1H), 4.62(dd, J=2.9 Hz, 11.7 Hz, 1H), 4.72(dd, J=2.9 Hz, 7.8 Hz, 1H), 5.18(quint, J=7.0 Hz, 1H), 6.67–6.70 (brm, 1H), 7.08(d, J=8.8 Hz, 1H), 7.28–7.52(m, 7H), 9.85(s, 1H); $^{13}$C NMR (CDCl$_3$) 0 21.9, 49.1, 65.7, 73.9, 118.1, 119.3, 124.3, 126.5, 128.1, 129.2, 132.0, 142.6, 144.1, 147.2, 165.6, 190.6.
6-Formyl-N-(R)-phenylethyl-2,3-dihydro-1,4-benzodioxin-2-(S)-carboxamide m.p. $_{144-145}$° C.; $[\alpha]_D^{29}=-13.6°$ (c 1.10, CHCl$_3$); $^1$H NMR (CDCl$_3$, 400 MHz) δ 1.56(d, J=6.8 Hz, 3H), 4.20(dd, J=7.3 Hz, 11.2 Hz, 1H), 4.58(dd, J=2.9 Hz, 11.7 Hz, 1H), 4.78(dd, J=2.4 Hz, 7.3 Hz, 1H), 5.19(quint, J=6.8 Hz, 1H), 6.65–6.68(brm, 1H), 7.09(d, J=8.3 Hz, 1H), 7.15–7.33(m, 5H), 7.40–7.48(m, 2H), 9.85(s, 1H); $^{13}$C NMR (CDCl$_3$) δ 22.0, 49.0, 65.7, 73.9, 118.1, 119.3, 124.3, 126.1, 127.9, 129.1, 132.0, 142.7, 144.1, 147.2, 165.7, 190.6.

Preparation Example 48
(R)-6-Formyl-2,3-dihydro-1,4-benzodioxin-2-carboxylic acid

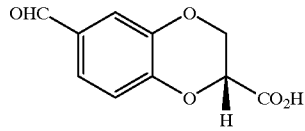

To a solution of 6-formyl-N-(R)-phenylethyl-2,3-dihydro-1,4-benzodioxin-2-(R)-carboxamide (12.7 g) in acetic acid/water (1/1, v/v, 80 ml) was added concentrated sulfuric acid (4.5 ml), and the mixture was heated under reflux for 25.5 hours. The reaction solution was ice-cooled, and the precipitated crystals were filtered out. The crystals were washed with water (50 ml) and cold ethanol (50 ml), and dried to give the title compound (5.87 g, yield=69%) as pale brown crystals. A part of the crystals was recrystallized from ethanol to give pale yellow crystals, and the analytical data were measured.

m.p. 238–239° C.; $[\alpha]_D^{26}=+38.2°$ (c 1.03, CH$_3$OH).

The spectral data were identical with those of Preparation Example 14.

Preparation Example 49
(S)-6-Formyl-2,3-dihydro-1,4-benzodioxin-2-carboxylic acid

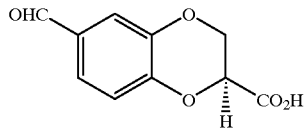

The title compound was obtained as pale yellow crystals by using 6-formyl-N-(R)-phenylethyl-2,3-dihydro-1,4-benzodioxin-2-(S)-carboxamide according to the same process as described in Preparation Example 48. Yield=91%.

m.p. 233–235° C.; $[\alpha]_D^{26}=-37.6°$ (c 1.04, CH$_3$OH).

The spectral data were identical with those of Preparation Example 14.

Preparation Example 50
(R)-6-Formyl-2,3-dihydro-1,4-benzodioxin-2-carboxylic acid methyl ester

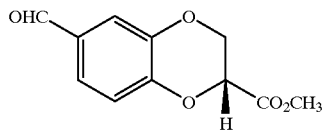

To a solution of (R)-6-formyl-2,3-dihydro-1,4-benzodioxin-2-carboxylic acid (6.20 g) in methanol/benzene (1/1, v/v, 200 ml) was added concentrated sulfuric acid (1.5 ml), and the mixture was heated under reflux for 2.5 hours. The solvent was distilled off under reduced pressure, and to the residue was added water (50 ml). The solution was extracted with ethyl acetate (100 ml×3), and the combined organic layer was washed in turn with saturated aqueous solution of sodium hydrogencarbonate (50 ml) and saturated aqueous sodium chloride (50 ml),dried over magnesium sulfate. The solvent was distilled off under reduced pressure. The residue was recrystallized from ethyl acetate/hexane (1/2, v/v, 45 ml) to give the title compound (3.73 g, yield=56%) as pale brown crystals.

m.p. 90–90.5° C.; $[\alpha]_D^{28}=+14.8°$ (c 1.01, CHCl$_3$).

The spectral data were identical with those of Preparation Example 15.

Preparation Example 51
(S)-6-Formyl-2,3-dihydro-1,4-benzodioxin-2-carboxylic acid methyl ester

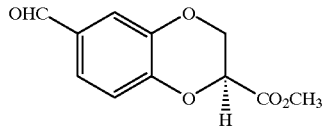

The title compound was obtained as colorless needles by using (S)-6-formyl-2,3-dihydro-1,4-benzodioxin-2- carboxylic acid according to the same process as described in Preparation Example 50. Yield=53%.

m.p. 87–88° C.; $[\alpha]_D^{29}=-14.6°$ (c 1.02, $CHCl_3$).

The spectral data were identical with those of Preparation Example 15.

Preparation Example 52
(R)-6-Formyl-2,3-dihydro-1,4-benzodioxin-2-carboxylic acid ethyl ester

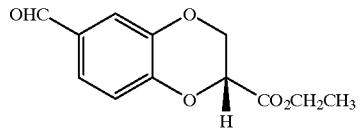

The title compound was obtained as a pale yellow oily substance according to the same process as described in Preparation Example 50, except for using ethanol instead of methanol. Yield=99%.

$[\alpha]_D^{28}=+15.6°$ (c 1.15, $CHCl_3$); $^1H$ NMR ($CDCl_3$, 400 MHz) δ 1.29(t, J=6.8 Hz, 3H), 4.28(dq, J=2.9 Hz, 7.3 Hz, 2H), 4.39(dd, J=2.9 Hz, 7.3 Hz, 1H), 4.48(dd, J=4.4 Hz, 11.7 Hz, 1H), 4.91(dd, J=2.9 Hz, 3.9 Hz, 1H), 7.13(d, J=8.3 Hz, 1H), 7.41(d, J=2.0 Hz, 1H), 7.47(dd, J=2.0 Hz, 8.3 Hz, 1H), 9.84(s, 1H).

Preparation Example 53
(S)-6-Formyl-2,3-dihydro-1,4-benzodioxin-2-carboxylic acid ethyl ester

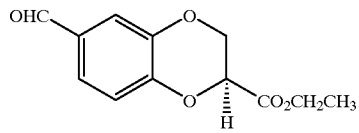

The title compound was obtained as a pale yellow oily substance by using (S)-6-formyl-2,3-dihydro-1,4-benzodioxin-2-carboxylic acid and ethanol according to the same process as described in Preparation Example 50. Yield=84%.

$[\alpha]_D^{29}=-16.5°$ (c 1.02, $CHCl_3$).

The spectral data were identical with those of Preparation Example 52.

Preparation Example 54
(R)-6-Acetonyl-2,3-dihydro-1,4-benzodioxin-2-carboxylic acid methyl ester

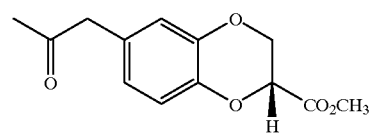

The title compound was obtained as a colorless oily substance by using (R)-6-formyl-2,3-dihydro-1,4-benzodioxin-2-carboxylic acid methyl ester according to the same process as described in Preparation Example 16. Yield=70%, 2 steps.

$[\alpha]_D^{29}=+28.3°$ (c 1.02, $CHCl_3$).

The spectral data were identical with those of Preparation Example 16.

Preparation Example 55
(S)-6-Acetonyl-2,3-dihydro-1,4-benzodioxin-2-carboxylic acid methyl ester

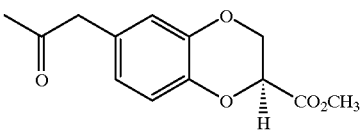

The title compound was obtained as a colorless oily substance by using (S)-6-formyl-2,3-dihydro-1,4-benzodioxin-2-carboxylic acid methyl ester according to the same process as described in Preparation Example 16. Yield=27%, 2 steps.

$[\alpha]_D^{27}=-28.5°$ (c 1.10, $CHCl_3$).

The spectral data were identical with those of Preparation Example 16.

Preparation Example 56
(R)-6-Acetonyl-2,3-dihydro-1,4-benzodioxin-2-carboxylic acid ethyl ester

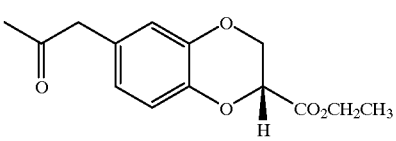

The title compound was obtained as colorless needles (recrystallized from ethyl acetate/hexane) by using (R)-6-formyl-2,3-dihydro-1,4-benzodioxin-2-carboxylic acid ethyl ester and ethanol according to the same process as described in Preparation Example 16. Yield=59%, 2 steps.

m.p. 61–62° C.; $[\alpha]_D^{29}=+27.5°$ (c 1.00, $CHCl_3$).

The spectral data were identical with those of Preparation Example 17.

Preparation Example 57
(S)-6-Acetonyl-2,3-dihydro-1,4-benzodioxin-2-carboxylic acid ethyl ester

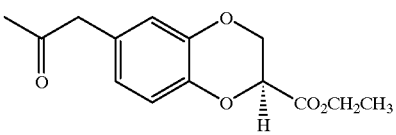

The title compound was obtained as colorless needles (recrystallized from ethyl acetate/hexane) by using (S)-6-formyl-2,3-dihydro-1,4-benzodioxin-2-carboxylic acid ethyl ester and ethanol according to the same process as described in Preparation Example 16. Yield=73%, 2 steps.

m.p. 61–62° C.; $[\alpha]_D^{28\ 28.7°}$ (c 1.18, $CHCl_3$).

The spectral data were identical with those of Preparation Example 17.

Preparation Example 58

(2R,2'R,2"R)-6-{2-[(N-tert-Butoxycarbonyl-(2-(3-chlorophenyl)-2-hydroxy)ethyl]amino}propyl-2, 3-dihydro-1,4-benzodioxin-2-carboxylic acid methyl ester

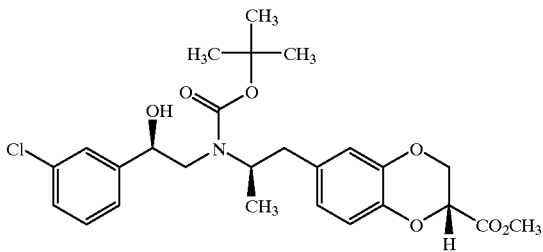

and
(2R,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester

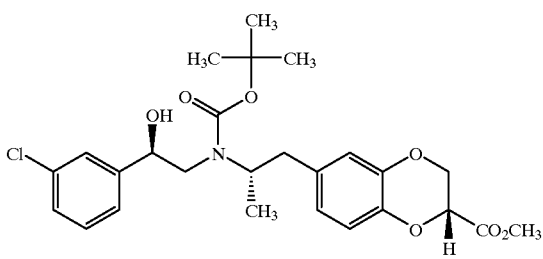

A solution of (R)-(-)-2-amino-1-(3-chlorophenyl)ethanol (2.07 g) and (R)-6-acetonyl-2,3-dihydro-1,4-benzodioxin-2-carboxylic acid methyl ester (2.87 g) in benzene (50 ml) was heated under reflux for one hour while removing a resulting water with Dean-Stark apparatus. The solvent was distilled off under reduced pressure, and the residue was dissolved in methanol (40 ml). To the solution was added platinum dioxide (200 mg), and the mixture was stirred under hydrogen atmosphere at room temperature for 2 hours. The reaction solution was filtered with Celite, and the solvent was distilled off under reduced pressure. The residue was subjected to a silica gel column chromatography (silica gel 60 g) to give the diastereomeric mixture (4.30 g, yield=92%) from the fraction of methanol/ethyl acetate/aqueous ammonia (15/85/2, v/v). Without further purification, this mixture (2.14 g) was dissolved in tetrahydrofuran (20 ml), and triethylamine (0.88 ml) was added. Then, to this solution was added at room temperature a solution of di-tert-butyl dicarbonate (1.27 g) in tetrahydrofuran (20 ml), and the mixture was stirred for 3.5 hours. The reaction solution was diluted with ethyl acetate (150 ml), washed in turn with water (50 ml) and saturated aqueous sodium chloride (50 ml), and dried over magnesium sulfate. The solvent was distilled off under reduced pressure. The residue was subjected to a silica gel column chromatography (silica gel 250 g) to give the colorless oily compound (2.31 g, yield=87%) from the fraction of ethyl acetate/chloroform (3/97, v/v). Further, the oily compound was subjected to a preparative high performance liquid chromatography with Chromatorex column (φ20 mm×250 mm, available from Fuji Silysia Chemical LTD) using ethyl acetate/hexane (1/4, v/v) as a mobile phase to give (2R,2'R,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester (474 mg, yield=18%) as a low polar, colorless oily substance and (2R,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester (590 mg, yield=22%) as a high polar, colorless oily substance.

(2R,2'R,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid methyl ester $[\alpha]_D^{29}$=−59.3° (c 1.10, CHCl$_3$); $^1$H NMR (CDCl$_3$, 40° C.) δ 1.21 (d, J=7.3 Hz, 3H), 1.42(s, 9H), 2.40–2.75(brm, 2H), 3.09(dd, J=2.4 Hz, 15.1Hz, 1H), 3.35–3.60(brm, 1H), 3.79 (s, 3H), 4.00–4.20(brm, 1H), 4.34(d, J=3.9 Hz, 2H), 4.70 (brd, J=8.8 Hz, 1H), 4.78(t, J=3.9 Hz, 1H), 6.55–6.70(brm, 2H), 6.89(d, J=7.8 Hz, 1H), 7.19–7.30(brm, 3H), 7.39(brs, 1H).

(2R,2'S,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid methyl ester $[\alpha]_D^{29}$=+35.2° (c 1.05, CHCl$_3$); 1H NMR (CDCl$_3$, 40° C.) δ 1.00–1.18(brs, 3H), 1.48(s, 9H), 2.56(dd, J=7.3 Hz, 13.7 Hz, 1H), 2.75–2.90(brm, 1H), 3.19(brd, J=12.7 Hz, 1H), 3.25–3.45(brm, 1H), 3.78(s, 3H), 3.90–4.02(m, 1H), 4.35(d, J=3.9 Hz, 2H), 4.75–4.82(brm, 2H), 6.64–6.73(brs, 2H), 6.90(d, J=8.8 Hz, 1H), 7.18–7.30(m, 3H), 7.36(brs, 1H).

Preparation Example 59

(2s,2'R,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid methyl ester

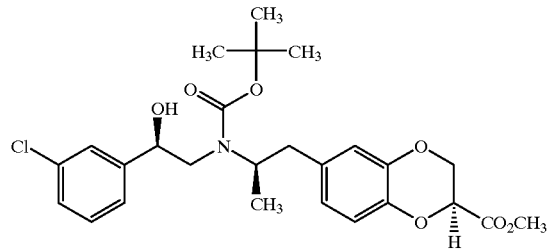

and
(2S,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester

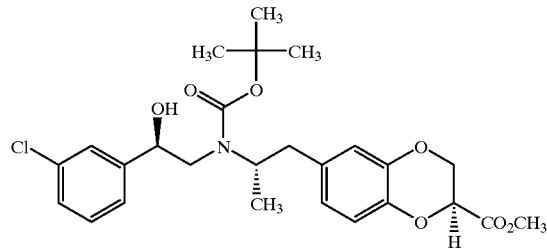

A low polar (2S,2'R,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester and a high polar (2S,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid methyl ester were obtained by using (S)-6-acetonyl-2,3-dihydro-1,4-benzodioxin-2-carboxylic acid methyl ester according to the same process as described in Preparation Example 58.

(2S,2'R,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid methyl ester Yield=39%. A colorless oily substance.

[α]$_D^{29}$=−81.0° (c 1.16, CHCl$_3$); $^1$H NMR (CDCl$_3$, 40° C.) δ 1.21 (d, J=7.3 Hz, 3H), 1.42(s, 9H), 2.40–2.75(brm, 2H), 3.09(dd, J=2.4, 15.1Hz, 1H), 3.35–3.60(brm, 1H), 3.79 (s, 3H), 4.00–4.20(brm, 1H), 4.34(d, J=3.9 Hz, 2H), 4.70 (brd, J=8.8 Hz, 1H), 4.78(t, J=3.9 Hz, 1H), 6.55–6.70(brm, 2H), 6.89 (d, J=7.8 Hz, 1H), 7.19–7.30(brm, 3H), 7.39(brs, 1H).

(2S,2'S,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid methyl ester Yield=24%. A colorless oily substance.

[α]$_D^{29}$=+3.2° (c 1.01, CHCl$_3$); $^1$H NMR (CDCl$_3$, 40° C.) δ 1.00–1.18(brs, 3H), 1.48(s, 9H), 2.56 (dd, J=7.3 Hz, 13.7 Hz, 1H), 2.75–2.90(brm, 1H), 3.19(brd, J=12.7 Hz, 1H), 3.25–3.45(brm, 1H), 3.78(s, 3H), 3.90–4.02(m, 1H), 4.35(d, J=3.9 Hz, 2H), 4.75–4.82(brm, 2H), 6.64–6.73(brs, 2H), 6.90(d, J=8.8 Hz, 1H), 7.18–7.30(m, 3H), 7.36(brs, 1H).

Preparation Example 60

(2R,2'R,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid ethyl ester

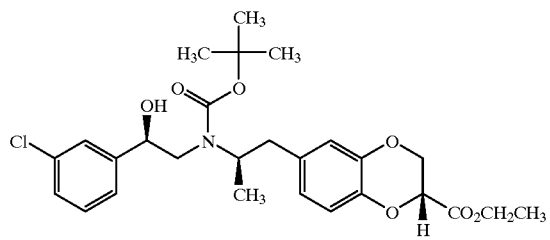

and
(2R,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid ethyl ester

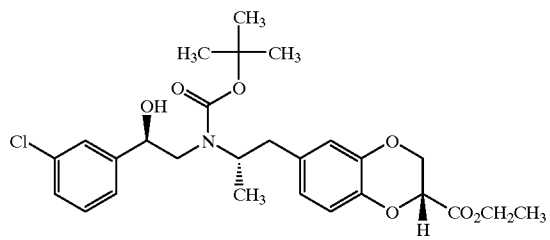

A low polar (2R, 2'R, 2"R)-6-{2-[(N-tert-butoxycarbonyl-( 2-(3-chlorophenyl)-2-hydroxyl)ethyl]amino}propyl-2,3-dihydro-1,4-benzodioxin-2-carboxylic acid ethyl ester and a high polar (2R,2'S,2"R)-6-{2-[(N-tert-butoxycarbonyl-(2-(3-chlorophenyl)-2-hydroxyl)ethyl]amino}propyl-2,3-dihydro-1,4-benzodioxin-2-carboxylic acid ethyl ester were obtained by using (R)-6-acetonyl-2,3-dihydro-1,4-benzodioxin-2-carboxylic acid ethyl ester according to the same process as described in Preparation Example 58.

(2R,2'R,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid ethyl ester Yield=27%. A colorless oily substance.

[α]$_D^{27}$=−58.8° (c 1.16, CHCl$_3$); $^1$H NMR (CDCl$_3$, 40° C.) δ 1.21 (d, J=6.8 Hz, 3H), 1.27(t, J=6.8 Hz, 3H), 1.42(s, 9H), 2.45–2.75(brm, 2H), 3.10(brd, J=15.1Hz, 1H), 3.40–3.60 (brm, 1H), 4.00–4.15(brm, 1H), 4.25(q, J=6.8 Hz, 2H), 4.33(brd, J=3.9 Hz, 2H), 4.71(brd, J=8.3 Hz, 1H), 4.75(t, J=4.4 Hz, 1H), 5.13–5.40(brm, 1H, substituted with deuterium oxide), 6.61(brd, J=7.8 Hz, 1H), 6.63(brs, 1H), 6.89(d, J=7.8 Hz, 1H), 7.20–7.30(brm, 3H), 7.39(brs, 1H).

(2R,2'S,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid ethyl ester Yield=15%. A colorless oily substance.

[α]$_D^{27}$=+31.3° (c 1.09, CHCl$_3$); $^1$H NMR (CDCl$_3$, 40° C.) δ 1.08 (brs, 3H), 1.26(t, J=7.3 Hz, 3H), 1.48(s, 9H), 2.56(dd, J=7.3 Hz, 13.7 Hz, 1H), 2.75–2.95(brm, 1H), 3.19(brd, J=12.7 Hz, 1H), 3.25–3.45(brm, 1H), 3.96(brq, J=6.8 Hz, 1H), 4.24(q, J=7.3 Hz, 2H), 4.35(d, J=3.9 Hz, 2H), 4.77(t, J=3.9 Hz, 1H), 4.80(brd, J=7.3 Hz, 1H), 6.64–6.70(brm, 2H), 6.90(d, J=8.8 Hz, 1H), 7.17–7.30(m, 3H), 7.37(brs, 1H).

Preparation Example 61

(2S,2'R,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid ethyl ester

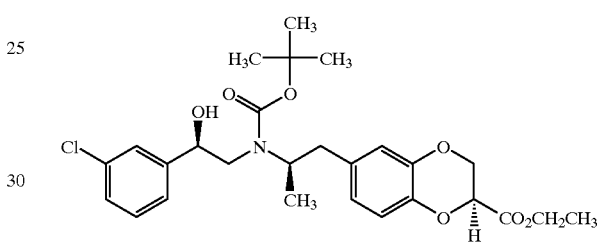

and
(2S,2'S,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid ethyl ester

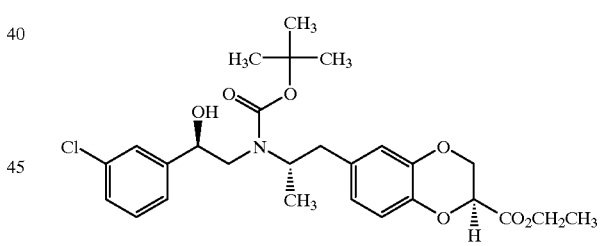

A low polar (2S,2'R,2"R)-6-{2-[(N-tert-butoxycarbonyl-(2-(3-chlorophenyl)-2-hydroxy)ethyl]amino}propyl-2,3-dihydro-1,4-benzodioxin-2-carboxylic acid ethyl ester and a high polar (2S,2'S,2"R)-6-{2-[(N-tert-butoxycarbonyl-( 2-(3-chlorophenyl)-2-hydroxy)ethyl]amino}propyl-2,3-dihydro-1,4-benzodioxin-2-carboxylic acid ethyl ester were obtained by using (S)-6-acetonyl-2,3-dihydro-1,4-benzodioxin-2-carboxylic acid ethyl ester according to the same process as described in Preparation Example 58.

(2S,2'R,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid ethyl ester Yield=39%. A colorless oily substance.

[α]$_D^{27}$=−80.2° (c 1.08, CHCl$_3$); $^1$H NMR (CDCl$_3$, 40° C.) δ 1.21(d, J=6.8 Hz, 3H), 1.27(t, J=6.8 Hz, 3H), 1.42(s, 9H), 2.45–2.75(brm, 2H), 3.09(dd, J=2.4 Hz, 15.1Hz, 1H), 3.40–3.60(brm, 1H), 4.00–4.15(brm, 1H), 4.24(q, J=6.8 Hz, 2H), 4.33(brd, J=3.9 Hz, 2H), 4.71(brd, J=8.3 Hz, 1H), 4.75(t, J=3.9 Hz, 1H), 5.13–5.40(brm, 1H, substituted with deuterium oxide), 6.62(brs, 1H), 6.63(brd, J=7.3 Hz, 1H), 6.89(d, J=7.8 Hz, 1H), 7.20–7.30(brm, 3H), 7.39(brs, 1H).

(2S,2'S,2"R)-6-{2-[(N-tert-Butoxycarbonyl-(2-(3-chlorophenyl)-2-hydroxy)ethyl]amino}propyl-2,3-dihydro-1,4-benzodioxin-2-carboxylic acid ethyl ester Yield=19%. A colorless oily substance.

$[\alpha]_D^{29}$=+12.5° (c 1.03, CHCl$_3$); $^1$H NMR (CDCl$_3$, 40°) δ 1.08 (brs, 3H), 1.26(t, J=7.3 Hz, 3H), 1.48(s, 9H), 2.56(dd, J=6.8 Hz, 13.7 Hz, 1H), 2.75–2.93(brm, 1H), 3.19(brd, J=14.2 Hz, 1H), 3.24–3.40(brm, 1H), 3.90–4.04(m, 1H), 4.23(q, J=6.8 Hz, 2H), 4.35(d, J=3.9 Hz, 2H), 4.66–4.85 (brm, 1H), 4.76(t, J=3.9 Hz, 2H), 4.66–4.85(brm, 1H), 4.76(t, J=3.9 Hz, 1H), 6.62–6.72(brm, 2H), 6.90(d, J=8.8 Hz, 1H), 7.17–7.30(m, 3H), 7.36(brs, 1H).

Illustrative examples of a pharmaceutical composition which comprises as an active ingredient the present compound are given below.

Pharmaceutical Preparation 1
Tablets (one tablet)

| | |
|---|---|
| Compound of Example 28 | 1 mg |
| Lactose | 70 mg |
| Crystalline cellulose | 20 mg |
| Corn starch | 8 mg |
| Magnesium stearate | 1 mg |
| a total amount | 100 mg |

All components were uniformly mixed to form powders for direct compression. The powders were formed in a rotary tableting machine to tablets having each 6 mm in diameter and 100 mg in weight.

Pharmaceutical Preparation 2
Granules (per divided packet)

| | | |
|---|---|---|
| A: | Compound of Example 29 | 1 mg |
| | Lactose | 99 mg |
| | Corn starch | 50 mg |
| | Crystalline cellulose | 50 mg |
| B: | Hydroxypropylcellulose | 10 mg |
| | Ethanol | 9 mg |

After all components of the above group A were uniformly mixed, a solution of the above group B was added. The mixture was kneaded and granulated by an extrusion granulation method. The granules were then dried in a drier at 50° C. The dried granules were screened to granule sizes between 297 μm and 1460 μm to give a granule formulation weighing 200 mg per divided packet.

Pharmaceutical Preparation 3
Syrups

| | |
|---|---|
| Compound of Example 30 | 0.100 g |
| Refined sugar | 30.000 g |
| D-sorbitol, 70 w/v % | 25.900 g |
| Ethyl paraoxybenzoate | 0.030 g |
| Propyl paraoxybenzoate | 0.015 g |
| Flavor | 0.200 g |
| Glycerin | 0.150 g |
| 96% Ethanol | 0.500 g |

-continued

| | |
|---|---|
| Distilled water | q.s. |
| a total amount | 100 ml |

The active ingredient, refined sugar, D-sorbitol, ethyl paraoxybenzoate and propyl paraoxybenzoate were dissolved in 60 g of warm water. After cooling, glycerin and a solution of flavor in ethanol were added. Then distilled water was added to the mixture to make up a total amount of 100 ml.

Effect of the Compound of the Present Invention

Pharmacological Example 1

β3 agonisitic activity in rats

The β3 agonisitic effect of the compounds of the present invention was determined by their activity to stimulate adipocyte lipolysis. Rat epididymal fat pads were excised and placed in a buffer containing the following composition: 130 mM sodium chloride, 4.7 mM potassium chloride, 1.25 mM magnesium sulfate, 2.8 mM calcium chloride, 10 mM HEPES, 2.5 mM sodium dihydrogenphosphate, 1 g/l glucose and 1% fatty acid-free serum albumin (pH 7.6). All the following procedures were carried out in the above-mentioned buffer. 5 g of a tissue was transferred to a plastic bottle with 10 ml of the buffer solution in which 0.1% collagenase (available from Worthington Biochemical corporation) was added.

The tissue was incubated at 37° C. for about 75 minutes with gentle shaking. After the cell suspension was filtered through nylon meshes (No. 100), the cells were washed three times with two volumes of the buffer, and it was again filtered through nylon meshes. The volume was adjusted with the buffer so that the adipocyte was brought to 20% volume. A 0.1 ml aliquot of the cell suspension was added to plastic test tubes with 0.3 ml of the buffer containing vehicle or compound. The cells were incubated at 37° C. for 120 minutes with gentle shaking. The reaction solution (0.3 ml) was transferred to a centrifuge tube with 50 ml of silicone oil (specific gravity 0.96, available from Shinetsu Chemical Industry), centrifuged at 18,500×g for one minute, and the reaction was stopped by removing the adipocyte from the buffer.

The amount of glycerol generated from the hydrolysis of triglycerides in the buffer was determined by a method using glycerol-3-phosphate oxidase/p-chlorophenol. 50 ml of the buffer was added to a 96-well plate which contained 0.2 ml of an assay mixture having the following composition: 50 mM Tris (pH 7.5), 5.4 mM p-chlorophenol, 250 mg/ml adenosine-5'-triphosphate disodium, 150 mg 4-aminoantipyrine, 250 U/l glycerol kinase, 500 U/l glycerol-3-phosphate oxidase, 1250 U/l horseradish peroxidase. The plate was incubated at 37° C. for 15 minutes, and then an absorbance at 505 nm was determined. The molar EC$_{50}$ value is the molar concentration of compound that gives 50% of that compound's own maximum rate of lipolysis.

TABLE 1

β3 agonisitic activity (rat)

| Compound of Example No. | Lipolysis Molar $EC_{50}$ value |
|---|---|
| Example 1 (hydrochloride) | $4.6 \times 10^{-8}$ |
| Example 2 (hydrochloride) | $4.0 \times 10^{-9}$ |
| Example 3 (hydrochloride) | $9.0 \times 10^{-9}$ |
| Example 4 (hydrochloride) | $5.6 \times 10^{-8}$ |
| Example 5 (hydrochloride) | $1.0 \times 10^{-7}$ |
| Example 11 (hydrochloride) | $2.4 \times 10^{-9}$ |
| Example 12 (hydrochloride) | $2.6 \times 10^{-8}$ |
| Example 28 (hydrochloride) | $1.0 \times 10^{-10}$ |
| Example 29 (hydrochloride) | $1.7 \times 10^{-9}$ |
| Example 30 (hydrochloride) | $1.6 \times 10^{-8}$ |
| Example 31 (hydrochloride) | $1.0 \times 10^{-7}$ |

Table 1 shows that the compounds of the present invention have potent β3 agonisitic activity.

Pharmacological Example 2
β3 agonistic activity on human β3 receptor

The β3 agonistic activity of the compounds was determined by their abilities to stimulate the intracellular cAMP production of human neuroblast. The human neuroblastoma cells (SK-N-MC) was available from American Type Culture Collection (HTB 10), and the cells were cultured under the atmosphere of 5% $CO_2$ at 37° C. on a 12-well plate in Dulbeccos' modified Eagle's medium containig 10% fetal calf serum. The SK-N-MC cells on reaching semi-confluence were washed twice with 1 ml of Hank's balanced salt solution (HBSS). After the cells were treated with 0.8 ml of HBSS containing 0.25 mM isobutylmethyl-xanthine at room temperature for 5 minutes, 0.1 ml of a test solution was added. Further, after incubation at 37° C. for 30 minutes, the reaction solution was aspirated, and washed twice with 2 ml of an ice-cooled phosphate-buffered saline (PBS). The cells were disrupted with 5 mM Tris buffer (pH 7.4) containing 2 mM EDTA, centrifuged at 18,500×g for one minute, and cAMP concentration in the supernatant was determined by EIA kit (available from Amersham). The ability of cAMP production was determined as a percentage of the compound to maximum activity of cAMP production of isopreterenol at $10^{-6}$M concentration (Proc. Natl. Acad. Sci. USA, 90, 3665, 1993).

TABLE 2

β3 agonisitic activity (an ability of cAMP production in neuroblastoma expressed by human β3 receptor)

| Compound of Example No. | Ability of cAMP production at $10^{-6}$ M, % (vs. Isopreterenol (ISP)) |
|---|---|
| Example 1 (hydrochloride) | 21 |
| Example 2 (hydrochloride) | 25 |
| Example 10 (hydrochloride) | 43 |
| Example 12 (hydrochloride) | 29 |

Table 2 shows that the compounds of the present invention have potent β3 agonisitic activity on human β3 receptor.

Pharmacological Example 3
Anti-hyperglycemic activity

The anti-hyperglycemic effect of the present compounds was determined using male KKAy mice with hyperglycemia of 300 mg/dl or more. The compound was orally administrated successively to the hyperglycemic mice for 4 days, and the blood glucose level was measured on the 5th day. The activity of the compounds was compared in terms of percent reduction in blood glucose level (a percentage of the blood glucose level after administration to that before administration). The measurement of blood glucose level was made by the method in which tail vein of mice was dissected with a scalpel and the blood was dropped onto an electrode of glucose sensor (Touekou Super, available from Kodama). Anti-hyperglycemic activity of the present compounds is shown below.

TABLE 3

Anti-hyperglycemic activity

| Compound of Example No. | Doses | Percent reduction in blood glucose level, % |
|---|---|---|
| Example 1 (hydrochloride) | 1 mg/kg | 53 |
| Example 3 (hydrochloride) | 1 mg/kg | 63 |
| Example 10 (hydrochloride) | 1 mg/kg | 48 |
| Example 28 (hydrochloride) | 1 mg/kg | 42 |
| Example 29 (hydrochloride) | 1 mg/kg | 54 |

Table 3 shows that the compounds of the present invention have potent anti-hyperglycemic activity in mouse of models of type II diabetes.

Industrial Applicability

The present compounds of formula (I) and the salts thereof have β3 agonistic activity, anti-hyperglycemic activity and anti-obesity activity. Consequently, these compounds are useful for a prophylactic or therapeutic agent for diabetes, hyperglycemia and obesity in mammals.

What is claimed is:

1. A 1,4-benzodioxin derivative represented by formula (I)

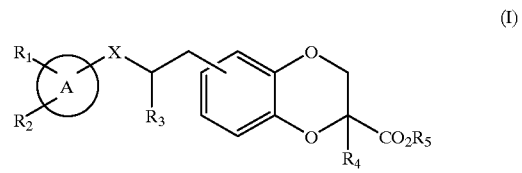

wherein
A is a phenyl group,
$R_1$ and $R_2$ may be the same or different, and each is a hydrogen atom, a halogen atom, a ($C_1$–$C_6$) alkyl group, a trifluoromethyl group, a ($C_1$–$C_6$) alkoxy group, an aryl group, an aryloxy group or an aryl($C_1$–$C_6$)alkyloxy group, the aryl, aryloxy or aryl($C_1$–$C_6$)alkoxy group being optionally substituted by one or two halogen atoms, or $R_1$ and $R_2$ together form —$OCH_2O$—,
$R_3$ is a hydrogen atom or a ($C_1$–$C_6$)alkyl group,
$R_4$ is a hydrogen atom,
$R_5$ is a hydrogen atom or a ($C_1$–$C_6$)alkyl group,
X is a divalent radical of formula (II)

wherein n is 1 or 2,
or a pharmaceutically acceptable salt thereof.

2. A compound of claim 1 represented by formula (I')

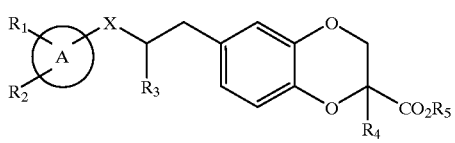

wherein A, $R_1$, $R_2$, $R_3$, $R_4$, $R_5$ and X have the same meanings as defined in claim 1, or a pharmaceutically acceptable salt thereof.

3. A compound of claim 1 wherein $R_1$ and $R_2$ may be the same or different, and each is a hydrogen atom, a halogen atom, a ($C_1$-$C_4$) alkyl group, a trifluoromethyl group, a ($C_1$-$C_4$)alkoxy group, a phenyl group, a phenoxy group or a benzyloxy group which may be optionally substituted by a halogen atom, or $R_1$ and $R_2$ together form —$OCH_2O$—, $R_3$ is a ($C_1$-$C_4$)alkyl group, $R_5$ is a hydrogen atom or a ($C_1$-$C_4$)alkyl group, or a pharmaceutically acceptable salt thereof.

4. A compound of claim 3 wherein both $R_1$ and $R_2$ are a hydrogen atom, or one of $R_1$ and $R_2$ is a hydrogen atom and the other is a halogen atom, a ($C_1$-$C_4$)alkyl group, a trifluoromethyl group, a ($C_1$-$C_4$)alkoxy group, a phenyl group, a phenoxy group or a benzyloxy group which may be optionally substituted by a halogen atom, or $R_1$ and $R_2$ together form —$OCH_2O$—, $R_3$ is a ($C_1$-$C_4$)alkyl group, $R_4$ is a hydrogen atom, $R_5$ is a hydrogen atom or a ($C_1$-$C_4$)alkyl group, or a pharmaceutically acceptable salt thereof.

5. A compound of claim 4 wherein both $R_1$ and $R_2$ are a hydrogen atom, or one of $R_1$ and $R_2$ is a hydrogen atom and the other is a fluorine atom, a chlorine atom, a methyl group, a trifluoromethyl group, a methoxy group, a phenyl group, a phenoxy group or a benzyloxy group which may be optionally substituted by a chlorine atom, or $R_1$ and $R_2$ together form —$OCH_2O$—, $R_3$ is a methyl group, $R_4$ is a hydrogen atom, $R_5$ is a hydrogen atom, a methyl group or an ethyl group, n is 1, or a pharmaceuticaly acceptable salt thereof.

6. A compound of claim 1 which is selected from the following compounds,

6-{2-[2-hydroxy-2-(3-methoxyphenyl)ethyl]amino}propyl-2,3-dihydro-1,4-benzodioxin-2-carboxylic acid methyl ester, 6-{2-[2-hydroxy-2-(3-tolyl)ethyl]amino}propyl-2,3-dihydro-1,4-benzodioxin-2-carboxylic acid methyl ester, 6-[2-(2-hydroxy-2-phenylethyl)amino]propyl-2,3-dihydro-1,4-benzodioxin-2-carboxylic acid methyl ester, 7-[2-(2-hydroxy-2-phenylethyl)amino]propyl-2,3-dihydro-1,4-benzodioxin-2-carboxylic acid methyl ester, 6-[2-(2-hydroxy-2-piperonylethyl)amino]propyl-2,3-dihydro-1,4-benzodioxin-2-carboxylic acid methyl ester, 6-{2-[2-(3-chlorophenyl)-2-hydroxyethyl]amino}propyl-2,3-dihydro-1,4-benzodioxin-2-carboxylic acid methyl ester, 6-{2-[2-hydroxy-2-(3-trifluoromethylphenyl)ethyl]amino}propyl- 2,3-dihydro-1,4-benzodioxin-2-carboxylic acid methyl ester, 6-{2-[2-hydroxy-2-(4-fluorophenyl)ethyl]amino}propyl-2,3-dihydro-1,4-benzodioxin-2-carboxylic acid methyl ester, (2'R,2"R)-6-{2-[2-(3-chlorophenyl)-2-hydroxyethyl]amino}propyl-2,3-dihydro-1,4-benzodioxin-2-carboxylic acid ethyl ester, (2'S,2"R)-6-{2-[2-(3-chlorophenyl)-2-hydroxyethyl]amino}propyl-2,3-dihydro-1,4-benzodioxin-2-carboxylic acid ethyl ester, (2R,2'R,2"R)-6-{2-[2-(3-chlorophenyl)-2-hydroxyethyl]amino}propyl-2,3-dihydro-1,4-benzodioxin-2-carboxylic acid ethyl ester hydrochloride, (2R,2'S,2"R)-6-{2-[2-(3-chlorophenyl)-2-hydroxyethyl]amino}propyl-2,3-dihydro-1,4-benzodioxin-2-carboxylic acid ethyl ester, (2S,2'R,2"R)-6-{2-[2-(3-chlorophenyl)-2-hydroxyethyl]amino}propyl-2,3-dihydro-1,4-benzodioxin-2-carboxylic acid ethyl ester, (2S,2'S,2"R)-6-{2-[2-(3-chlorophenyl)-2-hydroxyethyl]amino}propyl-2,3-dihydro-1,4-benzodioxin-2-carboxylic acid ethyl ester.

7. A pharmaceutical composition which comprises as an active ingredient a compound as defined in claim 1 or a pharmaceutically acceptable salt thereof.

8. A prophylactic or therapeutic agent for diabetes, hyperglycemia and obesity in mammals which comprises as an active ingredient a compound as defined in claim 1 or a pharmaceutically acceptable salt thereof.

9. A process of preparing a compound represented by formula (VII)

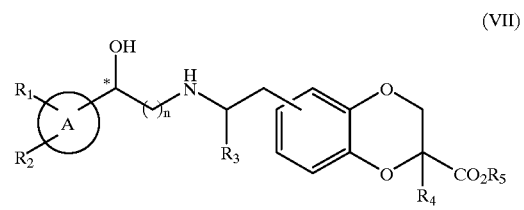

wherein A, $R_1$, $R_2$, $R_3$, $R_4$, $R_5$ and n are as defined for the following formulae (IV) and (V) which comprises reacting a compound of formula (IV)

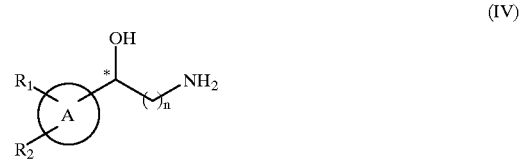

wherein A, $R_1$, $R_2$ and n are as defined in claim 1 with a compound of formula (V)

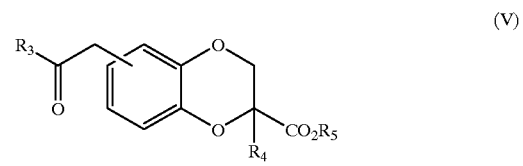

wherein $R_3$, $R_4$ and $R_5$ are as defined in claim 1 in a solvent to prepare a compound of formula (VI)

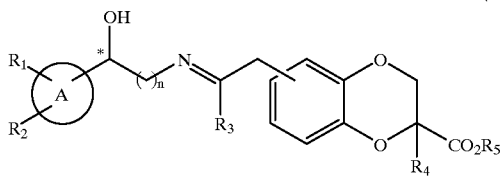
(VI)

wherein A, $R_1$, $R_2$, $R_3$, $R_4$, $R_5$ and n are as defined for formulae (IV) and (V), followed by reducing the compound of formula (VI).

10. A process of preparing a compound represented by formula (XIII)

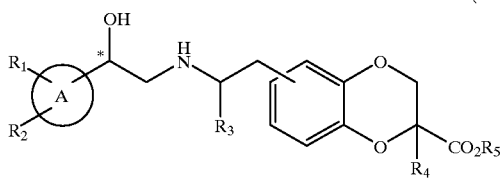
(XIII)

wherein A, $R_1$, $R_2$, $R_3$, $R_4$ and $R_5$ are as defired for the following formulae (XI) and (XII) which comprises reacting a compound of formula (XI)

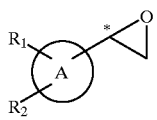
(XI)

wherein A, $R_1$, and $R_2$ are as defined in claim 1 with a compound of formula (XII)

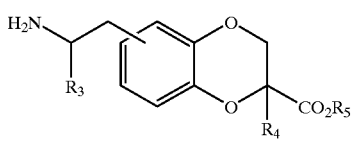
(XII)

wherein $R_3$, $R_4$ and $R_5$ are as defined in claim 1 in a solvent.

11. A process of preparing a compound represented by formula (XIII)

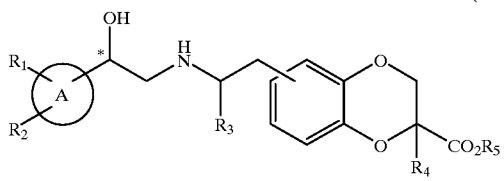
(XIII)

wherein A, $R_1$, $R_2$, $R_3$, $R_4$ and $R_5$ are as defined for the following formulae (XIV) and (XII) which comprises reacting a compound of formula (XIV)

(XIV)

wherein A, $R_1$, and $R_2$ are as defined in claim 1 and L is a leaving group with a compound of formula (XII)

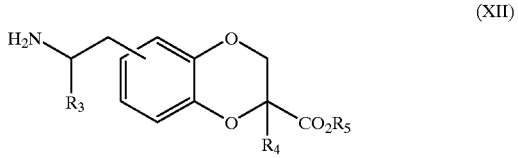
(XII)

wherein $R_3$, $R_4$ and $R_5$ are as defined in claim 1 in a solvent to prepare a compound of formula (XV)

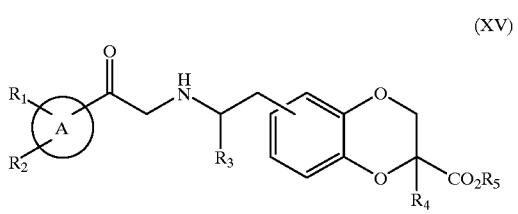
(XV)

wherein A, $R_1$, $R_2$, $R_3$, $R_4$ and $R_5$ are as defined for formulae (XIV) and (XII), followed by reducing the compound of formula (XV).

12. A method of treating diabetes, comprising administering an effective amount of the 1,4-benzodioxin derivative of claim 1, or a pharmaceutically acceptable salt thereof, to a patient in need thereof.

13. A method of treating hyperglycemia, comprising administering an effective amount of the 1,4-benzodioxin derivative of claim 1, or a pharmaceutically acceptable salt thereof, to a patient in need thereof.

14. A method of treating obesity, comprising administering an effective amount of the 1,4-benzodioxin derivative of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO. : 6,130,243  
DATED : October 10, 2000  
INVENTOR(S) : Takahashi et al.

Page 1 of 1

It is certified that error appears in the above-identified patent and that said Letters Patent is hereby corrected as shown below:

<u>Column 88,</u>  
Lines 60-65,

" 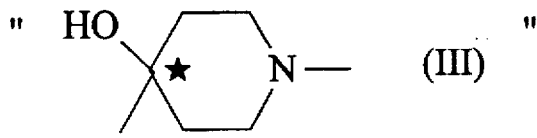 "

should read

-- 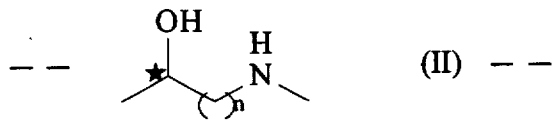 --

Signed and Sealed this

Thirteenth Day of November, 2001

*Attest:*

NICHOLAS P. GODICI  
*Attesting Officer*    *Acting Director of the United States Patent and Trademark Office*